(12) United States Patent
Wyndham et al.

(10) Patent No.: US 10,159,911 B2
(45) Date of Patent: *Dec. 25, 2018

(54) HIGH PURITY CHROMATOGRAPHIC MATERIALS COMPRISING AN IONIZABLE MODIFIER

(71) Applicant: Waters Technologies Corporation, Milford, MA (US)

(72) Inventors: Kevin Daniel Wyndham, Upton, MA (US); Pamela C. Iraneta, Brighton, MA (US); Thomas H. Walter, Ashland, MA (US)

(73) Assignee: Waters Technologies Corporation, Milford, MA (US)

( * ) Notice: Subject to any disclaimer, the term of this patent is extended or adjusted under 35 U.S.C. 154(b) by 1302 days.

This patent is subject to a terminal disclaimer.

(21) Appl. No.: 13/750,511

(22) Filed: Jan. 25, 2013

(65) Prior Publication Data

US 2013/0319086 A1    Dec. 5, 2013

Related U.S. Application Data

(63) Continuation-in-part of application No. 13/376,497, filed as application No. PCT/US2010/044390 on Aug. 4, 2010.

(60) Provisional application No. 61/231,045, filed on Aug. 4, 2009, provisional application No. 61/353,999, filed on Jun. 11, 2010.

(51) Int. Cl.
    *B01D 15/08*    (2006.01)
    *B01D 15/32*    (2006.01)
    (Continued)

(52) U.S. Cl.
    CPC ......... *B01D 15/36* (2013.01); *B01D 15/327* (2013.01); *B01D 15/3847* (2013.01);
    (Continued)

(58) Field of Classification Search
    CPC ...... B01D 15/08; B01D 15/32; B01D 15/327; B01D 15/368; B01D 15/361;
    (Continued)

(56) References Cited

U.S. PATENT DOCUMENTS 6,645,378 B1    11/2003  Liu et al.
7,125,488 B2    10/2006  Li
(Continued)

FOREIGN PATENT DOCUMENTS

CN    101002095 A    7/2007
JP    S61278759 A    12/1986
(Continued)

OTHER PUBLICATIONS

GE Healthcare, Brochure, "Protein and peptide purification: Technique selection guide." May 2007, 5 pages.*
(Continued)

*Primary Examiner* — Katherine Zalasky
(74) *Attorney, Agent, or Firm* — Womble Bond Dickinson (US) LLP; Deborah M. Vernon; Rebecca N. Barnes

(57) ABSTRACT

The present invention provides novel chromatographic materials, e.g., for chromatographic separations, processes for its preparation and separations devices containing the chromatographic material; separations devices, chromatographic columns and kits comprising the same; and methods for the preparation thereof. The chromatographic materials of the invention are high purity chromatographic materials comprising a chromatographic surface wherein the chromatographic surface comprises a hydrophobic surface group and one or more ionizable modifier.

13 Claims, 13 Drawing Sheets

(51) Int. Cl.
*B01J 20/32* (2006.01)
*B01J 20/286* (2006.01)
*B01D 15/36* (2006.01)
*G01N 30/90* (2006.01)
*B01D 15/38* (2006.01)
*B01J 20/29* (2006.01)
*B01D 15/18* (2006.01)

(52) U.S. Cl.
CPC ............ *B01J 20/286* (2013.01); *B01J 20/29* (2013.01); *B01J 20/3204* (2013.01); *B01J 20/3236* (2013.01); *B01J 20/3257* (2013.01); *B01J 20/3285* (2013.01); *G01N 30/90* (2013.01); *B01D 15/1871* (2013.01); *B01D 15/3833* (2013.01); *B01J 2220/52* (2013.01); *B01J 2220/54* (2013.01); *B01J 2220/58* (2013.01)

(58) Field of Classification Search
CPC .... B01D 15/362; B01D 15/305; G01N 30/48; G01N 30/482; G01N 2030/484; B01J 20/02; B01J 20/10; B01J 20/103; B01J 20/281; B01J 20/286; B01J 20/288; B01J 20/289
See application file for complete search history.

(56) References Cited

U.S. PATENT DOCUMENTS

| | | | |
|---|---|---|---|
| 7,402,243 B2 | 7/2008 | Liu et al. | |
| 7,972,872 B2 | 7/2011 | Shida et al. | |
| 2001/0033931 A1 | 10/2001 | Jiang et al. | |
| 2005/0178730 A1* | 8/2005 | Li | B01J 20/3227 210/656 |
| 2005/0230298 A1 | 10/2005 | Jiang et al. | |
| 2007/0189944 A1 | 8/2007 | Kirkland et al. | |
| 2009/0209722 A1 | 8/2009 | Jiang et al. | |
| 2012/0273404 A1 | 11/2012 | Wyndham et al. | |
| 2013/0319086 A1 | 12/2013 | Wyndham et al. | |

FOREIGN PATENT DOCUMENTS

| | | |
|---|---|---|
| JP | H11108913 A | 4/1999 |
| JP | 2002529714 A | 9/2002 |
| JP | 2006-504854 A | 2/2006 |
| JP | 2007-522476 A | 8/2007 |
| WO | 0027496 A1 | 5/2000 |
| WO | 2004041398 A2 | 5/2004 |
| WO | 2005079975 A1 | 9/2005 |
| WO | 2008103423 A1 | 8/2008 |
| WO | WO-2011/017418 | 2/2011 |

OTHER PUBLICATIONS

WO-PCT/ISA/210, dated Aug. 6, 2008, Waters Technologies Corporation.
Dettmer et al. "Mass Spectrometry-Based Metabolics", Mass Spectrom. Rev. 2007, vol. 26(1), pp. 51-79.
Bond et al., "Improving Qualitative and Quantitative Performacne for MSE-based Label-free Proteomics," Journal of Proteome research, Mar. 2013.
Geromanos, et al., "The detection, correlation and comparison of peptide precursor and product ions from data independent LCMS with data dependant LCMS/MS." Proteomics 9(6), 1683-95, (2009).

* cited by examiner

Comparison of the UV trace (A) taken at 214 nm for the BEH130 C18 showing the overloaded peaks for most cytochrome c peptides in order to get the T13-T14 peptide peak identification confirmed by MS. In the MS trace (B) the peak was identified as an m/z 807 with one missed cleavage.

Comparison of the UV trace (A) taken at 214 nm for the CSH130 C18 showing the same "overloaded" peaks for most cytochrome c peptides in order to get the T13-T14 peptide peak identification confirmed by MS. In the MS trace (B) the peak was identified as an m/z 807 with one missed cleavage.

HIGH PURITY CHROMATOGRAPHIC MATERIALS COMPRISING AN IONIZABLE MODIFIER

CROSS REFERENCE TO RELATED APPLICATIONS

This application is a Continuation-In-Part of U.S. patent application Ser. No. 13/376,497, filed Jul. 17, 2012, which application is the U.S. national phase, pursuant to 35 U.S.C. § 371, of PCT International Application Serial No. PCT/US2010/044390, filed Aug. 4, 2010, designating the United States and published in English on Feb. 10, 2011 as publication WO 2011/017418 A1, which claims priority to U.S. provisional application Ser. No. 61/231,045, filed Aug. 4, 2009, and U.S. provisional application Ser. No. 61/353,999, filed Jun. 11, 2010. The disclosures of all of the aforementioned patent applications are incorporated herein in their entireties by this reference.

BACKGROUND OF THE INVENTION

Packing materials for liquid chromatography (LC) are generally classified into two types: organic materials, e.g., polydivinylbenzene, and inorganic materials typified by silica. Many organic materials are chemically stable against strongly alkaline and strongly acidic mobile phases, allowing flexibility in the choice of mobile phase pH. However, organic chromatographic materials generally result in columns with low efficiency, particularly with low molecular-weight analytes. Many organic chromatographic materials not only lack the mechanical strength of typical chromatographic silica but also shrink and swell when the composition of the mobile phase is changed.

Silica is the material most widely used in High Performance Liquid Chromatography (HPLC), Ultra Performance Liquid Chromatography (UPLC), and Supercritical Fluid Chromatography (SFC). The most common applications employ silica that has been surface-derivatized with an organic functional group such as octadecyl (C18), octyl (C8), phenyl, amino, cyano, etc. As stationary phases for HPLC, these packing materials result in columns that have high efficiency and do not show evidence of shrinking or swelling.

Current Hybrid Material Technologies (HMT) provide important solutions to traditional chromatographic problems experienced with silica-based packing materials. HMT improvements include dramatically improved high and excellent low pH stability, great mechanical stability, good peak shape when used at pH 7, high efficiency, good retentivity, and desirable chromatographic selectivity.

However, two problems have been noted for some HMT and silica materials. The first is poor peak shape for bases when used at low pH and low ionic strength, which can negatively impact loadability and peak capacity when used at low pHunder these conditions.

A second problem observed for many HMT and silica materials is a change in acidic and basic analyte retention times (denoted 'drift') after a column is exposed to repeated changes in mobile phase pH (e.g., switching repeatedly from pH 10 to 3).

Thus, there remains a need for alternative materials that provide superior peak shape and reduced drift.

SUMMARY OF THE INVENTION

The present invention provides novel chromatographic materials, e.g., for chromatographic separations, processes for their preparation and separations devices containing the chromatographic materials.

In one aspect, the invention provides, a high purity chromatographic material (HPCM) comprising a chromatographic surface wherein the chromatographic surface comprises a hydrophobic surface group and one or more ionizable modifiers with the proviso that when the ionizable modifier does not contain a Zwitterion, the ionizable modifier does not contain a quaternary ammonium ion moiety.

In certain aspects the HPCM may further comprise a chromatographic core material. In some aspects, the chromatographic core is a silica material; a hybrid inorganic/organic material; or a superficially porous material.

In another aspect the ionizable modifier contains a carboxylic acid group, a sulfonic acid group, a phosphoric acid group, a boronic acid group, an amino group, an imido group, an amido group, a pyridyl group, an imidazolyl group, an ureido group, a thionyl-ureido group or an aminosilane group.

In another aspect, the ionizable modifier is selected from the group of zirconium, aluminum, cerium, iron, titanium, salts thereof, oxides and combinations thereof.

In another aspect, the ionizable modifier is provided by reacting the chromatographic surface with an ionizable modifying reagent selected from groups having formula (I)

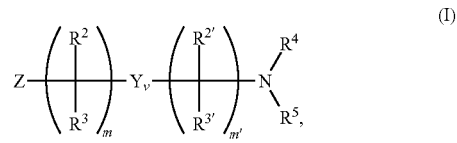

the formula (II):

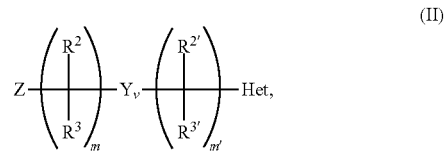

the formula (III):

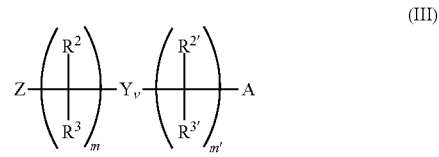

or a combination thereof
wherein
m is an integer from 1-8;
v is 0 or 1;
when v is 0, m' is 0;
when v is 1, m' is an integer from 1-8;
Z represents a chemically reactive group, including (but not limited to)

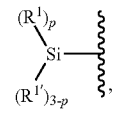

—OH, —OR$^6$, amine, alkylamine, dialkylamine, isocyanate, acyl chloride, triflate, isocyanate, thiocyanate, imidazole carbonate, NHS-ester, carboxylic acid, ester, epoxide, alkyne, alkene, azide, —Br, —Cl, or —I;

Y is an embedded polar functionality;

each occurrence of $R^1$ independently represents a chemically reactive group on silicon, including (but not limited to) —H, —OH, —$OR^6$, dialkylamine, triflate, Br, Cl, I, vinyl, alkene, or —$(CH_2)_{m''}Q$;

each occurrence of Q is —OH, —$OR^6$, amine, alkylamine, dialkylamine, isocyanate, acyl chloride, triflate, isocyanate, thiocyanate, imidazole carbonate, NHS-ester, carboxylic acid, ester, epoxide, alkyne, alkene, azide, —Br, —Cl, or —I;

m" is an integer from 1-8 p is an integer from 1-3;

each occurrence of $R^{1'}$ independently represents F, $C_1$-$C_{18}$ alkyl, $C_2$-$C_{18}$ alkenyl, $C_2$-$C_{18}$ alkynyl, $C_3$-$C_{18}$ cycloalkyl, $C_1$-$C_{18}$ heterocycloalkyl, $C_5$-$C_{18}$ aryl, $C_5$-$C_{18}$ aryloxy, or $C_1$-$C_{18}$ heteroaryl, fluoroalkyl, or fluoroaryl;

each occurrence of $R^2$, $R^{2'}$, $R^3$ and $R^{3'}$ independently represents hydrogen, $C_1$-$C_{18}$ alkyl, $C_2$-$C_{18}$ alkenyl, $C_2$-$C_{18}$ alkynyl, $C_3$-$C_{18}$ cycloalkyl, $C_1$-$C_{18}$ heterocycloalkyl, $C_5$-$C_{18}$ aryl, $C_5$-$C_{18}$ aryloxy, or $C_1$-$C_{18}$ heteroaryl, —Z, or a group having the formula —$Si(R')_bR''_a$ or —$C(R')_bR''_a$;

a and b each represents an integer from 0 to 3 provided that a+b=3;

R' represents a $C_1$-$C_6$ straight, cyclic or branched alkyl group;

R" is a functionalizing group selected from the group consisting of alkyl, alkenyl, alkynyl, aryl, cyano, amino, diol, nitro, ester, a cation or anion exchange group, an alkyl or aryl group containing an embedded polar functionality and a chiral moiety.

$R^4$ represents hydrogen, $C_1$-$C_{18}$ alkyl, $C_2$-$C_{18}$ alkenyl, $C_2$-$C_{18}$ alkynyl, $C_3$-$C_{18}$ cycloalkyl, $C_1$-$C_{18}$ heterocycloalkyl, $C_5$-$C_{18}$ aryl, $C_5$-$C_{18}$ aryloxy, or $C_1$-$C_{18}$ heteroaryl;

$R^5$ represents hydrogen, $C_1$-$C_{18}$ alkyl, $C_2$-$C_{18}$ alkenyl, $C_2$-$C_{18}$ alkynyl, $C_3$-$C_{18}$ cycloalkyl, $C_1$-$C_{18}$ heterocycloalkyl, $C_5$-$C_{18}$ aryl, $C_5$-$C_{18}$ aryloxy, or $C_1$-$C_{18}$ heteroaryl;

each occurrence of $R^6$ independently represents $C_1$-$C_{18}$ alkyl, $C_2$-$C_{18}$ alkenyl, $C_2$-$C_{18}$ alkynyl, $C_3$-$C_{18}$ cycloalkyl, $C_1$-$C_{18}$ heterocycloalkyl, $C_5$-$C_{18}$ aryl, $C_5$-$C_{18}$ aryloxy, or $C_1$-$C_{18}$ heteroaryl;

Het represents a heterocyclic or heteroaryl ring system comprising at least one nitrogen atom; and A represents an acidic ionizable modifier moiety or a dual charge ionizable modifier moiety.

In certain aspects, where the ionizable modifying reagent is selected from formula (III), A represents a protected or unprotected alkyl, aryl, or arylalkyl groups containing phosphoric, carboxylic, sulfonic, or boronic acid.

In certain other aspects, where the ionizable modifying reagent is selected from formula (III), A represents a dual charge ionizable modifier. While not limited to theory; the dual charge ionizable modifier has two sub-groups that can display opposite charges. Under some conditions the dual charge ionizable modifier can act similarly to a zwitterions and ampholytes to display both a positive and negative charge and maintain a zero net charge. Under other conditions the dual charge ionizable may only have one group ionized and may display a net positive or negative charge.

Dual charge ionizable modifying reagents include, but are not limited to, alkyl, branched alkyl, aryl, cyclic, polyaromatic, polycyclic, hertocyclic and polyheterocyclic groups that can display a positive charge (commonly on a nitrogen or oxygen atom), and a negative charge through an acidic group that includes a carboxylic, sulfonic, phosphonic or boronic acid. Alternatively, some metal containing complexes can display both positive and negative charges.

Dual charge ionizable modifying reagents may also include, but are not limited to Zwitterion, ampholyte, amino acid, aminoalkyl sulfonic acid, aminoalkyl carboxylic acid, mono and di-methylaminoalkyl sulfonic acid, mono and di-methylaminoalkyl carboxylic acid, pyridinium alkyl sulfonic acid, and pyridinium alkyl carboxylic acid groups. Alternatively the dual charge ionizable modifier may include 2-(N-morpholino)ethanesulfonic acid, 3-(N-morpholino)propanesulfonic acid, 4-(2-hydroxyethyl)-1-piperazine ethanesulfonic acid, piperazine-N,N'-bis(2-ethanesulfonic acid), N-cyclohexyl-3-aminopropanesulfonic acid, N-cyclohexyl-2-hydroxyl-3-aminopropanesulfonic acid, 3-[(3-cholamidopropyl)dimethylammonio]-1-propanesulfonate, 6-Methyl-9,10-didehydro-ergoline-8-carboxylic acid, phenolsulfonphthalein, betaine, quinonoid, N,N-bis(2-hydroxyethyl)glycine, and N-[tris(hydroxymethyl)methyl]glycine groups.

In certain aspects, where the ionizable modifying reagent is selected from formulas (I), (II) or (1H), m is 2 or 3.

In some aspects, where the ionizable modifying reagent is selected from formulas (I), (II) or (III), $R^1$ represents Cl, —OH, dialkylamino, methoxy or ethoxy.

In certain aspects, where the ionizable modifying reagent is selected from formulas (I), (II) or (III), $R^{1'}$ represents, methyl, ethyl, isobutyl, isopropyl or tert-butyl.

In other aspects where the ionizable modifying reagent is selected from formulas (I), (II) or (III), each occurrence of $R^2$ and $R^3$ represents hydrogen.

In other aspects where the ionizable modifying reagent is selected from formulas (I), (II) or (III), each occurrence of $R^{2'}$ and $R^{3'}$ represents hydrogen.

In other aspects where the ionizable modifying reagent is selected from formula (I), each of $R^4$ and $R^5$ represents hydrogen.

In still other aspects where the ionizable modifying reagent is selected from formulas (II), Het is pyridyl, pyrimidinyl, pyridazinyl, pyrazinyl, piperidinyl, piperizinyl, hexahydropyrimidinyl, pyrrolyl, pyrazolyl, imidazolyl, pyrrolidinyl, pyrazolidinyl, imidazolidinyl or triazinyl.

In other aspects where the ionizable modifying reagent is selected from formulas (I), (II) or (III), V is 1, m' is 3, and each occurrence of $R^2$, $R^{2'}$, $R^3$ and $R^{3'}$ is hydrogen. In certain aspects, where the ionizable modifying reagent is selected from formulas (I), (II) or (III), V is 1, m' is 3, and each occurrence of $R^2$, $R^{2'}$, $R^3$ and $R^{3'}$ is hydrogen, Y is carbamate, carbonate, amide, urea, ether, thioether, sulfinyl, sulfoxide, sulfonyl, thiourea, thiocarbonate, thiocarbamate or triazole.

In yet other aspects, the ionizable modifying reagent is aminopropyltriethoxysilane, aminopropyltrimethoxysilane, 2-(2-(trichlorosilyl)ethyl)pyridine, 2-(2-(trimethoxy)ethyl)pyridine, 2-(2-(triethoxy)ethyl)pyridine, 2-(4-pyridylethyl)triethoxysilane, 2-(4-pyridylethyl)trimethoxysilane, 2-(4-pyridylethyl)trichlorosilane, chloropropyltrimethoxysilane, chloropropyltrichlorosilane, chloropropyltrichlorosilane, chloropropyltriethoxysilane, imidazolylpropyltrimethoxysilane, imidazolylpropyltriethoxysilane, imidazolylpropyltrichlorosilane, sulfopropyltrisilanol, carboxyethylsilanetriol, 2-(carbomethoxy)ethylmethyldichlorosilane, 2-(carbomethoxy)ethyltrichlorosilane, 2-(carbomethoxy)ethyltrimethoxysilane, n-(trimethoxysilylpropyl)ethylenediamine triacetic acid, (2-diethylphosphatoethyl)triethoxysilane, 3-mercaptopropyltriethoxysilane, 3-mercaptopropyltrimethoxysilane, bis[3-(triethoxysilyl)propyl]disulfide, bis

[3-(triethoxysilyl)propyl]tetrasulfide, 2,2-dimethoxy-1-thia-2-silacyclopentane, bis(trichlorosilylethyl)phenylsulfonyl chloride, 2-(chlorosulfonylphenyl)ethyltrichlorosilane, 2-(chlorosulfonylphenyl)ethyltrimethoxysilane, 2-(ethoxysulfonylphenyl)ethyltrimethoxysilane, 2-(ethoxysulfonylphenyl)ethyltrimethoxysilane, 2-(ethoxysulfonylphenyl)ethyltrichlorosilane, sulphonic acid phenethyltrisilanol, (triethoxysilyl ethyl)phenyl phosphonic acid diethyl ester, (trimethoxysilyl ethyl)phenyl phosphonic acid diethyl ester, (trichlorosilyl ethyl)phenyl phosphonic acid diethyl ester, phosphonic acid phenethyltrisilanol, N-(3-trimethoxysilylpropyl)pyrrole, N-(3-triethoxysilylpropyl)-4,5-dihydroimidazole, bis(methyldimethoxysilylpropyl)-N-methylamine, tris(triethoxysilylpropyl)amine, bis(3-trimethoxysilylpropyl)-N-methylamine, (N,N-diethyl-3-aminopropyl)trimethoxysilane, N-(hydroxyethyl)-N-methylaminopropyltrimethoxysilane, 3-(N,N-dimethylaminopropyl)trimethoxysilane, bis(2-hydroxyethyl)-3-aminopropyltriethoxysilane, N,N'-bis(hydroxyethyl)-N,N'-bis(trimethoxysilylpropyl)ethylenediamine, or N,N-dimethyl-3-aminopropylmethyldimethoxysilane.

In some aspects, the ratio of the hydrophobic surface group:ionizable modifier in the HPCM of the invention is from about 2.5:1 to about 350:1; from about 3:1 to about 200:1; from about 4:1 to about 150:1; from about 4:1 to about 35:1; from about 5:1 to about 25:1; from about 5:1 to about 22:1; from about 20:1 to about 100:1; or from about 25:1 to about 100:1.

In other aspects, the concentration of ionizable modifier in the HPCM of the invention is less than about 0.5 $\mu mol/m^2$; less than about 0.4 $\mu mol/m^2$; less than about 0.3 $\mu mol/m^2$; from about 0.01 $\mu mol/m^2$ to about 0.5 $\mu mol/m^2$; from about 0.01 $\mu mol/m^2$ to about 0.4 $\mu mol/m^2$; or from about 0.03 $\mu mol/m^2$ to about 0.3 $\mu mol/m^2$.

In another aspect, the hydrophobic surface group of the HPCM of the invention is a $C_4$ to $C_{30}$ bonded phase. In certain aspects, the hydrophobic surface group is a $C_{18}$ bonded phase. In other aspects, the hydrophobic surface group is an aromatic, phenylalkyl, fluoro-aromatic, phenylhexyl, pentafluorophenylalkyl or chiral bonded phase. In still other aspects, the hydrophobic surface group is an embedded polar bonded phase.

In certain aspects, the HPCM of the invention may be in the form of a particle, a granular material, a monolith, a superficially porous material, a superficially porous particle, a superficially porous monolith, or a superficially porous layer for open tubular chromatography.

In certain aspects, the HPCM of the invention may be in inorganic material (e.g., silica, alumina, titania, zirconia), a hybrid organic/inorganic material, an inorganic material (e.g., silica, alumina, titania, zirconia) with a hybrid surface layer, a hybrid material with an inorganic (e.g., silica, alumina, titania, zirconia) surface layer, or a hybrid material with a different hybrid surface layer. In other aspects, the HPCM of the invention may have ordered pore structure, non-periodic pore structuring, non-crystalline or amorphous pore structuring or substantially disordered pore structuring.

In one aspect, the HPCM of the invention does not have chromatographically enhancing pore geometry.

In another aspect, the HPCM of the invention has chromatographically enhancing pore geometry.

In certain aspects, the HPCM of the invention has a surface area of about 25 to 1100 $m^2/g$; about 80 to 500 $m^2/g$; or about 120 to 330 $m^2/g$.

In other aspects, the HPCM of the invention has a pore volume of about 0.15 to 1.5 $cm^3/g$; or about 0.5 to 1.3 $cm^3/g$.

In yet other aspects, the HPCM of the invention has a micropore surface area of less than about 110 $m^2/g$; less than about 105 $m^2/g$; less than about 80 $m^2/g$; or less than about 50 $m^2/g$.

In still yet other aspects, the HPCM of the invention has an average pore diameter of about 20 to 1500 Å; about 50 to 1000 Å; about 100 to 750 Å; or about 110 to 500 Å.

In still yet other aspects, when the HPCM of the invention is in the form of a particle, the HPCM of the invention has an average particle size of about 0.3-100 µm; about 0.5-20 µm; 0.8-10 µm; or about 1.0-3.5 µm.

In another aspect, the HPCM of the invention is hydrolytically stable at a pH of about 1 to about 14; at a pH of about 10 to about 14; or at a pH of about 1 to about 5.

In still another aspect, the HPCM of the invention has a quantified surface coverage ratio, B/A, from about 2.5 to about 300 wherein A represents the ionizable modifier and B represents the hydrophobic group. In certain aspects, the quantified surface coverage ratio, B/A, is from about 3 to about 200, from about 4 to about 35 or from about 5 to about 22.

In another aspect, the HPCM of the invention may be surface modified. In certain aspects, the HPCM of the invention may be surface modified by coating with a polymer. In other aspects, the HPCM of the invention may be surface modified by coating with a polymer by a combination of organic group and silanol group modification; by a combination of organic group modification and coating with a polymer; or by a combination of silanol group modification and coating with a polymer. In other aspects, the HPCM of the invention may be material has been surface modified by a combination of organic group modification, silanol group modification and coating with a polymer. In still other aspects, the HPCM of the invention may be surface modified via formation of an organic covalent bond between the material's organic group and the modifying reagent.

In certain aspects, the HPCM of the invention may further comprising a nanoparticle dispersed within the material. In aspects further comprising a nanoparticle, the nanoparticle may be a mixture of more than one nanoparticle. In some aspects comprising a nanoparticle, the nanoparticle is present in <20% by weight of the nanocomposite or in <5% by weight of the nanocomposite. In other aspects comprising a nanoparticle, the nanoparticle is crystalline or amorphous. In certain aspects, the nanoparticle is a substance which comprises one or more moieties selected from the group consisting of silicon carbide, aluminum, diamond, cerium, carbon black, carbon nanotubes, zirconium, barium, cerium, cobalt, copper, europium, gadolinium, iron, nickel, samarium, silicon, silver, titanium, zinc, boron, oxides thereof, and nitrides thereof. In certain other aspects, the nanoparticle is a substance which comprises one or more moieties selected from the group consisting of nano-diamonds, silicon carbide, titanium dioxide, cubic-boronitride. In another aspect, the nanoparticles are less than or equal to 200 nm in diameter; less than or equal to 100 nm in diameter; less than or equal to 50 nm in diameter; or less than or equal to 20 nm in diameter.

In another aspect, the invention provides a method for selectively isolating a macromolecule from a sample, the method comprising the steps of:
  a) loading a sample containing a macromolecule onto a chromatographic separations device comprising a high purity chromatographic material comprising a chromatographic surface wherein the chromatographic surface comprises a hydrophobic surface group and one or more ionizable modifiers such that the macromolecule is selectively adsorbed onto the high purity chromatographic material, with the proviso that when the ionizable modifier does not contain a Zwitterion, the ionizable modifier does not contain a quaternary ammonium ion moiety; and b) eluting the adsorbed macromolecule from the high purity chromatographic material, thereby selectively isolating the macromolecule from the sample.

In still another aspect, the invention provides a method for separating a plurality of macromolecules from a sample, the method comprising the steps of:
 a) loading a sample containing a plurality of macromolecules onto chromatographic separations device comprising a high purity chromatographic material comprising a chromatographic surface wherein the chromatographic surface comprises a hydrophobic surface group and one or more ionizable modifiers such that the macromolecules are adsorbed onto the high purity chromatographic material, with the proviso that when the ionizable modifier does not contain a Zwitterion, the ionizable modifier does not contain a quaternary ammonium ion moiety; and
 b) eluting the adsorbed macromolecules from the high purity chromatographic material, thereby separating the macromolecules.

In yet another aspect, the invention provides a method for purifying a macromolecule contained in a sample, the method comprising the steps of:
 a) loading a sample containing a macromolecule onto chromatographic separations device comprising a high purity chromatographic material comprising a chromatographic surface wherein the chromatographic surface comprises a hydrophobic surface group and one or more ionizable modifiers such that the macromolecule are adsorbed onto the high purity chromatographic material, with the proviso that when the ionizable modifier does not contain a Zwitterion, the ionizable modifier does not contain a quaternary ammonium ion moiety; and
 b) eluting the adsorbed macromolecule from the high purity chromatographic material, thereby purifying a macromolecule.

In still yet another aspect, the invention provides a method for detecting a macromolecule in a sample, the method comprising the steps of:
 a) loading a sample containing a macromolecule onto chromatographic separations device comprising a high purity chromatographic material comprising a chromatographic surface wherein the chromatographic surface comprises a hydrophobic surface group and one or more ionizable modifiers such that the macromolecules are adsorbed onto the high purity chromatographic material, with the proviso that when the ionizable modifier does not contain a Zwitterion, the ionizable modifier does not contain a quaternary ammonium ion moiety; and
 b) eluting the adsorbed macromolecule from the high purity chromatographic material; and
 c) detecting the macromolecule.

In certain aspects of the chromatographic methods of the invention, the macromolecule is selected from the group consisting of a peptide, a polypeptide, a phosphopeptide, a glycopeptide, a protein, a phosphoprotein, a nucleic acid, an oligonucleotide, a polynucleotide, a phospholipid, a synthetic or natural polymer, a functionalize macromolecule and mixtures thereof.

In certain embodiments of the chromatographic methods of the invention, the chromatographic separations device utilized in the method is a device is selected from the group consisting of a chromatographic column, a thin layer plate, a filtration membrane, a microfluidic separation device, a sample cleanup device, a solid support, a solid phase extraction device, a microchip separation device, and a microtiter plate.

In other aspects of the chromatographic methods of the invention, a second dimension is utilized to prepare the sample or to further purify, isolate, or separate the macromolecules. In such aspects, the methods of the invention further comprise the step of preparing the sample for use in the methods by treating a mother sample to a secondary chromatographic means to obtain the sample. Alternatively, or in addition, the methods of the invention further comprise the step of treating the macromolecules eluted in the application of the methods of the invention with a secondary chromatographic means to further isolate, purify, or separate the macromolecules. In such aspects, the secondary chromatographic means may be a second chromatographic separations device comprising a chromatographic material other than a high purity chromatographic material comprising a chromatographic surface wherein the chromatographic surface comprises a hydrophobic surface group and one or more ionizable modifiers. In other such aspects, the secondary chromatographic means may be a second chromatographic material comprised by chromatographic separations device utilized in the methods of the invention other than a high, purity chromatographic material comprising a chromatographic surface wherein the chromatographic surface comprises a hydrophobic surface group and one or more ionizable modifiers. In those aspects in which a secondary chromatographic separations device is utilized, such a device is selected from the group consisting of a chromatographic column, a thin layer plate, a filtration membrane, a microfluidic separation device, a sample cleanup device, a solid support, a solid phase extraction device, a microchip separation device, and a microtiter plate.

DETAILED DESCRIPTION OF THE INVENTION

Figure 1:
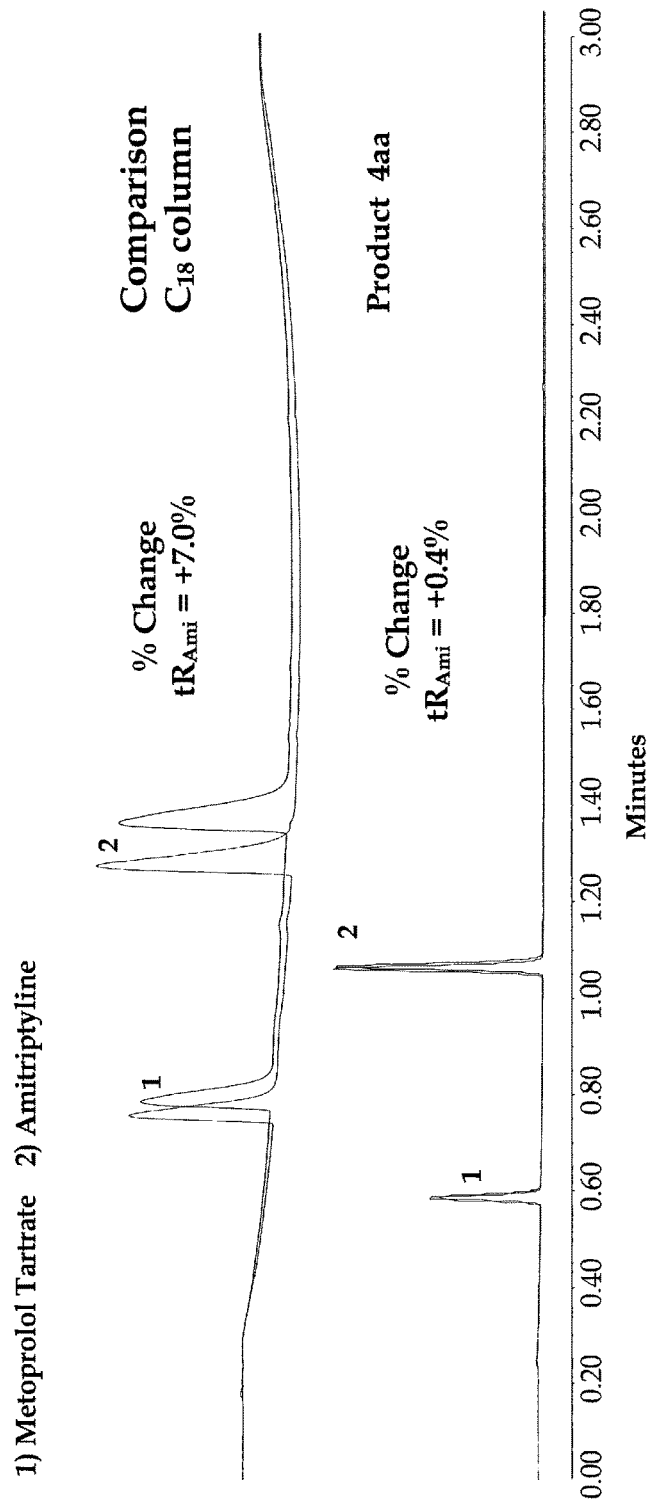
FIG. 1 depicts the drift with pH switching (from pH 3 to pH 10) using (a) a traditional, commercial C18 bonded material and (b) the material of the instant invention.

The present invention provides novel chromatographic materials, e.g., for chromatographic separations, processes for their preparation and separations devices containing the chromatographic material. The present invention will be more fully illustrated by reference to the definitions set forth belows.

Definitions

"High Purity" or "high purity chromatographic material" includes a material which is prepared form high purity precursors. In certain aspects, high purity materials have reduced metal contamination and/or non-diminished chromatographic properties including, but not limited to, the acidity of surface silanols and the heterogeneity of the surface.

"Chromatographic surface" includes a surface which provides for chromatographic separation of a sample. In certain aspects, the chromatographic surface is porous. In some aspects, a chromatographic surface may be the surface of a particle, a superficially porous material or a monolith. In certain aspects, the chromatographic surface is composed of the surface of one or more particles, superficially porous materials or monoliths used in combination during a chromatographic separation. In certain other aspects, the chromatographic surface is non-porous.

"Ionizable modifier" includes a functional group which bears an electron donating or electron withdrawing group. In certain aspects, the ionizable modifier contains one or more carboxylic acid groups, amino groups, imido groups, amido groups, pyridyl groups, imidazolyl groups, ureido groups, thionyl-ureido groups or aminosilane groups, or a combination thereof. In other aspects, the ionizable modifier contains a group bearing a nitrogen or phosphorous atom having a free electron lone pair. In certain aspects, the ionizable modifier is covalently attached to the material surface and has an ionizable group. In some instances it is attached to the chromatographic material by chemical modification of a surface hybrid group.

"Hydrophobic surface group" includes a surface group on the chromatographic surface which exhibits hydrophobicity. In certain aspects, a hydrophobic group can be a carbon bonded phase such as a C4 to C18 bonded phase. In other aspects, a hydrophobic surface group can contain an embedded polar group such that the external portion of the hydrophobic surface maintains hydrophobicity. In some instances it is a attached to the chromatographic material by chemical modification of a surface hybrid group. In other instances the hydrophobic group can be C4-C30, embedded polar, chiral, phenylalkyl, or pentafluorophenyl bonding and coatings.

"Chromatographic core" includes a chromatographic materials, including but not limited to an organic material such as silica or a hybrid material, as defined herein, in the form of a particle, a monolith or another suitable structure which forms an internal portion of the materials of the invention. In certain aspects, the surface of the chromatographic core represents the chromatographic surface, as defined herein, or represents a material encased by a chromatographic surface, as defined herein. The chromatographic surface material may be disposed on or bonded to or annealed to the chromatographic core in such a way that a discrete or distinct transition is discernable or may be bound to the chromatographic core in such a way as to blend with the surface of the chromatographic core resulting in a gradation of materials and no discrete internal core surface. In certain embodiments, the chromatographic surface material may be the same or different from the material of the chromatographic core and may exhibit different physical or physiochemical properties from the chromatographic core, including, but not limited to, pore volume, surface area, average pore diameter, carbon content or hydrolytic pH stability "Hybrid", including "hybrid inorganic/organic material," includes inorganic-based structures wherein an organic functionality is integral to both the internal or "skeletal" inorganic structure as well as the hybrid material surface. The inorganic portion of the hybrid material may be, e.g., alumina, silica, titanium, cerium, or zirconium or oxides thereof, or ceramic material.

"Hybrid" includes inorganic-based structures wherein an organic functionality is integral to both the internal or "skeletal" inorganic structure as well as the hybrid material surface. As noted above, exemplary hybrid materials are shown in U.S. Pat. Nos. 4,017,528, 6,528,167, 6,686,035 and 7,175,913.

The term "alicyclic group" includes closed ring structures of three or more carbon atoms. Alicyclic groups include cycloparaffins or naphthenes which are saturated cyclic hydrocarbons, cycloolefins, which are unsaturated with two or more double bonds, and cycloacetylenes which have a triple bond. They do not include aromatic groups. Examples of cycloparaffins include cyclopropane, cyclohexane and cyclopentane. Examples of cycloolefins include cyclopentadiene and cyclooctatetraene. Alicyclic groups also include fused ring structures and substituted alicyclic groups such as alkyl substituted alicyclic groups. In the instance of the alicyclics such substituents can further comprise a lower alkyl, a lower alkenyl, a lower alkoxy, a lower alkylthio, a lower alkylamino, a lower alkylcarboxyl, a nitro, a hydroxyl, —$CF_3$, —CN, or the like. The term "aliphatic group" includes organic compounds characterized by straight or branched chains, typically having between 1 and 22 carbon atoms. Aliphatic groups include alkyl groups, alkenyl groups and alkynyl groups. In complex structures, the chains can be branched or cross-linked. Alkyl groups include saturated hydrocarbons having one or more carbon atoms, including straight-chain alkyl groups and branched-chain alkyl groups. Such hydrocarbon moieties may be substituted on one or more carbons with, for example, a halogen, a hydroxyl, a thiol, an amino, an alkoxy, an alkylcarboxy, an alkylthio, or a nitro group. Unless the number of carbons is otherwise specified, "lower aliphatic" as used herein means an aliphatic group, as defined above (e.g., lower alkyl, lower alkenyl, lower alkynyl), but having from one to six carbon atoms. Representative of such lower aliphatic groups, e.g., lower alkyl groups, are methyl, ethyl, n-propyl, isopropyl, 2-chloropropyl, n-butyl, sec-butyl, 2-aminobutyl, isobutyl, tert-butyl, 3-thiopentyl and the like. As used herein, the term "nitro" means —$NO_2$; the term "halogen" designates —F, —Cl, —Br or —I; the term "thiol" means SH; and the term "hydroxyl" means —OH. Thus, the term "alkylamino" as used herein means an alkyl group, as defined above, having an amino group attached thereto. Suitable alkylamino groups include groups having 1 to about 12 carbon atoms, preferably from 1 to about 6 carbon atoms. The term "alkylthio" refers to an alkyl group, as defined above, having a sulfhydryl group attached thereto. Suitable alkylthio groups include groups having 1 to about 12 carbon atoms, preferably from 1 to about 6 carbon atoms. The term "alkylcarboxyl" as used herein means an alkyl group, as defined above, having a carboxyl group attached thereto. The term "alkoxy" as used herein means an alkyl group, as defined above, having an oxygen atom attached thereto. Representative alkoxy groups include groups having 1 to about 12 carbon atoms, preferably 1 to about 6 carbon atoms, e.g., methoxy, ethoxy, propoxy, tert-butoxy and the like. The terms "alkenyl" and "alkynyl" refer to unsaturated aliphatic groups analogous to alkyls, but which contain at least one double or triple bond respectively. Suitable alkenyl and alkynyl groups include groups having 2 to about 12 carbon atoms, preferably from 1 to about 6 carbon atoms.

The term "alkyl" includes saturated aliphatic groups, including straight-chain alkyl groups, branched-chain alkyl groups, cycloalkyl (alicyclic) groups, alkyl substituted cycloalkyl groups and cycloalkyl substituted alkyl groups. In certain embodiments, a straight chain or branched chain alkyl has 30 or fewer carbon atoms in its backbone, e.g., C1-C30 for straight chain or C3-C30 for branched chain. In certain embodiments, a straight chain or branched chain alkyl has 20 or fewer carbon atoms in its backbone, e.g., C1-C20 for straight chain or C3-C20 for branched chain, and more preferably 18 or fewer. Likewise, preferred cycloalkyls have from 4-10 carbon atoms in their ring structure and more preferably have 4-7 carbon atoms in the ring structure. The term "lower alkyl" refers to alkyl groups having from 1 to 6 carbons in the chain and to cycloalkyls having from 3 to 6 carbons in the ring structure.

Moreover, the term "alkyl" (including "lower alkyl") as used throughout the specification and Claims includes both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfate, sulfonato, sulfamoyl, sulfonamido, nitro, trifluoromethyl, cyano, azido, heterocyclyl, aralkyl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "aralkyl" moiety is an alkyl substituted with an aryl, e.g., having 1 to 3 separate or fused rings and from 6 to about 18 carbon ring atoms, e.g., phenylmethyl (benzyl).

The term "amino," as used herein, refers to an unsubstituted or substituted moiety of the formula —NRaRb, in which Ra and Rb are each independently hydrogen, alkyl, aryl, or heterocyclyl, or Ra and Rb, taken together with the nitrogen atom to which they are attached, form a cyclic moiety having from 3 to 8 atoms in the ring. Thus, the term "amino" includes cyclic amino moieties such as piperidinyl or pyrrolidinyl groups, unless otherwise stated. An "aminosubstituted amino group" refers to an amino group in which at least one of Ra and Rb, is further substituted with an amino group.

The term "aromatic group" includes unsaturated cyclic hydrocarbons containing one or more rings. Aromatic groups include 5- and 6-membered single-ring groups which may include from zero to four heteroatoms, for example, benzene, pyrrole, furan, thiophene, imidazole, oxazole, thiazole, triazole, pyrazole, pyridine, pyrazine, pyridazine and pyrimidine and the like. The aromatic ring may be substituted at one or more ring positions with, for example, a halogen, a lower alkyl, a lower alkenyl, a lower alkoxy, a lower alkylthio, a lower alkylamino, a lower alkylcarboxyl, a nitro, a hydroxyl, —CF3, —CN, or the like.

The term "aryl" includes 5- and 6-membered single-ring aromatic groups that may include from zero to four heteroatoms, for example, unsubstituted or substituted benzene, pyrrole, furan, thiophene, imidazole, oxazole, thiazole, triazole, pyrazole, pyridine, pyrazine, pyridazine and pyrimidine and the like. Aryl groups also include polycyclic fused aromatic groups such as naphthyl, quinolyl, indolyl and the like. The aromatic ring can be substituted at one or more ring positions with such substituents, e.g., as described above for alkyl groups. Suitable aryl groups include unsubstituted and substituted phenyl groups. The term "aryloxy" as used herein means an aryl group, as defined above, having an oxygen atom attached thereto. The term "aralkoxy" as used herein means an aralkyl group, as defined above, having an oxygen atom attached thereto. Suitable aralkoxy groups have 1 to 3 separate or fused rings and from 6 to about 18 carbon ring atoms, e.g., O-benzyl.

The term "ceramic precursor" is intended include any compound that results in the formation of a ceramic material.

The term "chiral moiety" is intended to include any functionality that allows for chiral or stereoselective syntheses. Chiral moieties include, but are not limited to, substituent groups having at least one chiral center, natural and unnatural amino-acids, peptides and proteins, derivatized cellulose, macrocyclic antibiotics, cyclodextrins, crown ethers, and metal complexes.

The term "embedded polar functionality" is a functionality that provides an integral polar moiety such that the interaction with basic samples due to shielding of the unreacted silanol groups on the silica surface is reduced. Embedded polar functionalities include, but are not limited to carbonate, amide, urea, ether, thioether, sulfinyl, sulfoxide, sulfonyl, thiourea, thiocarbonate, thiocarbamate, ethylene glycol, heterocyclic, triazole functionalities or carbamate functionalities such as disclosed in U.S. Pat. No. 5,374,755, and chiral moieties.

The language "chromatographically-enhancing pore geometry" includes the geometry of the pore configuration of the presently-disclosed materials, which has been found to enhance the chromatographic separation ability of the material, e.g., as distinguished from other chromatographic media in the art. For example, a geometry can be formed, selected or constructed, and various properties and/or factors can be used to determine whether the chromatographic separations ability of the material has been "enhanced", e.g., as compared to a geometry known or conventionally used in the art. Examples of these factors include high separation efficiency, longer column life and high mass transfer properties (as evidenced by, e.g., reduced band spreading and good peak shape.) These properties can be measured or observed using art-recognized techniques. For example, the chromatographically-enhancing pore geometry of the present porous inorganic/organic hybrid materials is distinguished from the prior art materials by the absence of "ink bottle" or "shell shaped" pore geometry or morphology, both of which are undesirable because they, e.g., reduce mass transfer rates, leading to lower efficiencies.

Chromatographically-enhancing pore geometry is found in hybrid materials containing only a small population of micropores. A small population of micropores is achieved in hybrid materials when all pores of a diameter of about <34 Å contribute less than about 110 m$^2$/g to the specific surface area of the material. Hybrid materials with such a low micropore surface area (MSA) give chromatographic enhancements including high separation efficiency and good mass transfer properties (as evidenced by, e.g., reduced band spreading and good peak shape). Micropore surface area (MSA) is defined as the surface area in pores with diameters less than or equal to 34 Å, determined by multipoint nitrogen sorption analysis from the adsorption leg of the isotherm using the BJH method. As used herein, the acronyms "MSA" and "MPA" are used interchangeably to denote "micropore surface area".

The term "functionalizing group" includes organic functional groups which impart a certain chromatographic functionality to a chromatographic stationary phase.

The term "heterocyclic group" includes closed ring structures in which one or more of the atoms in the ring is an element other than carbon, for example, nitrogen, sulfur, or oxygen. Heterocyclic groups can be saturated or unsaturated and heterocyclic groups such as pyrrole and furan can have aromatic character. They include fused ring structures such as quinoline and isoquinoline. Other examples of heterocyclic groups include pyridine and purine. Heterocyclic groups can also be substituted at one or more constituent atoms with, for example, a halogen, a lower alkyl, a lower alkenyl, a lower alkoxy, a lower alkylthio, a lower alkylamino, a lower alkylcarboxyl, a nitro, a hydroxyl, —CF$_3$, —CN, or the like. Suitable heteroaromatic and heteroalicyclic groups generally will have 1 to 3 separate or fused rings with 3 to about 8 members per ring and one or more N, O or S atoms, e.g. coumarinyl, quinolinyl, pyridyl, pyrazinyl, pyrimidyl, furyl, pyrrolyl, thienyl, thiazolyl, oxazolyl, imidazolyl, indolyl, benzofuranyl, benzothiazolyl, tetrahydrofuranyl, tetrahydropyranyl, piperidinyl, morpholino and pyrrolidinyl.

The term "metal oxide precursor" is intended include any compound that contains a metal and results in the formation of a metal oxide, e.g., alumina, silica, titanium oxide, zirconium oxide.

The term "monolith" is intended to include a collection of individual particles packed into a bed formation, in which the shape and morphology of the individual particles are maintained. The particles are advantageously packed using a material that binds the particles together. Any number of binding materials that are well known in the art can be used such as, for example, linear or cross-linked polymers of divinylbenzene, methacrylate, urethanes, alkenes, alkynes, amines, amides, isocyanates, or epoxy groups, as well as condensation reactions of organoalkoxysilanes, tetraalkoxysilanes, polyorganoalkoxysiloxanes, polyethoxysiloxanes, and ceramic precursors. In certain embodiments, the term "monolith" also includes hybrid monoliths made by other methods, such as hybrid monoliths detailed in U.S. Pat. No. 7,250,214; hybrid monoliths prepared from the condensation of one or more monomers that contain 0-99 mole percent silica (e.g., SiO$_2$); hybrid monoliths prepared from coalesced porous inorganic/organic particles; hybrid monoliths that have a chromatographically-enhancing pore geometry; hybrid monoliths that do not have a chromatographically-enhancing pore geometry; hybrid monoliths that have ordered pore structure; hybrid monoliths that have non-periodic pore structure; hybrid monoliths that have non-crystalline or amorphous molecular ordering; hybrid monoliths that have crystalline domains or regions; hybrid monoliths with a variety of different macropore and mesopore properties; and hybrid monoliths in a variety of different aspect ratios. In certain embodiments, the term "monolith" also includes inorganic monoliths, such as those described in G. Guiochon/*J. Chromatogr. A* 1168 (2007) 101-168.

The term "nanoparticle" is a microscopic particle/grain or microscopic member of a powder/nanopowder with at least one dimension less than about 100 nm, e.g., a diameter or particle thickness of less than about 100 nm (0.1 mm), which may be crystalline or noncrystalline. Nanoparticles have properties different from, and often superior to those of conventional bulk materials including, for example, greater strength, hardness, ductility, sinterability, and greater reactivity among others. Considerable scientific study continues to be devoted to determining the properties of nanomaterials, small amounts of which have been synthesized (mainly as nano-size powders) by a number of processes including colloidal precipitation, mechanical grinding, and gas-phase nucleation and growth. Extensive reviews have documented recent developments in nano-phase materials, and are incorporated herein by reference thereto: Gleiter, H. (1989) "Nano-crystalline materials," Prog. Mater. Sci. 33:223-315 and Siegel, R. W. (1993) "Synthesis and properties of nano-phase materials," Mater. Sci. Eng. A168:189-197. In certain embodiments, the nanoparticles comprise oxides or nitrides of the following: silicon carbide, aluminum, diamond, cerium, carbon black, carbon nanotubes, zirconium, barium, cerium, cobalt, copper, europium, gadolinium, iron, nickel, samarium, silicon, silver, titanium, zinc, boron, and mixtures thereof. In certain embodiments, the nanoparticles of the present invention are selected from diamonds, zirconium oxide (amorphous, monoclinic, tetragonal and cubic forms), titanium oxide (amorphous, anatase, brookite and rutile forms), aluminum (amorphous, alpha, and gamma forms), and boronitride (cubic form). In particular embodiments, the nanoparticles of the present invention are selected from nano-diamonds, silicon carbide, titanium dioxide (anatase form), cubic-boronitride, and any combination thereof. Moreover, in particular embodiments, the nanoparticles may be crystalline or amorphous. In particular embodiments, the nanoparticles are less than or equal to 100 mm in diameter, e.g., less than or equal to 50 mm in diameter, e.g., less than or equal to 20 mm in diameter.

Moreover, it should be understood that the nanoparticles that are characterized as dispersed within the composites of the invention are intended to describe exogenously added nanoparticles. This is in contrast to nanoparticles, or formations containing significant similarity with putative nanoparticles, that are capable of formation in situ, wherein, for example, macromolecular structures, such as particles, may comprise an aggregation of these endogenously created.

The term "substantially disordered" refers to a lack of pore ordering based on x-ray powder diffraction analysis. Specifically, "substantially disordered" is defined by the lack of a peak at a diffraction angle that corresponds to a d value (or d-spacing) of at least 1 nm in an x-ray diffraction pattern.

"Surface modifiers" include (typically) organic functional groups which impart a certain chromatographic functionality to a chromatographic stationary phase. The porous inorganic/organic hybrid materials possess both organic groups and silanol groups which may additionally be substituted or derivatized with a surface modifier.

The language "surface modified" is used herein to describe the composite material of the present invention that possess both organic groups and silanol groups which may additionally be substituted or derivatized with a surface modifier. "Surface modifiers" include (typically) organic functional groups which impart a certain chromatographic functionality to a chromatographic stationary phase. Surface modifiers such as disclosed herein are attached to the base material, e.g., via derivatization or coating and later cross-linking, imparting the chemical character of the surface modifier to the base material. In one embodiment, the organic groups of a hybrid material, react to form an organic covalent bond with a surface modifier. The modifiers can form an organic covalent bond to the material's organic group via a number of mechanisms well known in organic and polymer chemistry including but not limited to nucleophilic, electrophilic, cycloaddition, free-radical, carbene, nitrene, and carbocation reactions. Organic covalent bonds are defined to involve the formation of a covalent bond between the common elements of organic chemistry including but not limited to hydrogen, boron, carbon, nitrogen, oxygen, silicon, phosphorus, sulfur, and the halogens. In addition, carbon-silicon and carbon-oxygen-silicon bonds are defined as organic covalent bonds, whereas silicon-oxygen-silicon bonds that are not defined as organic covalent bonds. A variety of synthetic transformations are well known in the literature, see, e.g., March, *J. Advanced Organic Chemistry*, 3rd Edition, Wiley, New York, 1985.

The term "macromolecule" includes polymers, e.g., oligomers, such as, e.g., DNA, RNA, proteins, lipids and polysaccharides, but excludes small organic molecules (typically having molecular weights of 500 Da or less). Exemplary macromolecules include peptides, phopshopeptides, polypeptides, glycopeptides, proteins, glycoproteins, antibodies, phosphoproteins, nucleic acids, oligonucleotoides, polynucleotides, phospholipids, synthetic or natural polymers and mixtures thereof. In certain embodiments, the macromolecule is not an insulin or a derivative thereof. In certain other embodiments, the protiens are enzymes, hormones, transport proteins, immunoglobulin or antibodies, structural proteins, motor proteins, receptor proteins, signalling proteins, storage proteins, or mixtures thereof.

The term "functionalized macromolecule" includes macromolecules having functional groups. Functionalized macromolecules are often referred to as "analytes of interest' in a variety of scientific, biochemical and clinical scenarios.

The term "functional group" refers to a specific structure of one or more atoms that is responsible for the chemical morphological, physiological, biochemical, or environmental behavior of a compound. One or more atoms, e.g., carbon and/or hydrogen atoms, of a macromolecule can be substituted with a functional group to yield a functionalized macromolecule. Thus, functionalized macromolecules accordingly have functional groups including, e.g., amines, carboxylic acids, phosphonates, sulfonates, sialylates, etc. Exemplary functionalized macromolecules in accordance with the invention include compounds containing highly acidic side chains or include a phosphate group, a sulfonate group, or a sialylate group.

Functionalized macromolecules according to the invention have functional groups that are distinct from other compounds found in a sample, e.g., a biological sample. For example, in a sample comprising phosphopeptides and natural peptides, the functionalized macromolecules are the phosphopeptides. Further examples of functionalized macromolecules include, but are not limited to, phosphopeptides, sialylated glycopeptides, sulfonated peptides, sulfonated peptides, sulfonated glycopeptides, phospho-oligonucleotides, and phospholipids. In certain embodiments, functionalized macromolecules include macromolecules having one or more isotopic labels. In certain other embodiments, the peptides or proteins are functionalized by myristoylation, palmitoylation, isoprenylation, farnesylation, geranylgeranylation, glypiation, glycosylphosphatidylinositol, lipoylation, flavin moiety attachment, heme attachment, phosphopantetheinylation, diphthamide formation, ethanolamine phosphoglycerol attachment, hypusine formation, acylation, acetylation, formylation, alkylation, methylation, amide bond formation, amino acid addition, arginylation, polyglutamylation, polyglycylation, butyrylation, carboxylation, glycosylation, glycation, polysialylation, malonylation, demethylation, hydroxylation, iodination, ribosylation, oxidation, phosphate ester, phosphoramidate formation, phosphorylation, adenylylation, propionylation, pyroglutamate formation, glutathionylation, nitrosylation, succinylation, sulfation, selenoylation, biotinylation, pegylation, ISGylation, SUMOylation, ubiquitination, Neddylation, Pupylation, citrullination, deimination, deamidation, eliminylation, dehydration, epoxidation, carbamylation, disulfide bridge formation, proteolytic cleavage, racemization, Click-group attachment, Michael addition attachment, Schiff base formation, or a mixture thereof.

The term "mother sample" includes any sample including one or more macromolecules, including, but not limited to, a sample derived from a biological fluid selected from the group consisting of blood, urine, spinal fluid, synovial fluid, sputum, semen, saliva, tears, gastric juices and extracts and/or dilutions/solutions thereof, which is subjected to chromatographic or other separation means prior to obtain a sample for isolation, separation, purification, or detection by the materials and methods of the invention.

The term "Chromatographic separations device" includes any device capable of performing a chromatographic separation, including, but not limited to, a chromatographic column, a thin layer plate, a filtration membrane, a microfluidic separation device, a sample cleanup device, a solid support, a solid phase extraction device, a microchip separation device, and a microtiter plate.

The term "secondary chromatographic separations means" includes chromatographic separations devices and chromatographic materials comprised by chromatographic separation devices. In certain embodiments, a secondary chromatographic separations means is a separate or additional chromatographic separation device than the chromatographic separations device utilized in the methods of the invention. In other embodiments, the secondary chromatographic separations means is a separate or additional chromatographic material housed by the same chromatographic separations device utilized in the methods of the invention.

Chromatographic Surface Materials

The invention provides, a high purity chromatographic material (HPCM) comprising a chromatographic surface wherein the chromatographic surface comprises a hydrophobic surface group and one or more ionizable modifiers with the proviso that when the ionizable modifier does not contain a Zwitterion, the ionizable modifier does not contain a quaternary ammonium ion moiety.

In certain aspects the HPCM may further comprise a chromatographic core material. In some aspects, the chromatographic core is a silica material; a hybrid inorganic/organic material; a superficially porous material; or a superficially porous particle. The chromatographic core material may be in the form of discreet particles or may be a monolith. The chromatographic core material may be any porous material and may be commercially available or may be produced by known methods, such as those methods described in, for example, in U.S. Pat. Nos. 4,017,528, 6,528,167, 6,686,035 and 7,175,913. In some embodiments, the chromatographic core material may be a non-porous core.

The composition of the chromatographic surface material and the chromatographic core material (if present) may be varied by one of ordinary skill in the art to provide enhanced chromatographic selectivity, enhanced column chemical stability, enhanced column efficiency, and/or enhanced mechanical strength. Similarly, the composition of the surrounding material provides a change in hydrophilic/lipophilic balance (HLB), surface charge (e.g., isoelectric point or silanol pKa), and/or surface functionality for enhanced chromatographic separation. Furthermore, in some embodiments, the composition of the chromatographic material may also provide a surface functionality for available for further surface modification.

The ionizable modifiers and the hydrophobic surface groups of the HPCMs of the invention can be prepared using known methods. Some of the ionizable modifier reagents are commercially available. For example silanes having amino alkyl trialkoxysilanes, methyl amino alkyl trialkoxysilanes, and pyridyl alkyl trialkoxysilanes are commercially available. Other silanes such as chloropropyl alkyl trichlorosilane and chloropropyl alkyl trialkoxysilane are also commercially available. These can be bonded and reacted with imidazole to create imidazolyl alkyl silyl surface species, or bonded and reacted with pyridine to create pyridyl alkyl silyl surface species. Other acidic modifiers are also commercially available, including, but not limited to, sulfopropyl-trisilanol, carboxyethylsilanetriol, 2-(carbomethoxy)ethylmethyldichlorosilane, 2-(carbomethoxy)ethyltrichlorosilane, 2-(carbomethoxy)ethyltrimethoxysilane, n-(trimethoxysilylpropyl)ethylenediamine, triacetic acid, (2-diethylphosphatoethyl)triethoxysilane, 2-(chlorosulfonylphenyl)ethyltrichlorosilane, and 2-(chlorosulfonylphenyl)ethyltrimethoxysilane.

It is known to one skilled in the art to synthesize these types of silanes using common synthetic protocols, including Grinard reactions and hydrosilylations. Products can be purified by chromatography, recrystallization or distillation Other additives such as isocyanates are also commercially available or can be synthesized by one skilled in the art. A common isocyanate forming protocol is the reaction of a primary amine with phosgene or a reagent known as Triphosgene.

In some embodiments the ionizable modifier contains a carboxylic acid group, a sulfonic acid group, a phosphoric acid group, a boronic acid group, an amino group, an imido group, an amido group, a pyridyl group, an imidazolyl group, an ureido group, a thionyl-ureido group or an aminosilane group.

In other aspects the ionizable modifier reagent may be selected from groups formula (I)

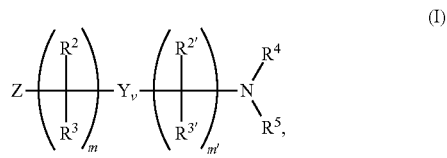

the formula (II):

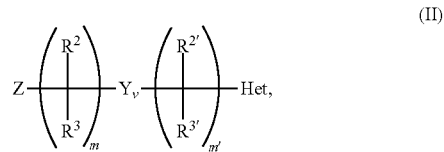

the formula (IR):

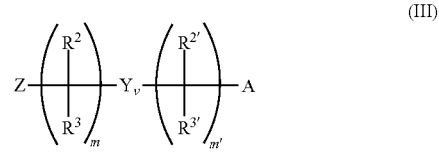

wherein
m is an integer from 1-8;
v is 0 or 1;
when v is 0, m' is 0;
when v is 1, m' is an integer from 1-8;
Z represents a chemically reactive group, including (but not limited to)

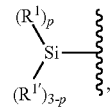

—OH, —OR$^6$, amine, alkylamine, dialkylamine, isocyanate, acyl chloride, triflate, isocyanate, thiocyanate, imidazole carbonate, NHS-ester, carboxylic acid, ester, epoxide, alkyne, alkene, azide, —Br, —Cl, or —I;
Y is an embedded polar functionality;
each occurrence of R$^1$ independently represents a chemically reactive group on silicon, including (but not limited to) —H, —OH, —OR$^6$, dialkylamine, triflate, Br, Cl, I, vinyl, alkene, or —(CH$_2$)$_{m'}$Q;

each occurrence of Q is —OH, —OR$^6$, amine, alkylamine, dialkylamine, isocyanate, acyl chloride, triflate, isocyanate, thiocyanate, imidazole carbonate, NHS-ester, carboxylic acid, ester, epoxide, alkyne, alkene, azide, —Br, —Cl, or —I;

m" is an integer from 1-8 p is an integer from 1-3;

each occurrence of $R^{1'}$ independently represents F, $C_1$-$C_{18}$ alkyl, $C_2$-$C_{18}$ alkenyl, $C_2$-$C_{18}$ alkynyl, $C_3$-$C_{18}$ cycloalkyl, $C_1$-$C_{18}$ heterocycloalkyl, $C_5$-$C_{18}$ aryl, $C_5$-$C_{18}$ aryloxy, or $C_1$-$C_{18}$ heteroaryl, fluoroalkyl, or fluoroaryl;

each occurrence of $R^2$, $R^{2'}$, $R^3$ and $R^{3'}$ independently represents hydrogen, $C_1$-$C_{18}$ alkyl, $C_2$-$C_{18}$ alkenyl, $C_2$-$C_{18}$ alkynyl, $C_3$-$C_{18}$ cycloalkyl, $C_2$-$C_{18}$ heterocycloalkyl, $C_5$-$C_{18}$ aryl, $C_5$-$C_{18}$ aryloxy, or $C_4$-$C_{18}$ heteroaryl, —Z, or a group having the formula —Si(R')$_b$R"$_a$ or —C(R')$_b$R"$_a$;

a and b each represents an integer from 0 to 3 provided that a+b=3;

R' represents a $C_1$-$C_6$ straight, cyclic or branched alkyl group;

R" is a functionalizing group selected from the group consisting of alkyl, alkenyl, alkynyl, aryl, cyano, amino, diol, nitro, ester, a cation or anion exchange group, an alkyl or aryl group containing an embedded polar functionality and a chiral moiety.

$R^4$ represents hydrogen, $C_1$-$C_{18}$ alkyl, $C_2$-$C_{18}$ alkenyl, $C_2$-$C_{18}$ alkynyl, $C_3$-$C_{18}$ cycloalkyl, $C_1$-$C_{18}$ heterocycloalkyl, $C_5$-$C_{18}$ aryl, $C_5$-$C_{18}$ aryloxy, or $C_1$-$C_{18}$ heteroaryl;

$R^5$ represents hydrogen, $C_1$-$C_{18}$ alkyl, $C_2$-$C_{18}$ alkenyl, $C_2$-$C_{18}$ alkynyl, $C_3$-$C_{18}$ cycloalkyl, $C_1$-$C_{18}$ heterocycloalkyl, $C_5$-$C_{18}$ aryl, $C_5$-$C_{18}$ aryloxy, or $C_1$-$C_{18}$ heteroaryl;

each occurrence of $R^6$ independently represents $C_1$-$C_{18}$ alkyl, $C_2$-$C_{18}$ alkenyl, $C_2$-$C_{18}$ alkynyl, $C_3$-$C_{18}$ cycloalkyl, $C_1$-$C_{18}$ heterocycloalkyl, $C_5$-$C_{18}$ aryl, $C_5$-$C_{18}$ aryloxy, or $C_1$-$C_{18}$ heteroaryl;

Het represents a heterocyclic or heteroaryl ring system comprising at least one nitrogen atom; and A represents an acidic ionizable modifier moiety or a dual charge ionizable modifier moiety.

In yet other embodiments, the inoizable modifier is aminopropyltriethoxysilane, aminopropyltrimethoxysilane, 2-(2-(trichlorosilyl)ethyl)pyridine, 2-(2-(trimethoxy)ethyl)pyridine, 2-(2-(triethoxy)ethyl)pyridine, 2-(4-pyridylethyl)triethoxysilane, 2-(4-pyridylethyl)trimethoxysilane, 2-(4-pyridylethyl)trichlorosilane, chloropropyltrimethoxysilane, chloropropyltrichlorosilane, chloropropyltrichlorosilane, chloropropyltriethoxysilane, imidazolylpropyltrimethoxysilane, imidazolylpropyltriethoxysilane, imidazolylpropyltrichlorosilane, sulfopropyltrisilanol, carboxyethylsilanetriol, 2-(carbomethoxy)ethylmethyldichlorosilane, 2-(carbomethoxy)ethyltrichlorosilane, 2-(carbomethoxy)ethyltrimethoxysilane, n-(trimethoxysilylpropyl)ethylenediamine triacetic acid, (2-diethylphosphatoethyl)triethoxysilane, 3-mercaptopropyltriethoxysilane, 3-mercaptopropyltrimethoxysilane, bis[3-(triethoxysilyl)propyl]disulfide, bis[3-(triethoxysilyl)propyl]tetrasulfide, 2,2-dimethoxy-1-thia-2-silacyclopentane, bis(trichlorosilylethyl)phenylsulfonyl chloride, 2-(chlorosulfonylphenyl)ethyltrichlorosilane, 2-(chlorosulfonylphenyl)ethyltrimethoxysilane, 2-(ethoxysulfonylphenyl)ethyltrimethoxysilane, 2-(ethoxysulfonylphenyl)ethyltrimethoxysilane, 2-(ethoxysulfonylphenyl)ethyltrichlorosilane, sulphonic acid phenethyltrisilanol, (triethoxysilyl ethyl)phenyl phosphonic acid diethyl ester, (trimethoxysilyl ethyl)phenyl phosphonic acid diethyl ester, (trichlorosilyl ethyl)phenyl phosphonic acid diethyl ester, phosphonic acid phenethyltrisilanol, N-(3-trimethoxysilylpropyl)pyrrole, N-(3-triethoxysilylpropyl)-4,5-dihydroimidazole, bis(methyldimethoxysilylpropyl)-N-methylamine, tris(triethoxysilylpropyl)amine, bis(3-trimethoxysilylpropyl)-N-methylamine, (N,N-diethyl-3-aminopropyl)trimethoxysilane, N-(hydroxyethyl)-N-methylaminopropyltrimethoxysilane, 3-(N,N-dimethylaminopropyl)trimethoxysilane, bis(2-hydroxyethyl)-3-aminopropyltriethoxysilane, N,N'-bis(hydroxyethyl)-N,N'-bis(trimethoxysilylpropypethylenediamine, or N,N-dimethyl-3-aminopropylmethyldimethoxysilane.

In certain embodiments, when the ionizable modifier is of the formula the acidic ionizable modifiers is a protected or deprotected forms of trisilanol, trialkoxysilane or trichlorosilane; or a salt of sulfonic acid alkyl silanes, sulfonic acid phenylalkyl silanes, sulfonic acid benzylalkyl silanes, sulfonic acid phenyl silanes, sulfonic acid benzyl silanes, carboxylic acid alkyl silanes, carboxylic acid phenylalkyl silanes, carboxylic acid benzylalkyl silanes, carboxylic acid phenyl silanes, carboxylic acid benzyl silanes, phosphoric acid alkyl silanes, phosphonic acid phenylalkyl silanes, phosphonic acid benzylalkyl silanes, phosphonic acid phenyl silanes, phosphonic acid benzyl silanes, boronic acid alkyl silanes, boronic acid phenylalkyl silanes, boronic acid benzylalkyl silanes, boronic acid phenyl silanes, boronic acid benzyl silanes.

In certain embodiments, when the ionizable modifier is of the formula (IH), the acidic ionizable modifiers is a protected or deprotected version or a salt of sulfonic acid alkyl isocyanates, sulfonic acid phenylalkyl isocyanates, sulfonic acid benzylalkyl isocyanates, sulfonic acid phenyl isocyanates, sulfonic acid benzyl isocyanates carboxylic acid alkyl isocyanates, carboxylic acid phenylalkyl isocyanates, carboxylic acid benzylalkyl isocyanates, carboxylic acid phenyl isocyanates, carboxylic acid benzyl isocyanates, phosphoric acid alkyl isocyanates, phosphonic acid phenylalkyl isocyanates, phosphonic acid benzylalkyl isocyanates, phosphonic acid phenyl isocyanates, phosphonic acid benzyl isocyanates, boronic acid alkyl isocyanates, boronic acid phenylalkyl isocyanates, boronic acid benzylalkyl isocyanates, boronic acid phenyl isocyanates, or boronic acid benzyl isocyanates.

In certain embodiments, when the inoizable modifier reagent is selected from formula (II), A represents a dual charge ionizable modifier moiety. While not limited to theory; the dual charge ionizable modifier moiety has two sub-groups that can display opposite charges. Under some conditions the dual charge ionizable modifier moiety can act similarly to a zwitterions and ampholytes to display both a positive and negative charge and maintain a zero net charge. Under other conditions the dual charge ionizable modifier moiety may only have one group ionized and may display a net positive or negative charge. Dual charge ionizable modifier moieties include, but are not limited to, alkyl, branched alkyl, aryl, cyclic, polyaromatic, polycyclic, hertocyclic and polyheterocyclic groups that can display a positive charge (commonly on a nitrogen or oxygen atom), and a negative charge through an acidic group that includes a carboxylic, sulfonic, phosphonic or boronic acid. Alternatively, some metal containing complexes can display both positive and negative charges. Dual charge ionizable modifier moieties may also include, but are not limited to zwitterions, ampholyte, amino acid, aminoalkyl sulfonic acid, aminoalkyl carboxylic acid, mono and di-methylaminoalkyl sulfonic acid, mono and di-methylaminoalkyl carboxylic acid, pyridinium alkyl sulfonic acid, and pyridinium alkyl carboxylic acid groups. Alternatively the dual charge ionizable modifier moiety may be 2-(N-morpholino)ethanesulfonic acid, 3-(N-morpholino)propanesulfonic acid, 4-(2-hydroxyethyl)-1- piperazine ethanesulfonic acid), piperazine-N,N'-bis(2-ethanesulfonic acid), N-cyclohexyl-3-aminopropanesulfonic acid, N-cyclohexyl-2 hydroxyl-3-aminopropanesulfonic acid, 3-[(3-cholamidopropyl)dimethylammonio]-1-propanesulfonate, 6-Methyl-9,10-didehydro-ergoline-8-carboxylic acid, phenolsulfonphthalein, betaines, quinonoids, N,N-bis(2-hydroxyethyl)glycine, and N—[tris(hydroxymethyl)methyl]glycine groups.

In some embodiments, the ratio of the hydrophobic surface group:ionizable modifier in the HPCM of the invention is from about 4:1 to about 150:1; from about 20:1 to about 100:1; or from about 25:1 to about 100:1.

In other embodiments, the concentration of ionizable modifier in the HPCM of the invention is less than about 0.5 µmol/m$^2$; less than about 0.4 µmol/m$^2$; less than about 0.3 µmol/m$^2$; from about 0.01 µmol/m$^2$ to about 0.5 µmol/m$^2$; from about 0.1 µmol/m$^2$ to about 0.4 µmol/m$^2$; or from about 0.2 µmol/m$^2$ to about 0.3 µmol/m$^2$.

In still another aspect, the HPCM of the invention has a quantified surface coverage ratio, B/A, from about 2.5 to about 300 wherein A represents the ionizable modifier and B represents the hydrophobic group. In certain aspects, the quantified surface coverage ratio, B/A, is from about 3 to about 200, from about 4 to about 35 or from about 5 to about 22.

In another aspect, the hydrophobic surface group of the HPCM of the invention is a C4 to C18 bonded phase. In certain aspects, the hydrophobic surface group is a C18 bonded phase. In still other aspects, the hydrophobic surface group is an embedded polar bonded phase. In other aspects, the hydrophobic surface group is an aromatic, phenylalkyl, fluoro-aromatic, phenylhexyl, or pentafluorophenylalkyl bonded phase. In another aspect, the hydrophobic surface group is a $C_4$-$C_{30}$, embedded polar, chiral, phenylalkyl, or pentafluorophenyl bonding or coating.

In certain embodiments, the HPCM of the invention may be in the form of a particle, a monolith or a superficially porous material. In certain other aspects, the HPCM of the invention is a non-porous material.

In certain aspects, the HPCM of the invention may be an inorganic material (e.g., silica,), a hybrid organic/inorganic material, an inorganic material (e.g., silica) with a hybrid surface layer, a hybrid particle with a inorganic (e.g., silica) surface layer, or a hybrid particle with a different hybrid surface layer.

In one embodiment, the HPCM of the invention does not have chromatographically enhancing pore geometry. In another embodiment, the HPCM of the invention has chromatographically enhancing pore geometry.

In certain embodiments, the HPCM of the invention has a surface area of about 25 to 1100 m$^2$/g; about 80 to 500 m$^2$/g; or about 120 to 330 m$^2$/g.

In other embodiments, the HPCM of the invention a pore volume of about 0.15 to 1.7 cm$^3$/g; or about 0.5 to 1.3 cm$^3$/g.

In certain other embodiments, the HPCM of the invention is non-porous.

In yet other embodiments, the HPCM of the invention has a micropore surface area of less than about 110 m$^2$/g; less than about 105 m$^2$/g; less than about 80 m$^2$/g; or less than about 50 m$^2$/g.

In still yet other embodiments, the HPCM of the invention has an average pore diameter of about 20 to 1500 Å; about 50 to 1000 Å; about 100 to 750 Å; or about 150 to 500 Å.

In another embodiment, the HPCM of the invention is hydrolytically stable at a pH of about 1 to about 14; at a pH of about 10 to about 14; or at a pH of about 1 to about 5.

In another aspect, the invention provides materials as described herein wherein the HPCM material further comprises a nanoparticle or a mixture of more than one nanoparticles dispersed within the chromatographic surface.

In certain embodiments, the nanoparticle is present in <20% by weight of the nanocomposite, <10% by weight of the nanocomposite, or <5% by weight of the nanocomposite.

In other embodiments, the nanoparticle is crystalline or amorphous and may be silicon carbide, aluminum, diamond, cerium, carbon black, carbon nanotubes, zirconium, barium, cerium, cobalt, copper, europium, gadolinium, iron, nickel, samarium, silicon, silver, titanium, zinc, boron, oxides thereof, or a nitride thereof. In particular embodiments, the nanoparticle is a substance which comprises one or more moieties selected from the group consisting of nano-diamonds, silicon carbide, titanium dioxide, and cubic-boronitride.

In other embodiments, the nanoparticles may be less than or equal to 200 nm in diameter, less than or equal to 100 nm in diameter, less than or equal to 50 nm in diameter, or less than or equal to 20 nm in diameter.

Surface Modification

The HPCM materials of the invention may further be surface modified.

Thus, in one embodiment, the material as described herein may be surface modified with a surface modifier having the formula $Z_a(R')_b Si$—R", where Z=Cl, Br, I, C1-C5 alkoxy, dialkylamino or trifluoromethanesulfonate; a and b are each an integer from 0 to 3 provided that a+b=3; R' is a $C_1$-$C_6$ straight, cyclic or branched alkyl group, and R" is a functionalizing group.

In another embodiment, the materials have been surface modified by coating with a polymer.

In certain embodiments, R' is selected from the group consisting of methyl, ethyl, propyl, isopropyl, butyl, t-butyl, sec-butyl, pentyl, isopentyl, hexyl and cyclohexyl. In other embodiments, R' is selected from the group consisting of alkyl, alkenyl, alkynyl, aryl, cyano, amino, diol, nitro, ester, a cation or anion exchange group, an alkyl or aryl group containing an embedded polar functionality and a chiral moiety. In certain embodiments, R' is selected from the group consisting of aromatic, phenylalkyl, fluoroaromatic, phenylhexyl, pentafluorophenylalkyl and chiral moieties.

In one embodiment, R" is a $C_1$-$C_{30}$ alkyl group. In a further embodiment, R" comprises a chiral moiety. In another further embodiment, R" is a $C_1$-$C_{20}$ alkyl group.

In certain embodiments, the surface modifier comprises an embedded polar functionality. In certain embodiments, such embedded polar functionality includes carbonate, amide, urea, ether, thioether, sulfinyl, sulfoxide, sulfonyl, thiourea, thiocarbonate, thiocarbamate, ethylene glycol, heterocyclic, or triazole functionalities. In other embodiments, such embedded polar functionality includes carbamate functionalities such as disclosed in U.S. Pat. No. 5,374,755, and chiral moieties. Such groups include those of the general formula

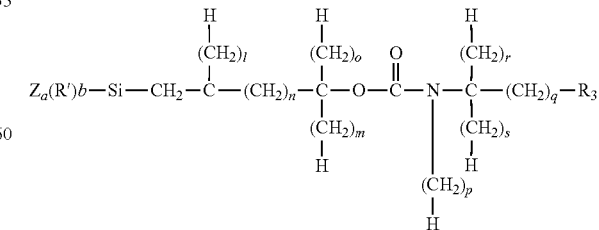

wherein l, m, o, r and s are 0 or 1, n is 0, 1, 2 or 3 p is 0, 1, 2, 3 or 4 and q is an integer from 0 to 19; $R_3$ is selected from the group consisting of hydrogen, alkyl, cyano and phenyl; and Z, R', a and b are defined as above. Preferably, the carbamate functionality has the general structure indicated below:

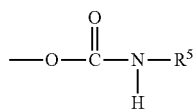

wherein $R^5$ may be, e.g., cyanoalkyl, t-butyl, butyl, octyl, dodecyl, tetradecyl, octadecyl, or benzyl. Advantageously, $R^5$ is octyl, dodecyl, or octadecyl.

In certain embodiments, the surface modifier is selected from the group consisting of phenylhexyltrichlorosilane, pentafluorophenylpropyltrichlorosilane, octyltrichlorosilane, octadecyltrichlorosilane, octyldimethylchlorosilane and octadecyldimethylchlorosilane. In some embodiments, the surface modifier is selected from the group consisting of octyltrichlorosilane and octadecyltrichlorosilane. In other embodiments, the surface modifier is selected from the group consisting of an isocyanate or 1,1'-carbonyldiimidazole (particularly when the hybrid group contains a $(CH_2)_3OH$ group).

In another embodiment, the material has been surface modified by a combination of organic group and silanol group modification.

In still another embodiment, the material has been surface modified by a combination of organic group modification and coating with a polymer. In a further embodiment, the organic group comprises a chiral moiety.

In yet another embodiment, the material has been surface modified by a combination of silanol group modification and coating with a polymer.

In other embodiments, the material has been surface modified via formation of an organic covalent bond between the particle's organic group and the modifying reagent.

In still other embodiments, the material has been surface modified by a combination of organic group modification, silanol group modification and coating with a polymer.

In another embodiment, the material has been surface modified by silanol group modification.

In certain embodiments, the surface modified layer may be porous or non-porous.

Separation Devices and Kits and Methods of Use

Another aspect provides a variety of separations devices having a stationary phase comprising the HPCM materials as described herein. The separations devices include, e.g., chromatographic columns, thin layer plates, filtration membranes, sample cleanup devices and microtiter plates.

The HPCM Materials impart to these devices improved lifetimes because of their improved stability. Thus, in a particular aspect, the invention provides a chromatographic column having improved lifetime, comprising
   a) a column having a cylindrical interior for accepting a packing material, and
   b) a packed chromatographic bed comprising the high purity chromatographic material as described herein.

In another particular aspect, the invention provides a chromatographic device, comprising
   a) an interior channel for accepting a packing material and
   b) a packed chromatographic bed comprising the high purity chromatographic material as described herein.

The invention also provides for a kit comprising the HPCM materials as described herein, as described herein, and instructions for use. In one embodiment, the instructions are for use with a separations device, e.g., chromatographic columns, thin layer plates, filtration membranes, sample cleanup devices and microtiter plates. In another embodiment, the instructions are for the separation, isolation, purification, or detection of one or more macromolecules, e.g., peptides, polypeptides, and small protiens.

The invention provides methods for selectively isolating/separating, purifying, detecting and/or analyzing a macromolecule or mixture of macromolecules using sthe HPCM materials as described herein. The methods of the invention are capable of separating and thereby resolving complex mixtures of compounds, allowing rapid isolation/separation, purification, detection and/or analysis of component compounds of such mixtures.

In one aspect the invention provides a method for selectively isolating a macromolecule from a sample, the method comprising the steps of:
   a) loading a sample containing a macromolecule onto a chromatographic separations device comprising a high purity chromatographic material comprising a chromatographic surface wherein the chromatographic surface comprises a hydrophobic surface group and one or more ionizable modifiers with the proviso that when the ionizable modifier does not contain a Zwitterion, the ionizable modifier does not contain a quaternary ammonium ion moiety such that the macromolecule is selectively adsorbed onto the high purity chromatographic material; and
   b) eluting the adsorbed macromolecule from the high purity chromatographic material, thereby selectively isolating the macromolecule from the sample.

In still another aspect, the invention provides a method for separating a plurality of macromolecules from a sample, the method comprising the steps of:
   a) loading a sample containing a plurality of macromolecules onto chromatographic separations device comprising a high purity chromatographic material comprising a chromatographic surface wherein the chromatographic surface comprises a hydrophobic surface group and one or more ionizable modifiers with the proviso that when the ionizable modifier does not contain a Zwitterion, the ionizable modifier does not contain a quaternary ammonium ion moiety such that the macromolecules are adsorbed onto the high purity chromatographic material; and
   b) eluting the adsorbed macromolecules from the high purity chromatographic material, thereby separating the macromolecules.

In yet another aspect, the invention provides a method for purifying a macromolecule contained in a sample, the method comprising the steps of:
   a) loading a sample containing a macromolecule onto chromatographic separations device comprising a high purity chromatographic material comprising a chromatographic surface wherein the chromatographic surface comprises a hydrophobic surface group and one or more ionizable modifiers with the proviso that when the ionizable modifier does not contain a Zwitterion, the ionizable modifier does not contain a quaternary ammonium ion moiety such that the macromolecule are adsorbed onto the high purity chromatographic material; and
   b) eluting the adsorbed macromolecule from the high purity chromatographic material, thereby purifying a macromolecule.

In still yet another aspect, the invention provides a method for detecting a macromolecule in a sample, the method comprising the steps of:
a) loading a sample containing a macromolecule onto chromatographic separations device comprising a high purity chromatographic material comprising a chromatographic surface wherein the chromatographic surface comprises a hydrophobic surface group and one or more ionizable modifiers with the proviso that when the ionizable modifier does not contain a Zwitterion, the ionizable modifier does not contain a quaternary ammonium ion moiety such that the macromolecules are adsorbed onto the high purity chromatographic material; and
b) eluting the adsorbed macromolecule from the high purity chromatographic material; and
c) detecting the macromolecule.

In certain aspects of the chromatographic methods of the invention, the macromolecule is selected from the group consisting of a peptide, a polypeptide, a phosphopeptide, a glycopeptide, a protein, a phosphoprotein, a nucleic acid, an oligonucleotide, a polynucleotide, a phospholipid, a synthetic or natural polymer, a functionalized macromolecule, and mixtures thereof.

Insofar as the target substance, i.e., the macromolecule, is concerned, the methods of the invention work well on polar compounds, non-polar compounds, acidic compounds, neutral compounds, basic compounds and any mixtures thereof. Thus, the macromolecules present in sample can be, e.g., peptides, phosphopeptides, polypeptides, proteins, or phosphoproteins (arising from, e.g., peptide synthesis or from biological samples, including digests of proteins or mixtures of proteins), nucleic acids, oligonucleotides or polynucleotides (e.g., from biological samples or from synthesized polynucleotides), phosopholipids, synthetic or natural polymers, or mixtures of these materials. The methods and systems of the invention are particularly advantageous in separating peptides, in particular, phosphopeptides, phospholipids and oligonucleotides.

In certain embodiments, the macromolecule is a macromolecule selected from the group consisting of a peptide, a polypeptide, a phosphopeptide, a glycopeptide, a protein, a phosphoprotein, a nucleic acid, an oligonucletoide, a polynucleotide, a phospholipid, a synthetic or natural polymer and mixtures thereof.

In one embodiment the macromolecule is selected from a peptide, phosphopeptide, polypeptide, protein, oligonucleotide, and phospholipid. In another embodiment, the macromolecule is a phosphopeptide. In another embodiment, the macromolecule is an oligonucleotide. In still another embodiment, the macromolecule is a phospholipid.

In particular embodiments, the macromolecule is a peptide, polypeptide, or protein comprising a highly acidic side chain. In other embodiments, the peptide, polypeptide or protein comprises a phosphate group, a sulfonate group or a sialylate group.

In still another embodiment, the macromolecule is a phosphopeptide, sialylated glycopeptide, sulfonated peptide or sulfonated glycopeptide.

In a specific embodiment, the peptide is a phosphopeptide.

In a specific embodiment, the macromolecule is not insulin or a derivative thereof.

In another specific embodiment, the macromolecule is an oligonucleotide. In yet another specific embodiment, the macromolecule is a phospholipid.

In certain embodiments, the peptide, polypeptide, or protein is selectively isolated over an acidic peptide, a neutral peptide, or a basic peptide. In a particular embodiment, the peptide, polypeptide, or protein is selectively isolated over an acidic peptide.

The methods of the invention can be used to selectively isolate, purify and/or detect macromolecules from a variety of samples. In one embodiment, the sample is or is derived from a biological fluid selected from the group consisting of blood, urine, spinal fluid, synovial fluid, sputum, semen, saliva, tears, gastric juices and extracts and/or dilutions/solutions thereof. In certain embodiments, the sample comprises a biological mixture of compounds.

In certain embodiments, the materials of the invention are found to produce significantly improved peak shape as compared to traditional chromatographic materials which do not utilize a charged surface. Furthermore, the materials of the invention are found to mitigate non-specific binding issues associated with traditional chromatographic materials which do not utilize a charged surface. Such benefits, in particular, allow for the identification or confirmation by Mass Spectrometry of low abundant macromolecules because they are not lost to non-specific binding and are not obscured by the degraded peak shapes that have been shown for abundant species, with traditional chromatographic materials, with the increase in sample mass needed to see the low abundant species.

Synthesis of Materials of the Invention

The invention also provides methods for producing the high purity chromatographic materials (HPCM) materials described herein.

In one embodiment, the invention provides a method for producing the HPCM described herein comprising the steps of:
a. reacting a chromatographic core with an ionizable modifying reagent to obtain a ionizable modified material; and
b. reacting the resultant material with a hydrophobic surface modifying group.

In another embodiment, the invention provides a method for producing the High purity chromatographic materials described herein comprising the steps of:
a. reacting a chromatographic core with hydrophobic surface modifying group to obtain a surface modified material; and
b. reacting the resultant material with an ionizable modifying reagent.

In another embodiment, the invention provides a method for producing the High purity chromatographic materials described herein comprising the steps of:
a. reacting a chromatographic core with hydrophobic surface modifying group to obtain a surface modified material; and
b. reacting the resultant material with an endcapping surface group, and
c. reacting the resultant material with an ionizable modifying reagent.

In another embodiment, the invention provides a method for producing the High purity chromatographic materials described here comprising the steps of:
a. reacting a chromatographic core with an ionizable modifying reagent to obtain an ionizable modified material; and
b. reacting the resultant material to produce a hybrid surface layer; and
c. reacting the resultant material with a hydrophobic surface modifying group.

In one aspect, the HPCM of the invention as described above is made with a charge ratio, B'/A', from about 3 to about 133 wherein A' represents the ionizable modifier reagent charged in the preparation and B' represents the hydrophobic group charged in the preparation. In certain aspects, the charge ratio, B'/A', is from about 4 to about 80, from about 4 to about 15, or from about 6 to about 7.

In one embodiment, the methods described herein further comprise the step of endcapping remaining silanol groups.

In one embodiment, in the methods described the steps are performed simultaneously.

In another embodiment, the pore structure of the as-prepared high purity chromatographic materials us modified by hydrothermal treatment, which enlarges the openings of the pores as well as the pore diameters, as confirmed by nitrogen ($N_2$) sorption analysis. The hydrothermal treatment is performed by preparing a slurry containing the as-prepared hybrid material and a solution of a base in water, heating the slurry in an autoclave at an elevated temperature, e.g., 100 to 200° C., for a period of 10 to 30 h. The use of an alkyl amine such as trimethylamine (TEA) or Tris(hydroxymethyl) methyl amine or the use of sodium hydroxide is advantageous. The thus-treated material is cooled, filtered and washed with water and methanol, then dried at 80° C. under reduced pressure for 16 h.

In certain embodiments, following hydrothermal treatment, the surfaces of the high purity chromatographic materials are modified with various agents. Such "surface modifiers" include (typically) organic functional groups which impart a certain chromatographic functionality to a chromatographic stationary phase. In certain aspects, when the HPCM is a hybrid material, it possesses possess both organic groups and silanol groups which may additionally be substituted or derivatized with a surface modifier.

The surface of the hydrothermally treated high purity chromatographic materials contains organic groups, which can be derivatized by reacting with a reagent that is reactive towards the materials' organic group. For example, vinyl groups on the material can be reacted with a variety of olefin reactive reagents such as bromine ($Br_2$), hydrogen ($H_2$), free radicals, propagating polymer radical centers, dienes and the like. In another example, hydroxyl groups on the material can be reacted with a variety of alcohol reactive reagents such as isocyanates, carboxylic acids, carboxylic acid chlorides and reactive organosilanes as described below. Reactions of this type are well known in the literature, see, e.g., March, J. *Advanced Organic Chemistry*, 3$^{rd}$ Edition, Wiley, New York, 1985; Odian, G. *The Principles of Polymerization*, 2$^{nd}$ Edition, Wiley, New York, 1981.

In addition, the surface of the hydrothermally treated high purity chromatographic materials also contains silanol groups, which can be derivatized by reacting with a reactive organosilane. The surface derivatization of the high purity chromatographic materials is conducted according to standard methods, for example by reaction with octadecyltrichlorosilane or octadecyldimethylchlorosilane in an organic solvent under reflux conditions. An organic solvent such as toluene is typically used for this reaction. An organic base such as pyridine or imidazole is added to the reaction mixture to catalyze the reaction. The product of this reaction is then washed with water, toluene and acetone. This material can be further treated by hydrolysis in a pH modified aqueous organic solution at ambient or elevated temperatures. An organic solvent such as acetone is typically used for this hydrolysis. Modification of pH can be achieved using acid or base modifiers, including trifluoroacetic acid, formic acid, hydrochloric acid, acetic acid, sodium or ammonium formate, sodium, potassium or ammonium acetate, phosphate buffers, ammonium hydroxide, ammonium carbonate, or ammonium bicarbonate. The product of the hydrolysis is then washed with water, toluene and acetone and dried at 80° C. to 100° C. under reduced pressure for 16 h. The resultant materials can be further reacted with a short-chain silane such as trimethylchlorosilane to endcap the remaining silanol groups, by using a similar procedure described above.

Surface modifiers such as disclosed herein are attached to the base material, e.g., via derivatization or coating and later crosslinking, imparting the chemical character of the surface modifier to the base material. In one embodiment, the organic groups of the high purity chromatographic materials react to form an organic covalent bond with a surface modifier. The modifiers can form an organic covalent bond to the materials organic group via a number of mechanisms well known in organic and polymer chemistry including but not limited to nucleophilic, electrophilic, cycloaddition, free-radical, carbene, nitrene and carbocation reactions. Organic covalent bonds are defined to involve the formation of a covalent bond between the common elements of organic chemistry including but not limited to hydrogen, boron, carbon, nitrogen, oxygen, silicon, phosphorus, sulfur and the halogens. In addition, carbon-silicon and carbon-oxygen-silicon bonds are defined as organic covalent bonds, whereas silicon-oxygen-silicon bonds that are not defined as organic covalent bonds.

The term "functionalizing group" includes organic functional groups which impart a certain chromatographic functionality to a chromatographic stationary phase, including, e.g., octadecyl (C18) or phenyl. Such functionalizing groups are incorporated into base material directly, or present in, e.g., surface modifiers such as disclosed herein which are attached to the base material, e.g., via derivatization or coating and later crosslinking, imparting the chemical character of the surface modifier to the base material.

In certain embodiments, silanol groups are surface modified. In other embodiments, organic groups are surface modified. In still other embodiments, the high purity chromatographic materials' organic groups and silanol groups are both surface modified or derivatized. In another embodiment, the high purity chromatographic materials are surface modified by coating with a polymer. In certain embodiments, surface modification by coating with a polymer is used in conjunction with silanol group modification, organic group modification, or both silanol and organic group modification. The ionizable modifier may be added to the material by silanol group modification, organic group modification, or by both silanol and organic group modification. The hydrophobic surface group may be added to the material by silanol group modification, organic group modification, or by both silanol and organic group modification.

More generally, the surface of high purity chromatographic materials may be modified by: treatment with surface modifiers including compounds of formula $Z_a(R')_b$Si—R", where Z=Cl, Br, I, $C_1$-$C_5$ alkoxy, dialkylamino, e.g., dimethylamino, or trifluoromethanesulfonate; a and b are each an integer from 0 to 3 provided that a+b=3; R' is a $C_1$-$C_6$ straight, cyclic or branched alkyl group, and R" is a functionalizing group. In certain instances, such materials have been surface modified by coating with a polymer.

R' includes, e.g., methyl, ethyl, propyl, isopropyl, butyl, t-butyl, sec-butyl, pentyl, isopentyl, hexyl or cyclohexyl; preferably, R' is methyl.

The functionalizing group R" may include alkyl, alkenyl, alkynyl, aryl, cyano, amino, diol, nitro, ester, cation or anion exchange groups, an alkyl or aryl group containing an embedded polar functionalities or chiral moieties. Examples of suitable R" functionalizing groups include chiral moieties, $C_1$-$C_{30}$ alkyl, including $C_1$-$C_{20}$, such as octyl ($C_8$), octadecyl ($C_{18}$) and triacontyl ($C_{30}$); alkaryl, e.g., $C_1$-$C_4$-phenyl; cyanoalkyl groups, e.g., cyanopropyl; diol groups, e.g., propyldiol; amino groups, e.g., aminopropyl; and alkyl or aryl groups with embedded polar functionalities, e.g., carbonate, amide, urea, ether, thioether, sulfinyl, sulfoxide, sulfonyl, thiourea, thiocarbonate, thiocarbamate, ethylene glycol, heterocyclic, and triazole functionalities or carbamate functionalities such as disclosed in U.S. Pat. No. 5,374,755, and chiral moieties. In certain embodiments, R" is selected from the group consisting of aromatic, phenylalkyl, fluoroaromatic, phenylhexyl, pentafluorophenylalkyl and chiral moieties. Such groups include those of the general formula

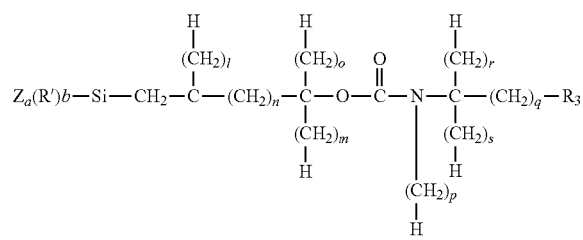

wherein l, m, o, r and s are 0 or 1, n is 0, 1, 2 or 3 p is 0, 1, 2, 3 or 4 and q is an integer from 0 to 19; $R_3$ is selected from the group consisting of hydrogen, alkyl, cyano and phenyl; and Z, R', a and b are defined as above. Preferably, the carbamate functionality has the general structure indicated below:

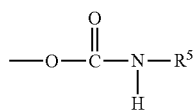

wherein $R^5$ may be, e.g., cyanoalkyl, t-butyl, butyl, octyl, dodecyl, tetradecyl, octadecyl, or benzyl. Advantageously, $R^5$ is octyl, dodecyl, or octadecyl.

In certain applications, such as chiral separations, the inclusion of a chiral moiety as a functionalizing group is particularly advantageous.

Polymer coatings are known in the literature and may be provided generally by polymerization or polycondensation of physisorbed monomers onto the surface without chemical bonding of the polymer layer to the support (type I), polymerization or polycondensation of physisorbed monomers onto the surface with chemical bonding of the polymer layer to the support (type II), immobilization of physisorbed prepolymers to the support (type III) and chemisorption of presynthesized polymers onto the surface of the support (type IV). see, e.g., Hanson, et al., *J. Chromat.* A656 (1993) 369-380, the text of which is incorporated herein by reference. As noted above, coating the hybrid material with a polymer may be used in conjunction with various surface modifications described in the invention.

Thus, in certain embodiments, the hydrophobic surface modifier is selected from the group consisting of phenyl-hexyltrichlorosilane, pentafluorophenylpropyltrichlorosilane, octyltrichlorosilane, octadecyltrichlorosilane, octyldimethylchlorosilane and octadecyldimethylchlorosilane. In a further embodiment, the surface modifier is selected from the group consisting of octyltrichlorosilane and octadecyltrichlorosilane.

In another embodiment, the high purity chromatographic materials have been surface modified by a combination of organic group and silanol group modification.

In other embodiments, the high purity chromatographic materials have been surface modified by a combination of organic group modification and coating with a polymer.

In other embodiments, the high purity chromatographic materials have been surface modified by a combination of silanol group modification and coating with a polymer.

In another embodiment, the high purity chromatographic materials have been surface modified via formation of an organic covalent bond between the hybrid cores' and/or surrounding material materials' organic group and the modifying reagent.

In certain embodiments, the high purity chromatographic materials have been surface modified by a combination of organic group modification, silanol group modification and coating with a polymer.

In one embodiment, the high purity chromatographic materials have been surface modified by silanol group modification.

In another embodiment, the invention provides a method wherein the high purity chromatographic materials are modified by further including a porogen. In a further embodiment, the porogen is selected from the group consisting of cyclohexanol, toluene, mesitylene, 2-ethylhexanoic acid, dibutylphthalate, 1-methyl-2-pyrrolidinone, 1-dodecanol and Triton X-45. In certain embodiments, the porogen is toluene or mesitylene.

In one embodiment, the invention provides a method wherein the high purity chromatographic materials are further modified by including a surfactant or stabilizer. In certain embodiments, the surfactant is Triton X-45, Triton X100, Triton X305, TLS, Pluronic F-87, Pluronic P-105, Pluronic P-123, sodium dodecylsulfate (SDS), ammonia docecylsulfate, TRIS docecylsulfate, or Triton X-165. In certain embodiments, the surfactant is sodium dodecylsulfate (SDS), ammonia docecylsulfate, or TRIS docecylsulfate.

Certain embodiments of the synthesis of the HPCMs of the invention including hybrids, silica, particles, monoliths and superficially porous materials, are described above are further illustrated in the Examples below.

EXAMPLES

The present invention may be further illustrated by the following non-limiting examples describing the surface modification of porous chromatographic materials.

Materials

All reagents were used as received unless otherwise noted. Those skilled in the art will recognize that equivalents of the following supplies and suppliers exist and, as such, the suppliers listed below are not to be construed as limiting.

Characterization

Those skilled in the art will recognize that equivalents of the following instruments and suppliers exist and, as such, the instruments listed below are not to be construed as limiting.

The % C, % H, % N values were measured by combustion analysis (CE-440 Elemental Analyzer; Exeter Analytical Inc., North Chelmsford, Mass.) or % C by Coulometric Carbon Analyzer (modules CM5300, CM5014, UIC Inc., Joliet, Ill.). The specific surface areas (SSA), specific pore volumes (SPV) and the average pore diameters (APD) of these materials were measured using the multi-point $N_2$ sorption method (Micromeritics ASAP 2400; Micromeritics Instruments Inc., Norcross, Ga.). The SSA was calculated using the BET method, the SPV was the single point value determined for $P/P_0 > 0.98$ and the APD was calculated from the desorption leg of the isotherm using the BJH method. Scanning electron microscopic (SEM) image analyses were performed (JEOL JSM-5600 instrument, Tokyo, Japan) at 7 kV. Particle sizes were measured using a Beckman Coulter Multisizer 3 analyzer (30 μm aperture, 70,000 counts; Miami, Fla.). The particle diameter (dp) was measured as the 50% cumulative diameter of the volume based particle size distribution. The width of the distribution was measured as the 90% cumulative volume diameter divided by the 10% cumulative volume diameter (denoted 90/10 ratio). Multi-nuclear ($^{13}C$, $^{29}Si$) CP-MAS NMR spectra were obtained using a Bruker Instruments Avance-300 spectrometer (7 mm double broadband probe). The spinning speed was typically 5.0-6.5 kHz, recycle delay was 5 sec. and the cross-polarization contact time was 6 msec. Reported $^{13}C$ and $^{29}Si$ CP-MAS NMR spectral shifts were recorded relative to tetramethylsilane using the external standards adamantane ($^{13}C$ CP-MAS NMR, δ 38.55) and hexamethylcyclotrisiloxane ($^{29}Si$ CP-MAS NMR, δ −9.62). Populations of different silicon environments were evaluated by spectral deconvolution using DMFit software. [Massiot, D.; Fayon, F.; Capron, M.; King, I.; Le Calvé, S.; Alonso, B.; Durand, J.-O.; Bujoli, B.; Gan, Z.; Hoatson, G. Magn. Reson. Chem. 2002, 40, 70-76] Titrations were performed using a Metrohm 716 DMS Titrino autotitrator with 6.0232.100 pH electrode (Metrohm, Hersau, Switzerland, or equivalent).

Example 1

BEH porous hybrid particles (15 g, Waters Corporation, Milford, Mass.; 6.5% C; SSA=186 m$^2$/g; SPV=0.79 cm$^3$/g; APD=151 Å) of the formula $(O_{1.5}SiCH_2CH_2SiO_{1.5})(SiO_2)_4$ (prepared following the method described in U.S. Pat. No. 6,686,035) were refluxed in toluene (100 mL, Fisher Scientific, Fairlawn, N.J.) using a Dean-Stark trap for 1 hour. Reaction 1a used 7.2 g BEH material. Upon cooling the Component A silane additive was added, which included aminopropyltriethoxysilane (APTES, Gelest Inc., Morrisville, Pa.), 2-(2-(trichlorosilyl)ethyl)pyridine (2PE, Gelest Inc., Morrisville, Pa.), 2-(4-pyridylethyl)triethoxysilane (4PE, Gelest Inc., Morrisville, Pa.), N-trimethoxysilylpropyl-N,N,N-trimethylammonium chloride (QPTMS, 50% solution in methanol, Gelest Inc., Morrisville, Pa.) or chloropropyltrimethoxysilane (CPTMS, Gelest Inc., Morrisville, Pa.). The reaction was heated to reflux for 1 hour. Upon cooling, imidazole (Aldrich, Milwaukee, Wis.) and octadecyldimethylchlorosilane (Component B, ODMCS, Aldrich or Gelest) were added. The reaction was then heated to reflux for 3 hours. For reactions 1j and 1k, 200 mL of toluene was used, and imidazole was added at the same time as the CPTMS. The reaction was then cooled and the product was filtered and washed successively with toluene, 1:1 v/v acetone/water and acetone (all solvents from Fisher Scientific). The product was then dried at 80° C. under reduced pressure for 16 hours. Reaction data is listed in Table 1. Product 1a was a control experiment that did not employ the use of a Component A silane additive. For products 1b-1l the Component A silane additive charges ranged between 0.03-10.6 μmol/m$^2$ and the charge molar ratio of Component B to A ranged from 0.19-66.6. Products 1k and 1l introduced a chloropropyl silane group to the particle which is known to react with imidazole to obtain an imidazole propyl group [A. M. Lazarin, Y. Gushikem and S. C. deCastro, J. Mater. Chem., 2000, 10, 2526; B. Gadenne, P. Hesemann, J. J. E. Moreau Chem. Commun., 2004, 1768]. The reaction between the chloropropyl groups with imidazole was confirmed using $^{13}C$ CP-MAS NMR spectroscopy.

The surface coverage of Component A silane additives was determined by the difference in particle % N after surface modification as measured by elemental analysis. As shown in Table 1, unbonded BEH particles as well as products 1a-1c did not have determinable nitrogen content by this measurement. ND stands for none determined. The surface coverage of $C_{18}$-groups was determined by the difference in particle % C before and after the surface modification as measured by elemental analysis. Surface coverage of $C_{18}$-groups could be corrected by factoring out carbon content due to Component A silane additive by assuming complete condensation of the silane additive (correction method I), or by using the value obtained from the Component A silane additive coverage calculation (correction method II). For products 1b-1j the correction in $C_{18}$ coverage may be overestimated, but is still quite small (less than 0.11 μmol/m$^2$).

TABLE 1

| Product | dp (μm) | Component A Silane Additive | Silane Additive Charge (μmol/m$^2$) | Silane Additive (g) | Component B ODMCS Silane (g) | Imidazole (g) | Charge Molar Ratio B/A | % C | % N | Silane Additive Coverage (μmol/m$^2$) (% N) | $C_{18}$ Coverage (μmol/m$^2$) (Δ % C) | Corrected $C_{18}$ Coverage (μmol/m$^2$) (□ % C) |
|---|---|---|---|---|---|---|---|---|---|---|---|---|
| 1a | 3.5 | — | — | — | 0.96 | 0.37 | — | 13.02 | ND | — | 1.71 | — |
| 1b | 3.4 | APTES | 0.03 | 0.019 | 1.99 | 0.78 | 66.6 | 13.34 | ND | ND | 1.80 | 1.80 (I) |
| 1c | 3.4 | APTES | 0.06 | 0.036 | 1.92 | 0.75 | 33.3 | 13.54 | ND | ND | 1.93 | 1.92 (I) |
| 1d | 3.4 | APTES | 0.30 | 0.190 | 1.99 | 0.78 | 6.66 | 13.27 | 0.15 | 0.20 | 1.78 | 1.75 (I) |
| 1e | 3.4 | APTES | 0.60 | 0.380 | 1.99 | 0.78 | 3.33 | 11.83 | 0.20 | 0.27 | 1.37 | 1.30 (I) |
| 1f | 3.4 | 2PE | 0.30 | 0.199 | 1.92 | 0.75 | 6.66 | 13.87 | 0.13 | 0.26 | 2.03 | 1.93 (I) |
| 1g | 4.8 | 4PE | 0.06 | 0.046 | 1.89 | 0.78 | 33.3 | 13.38 | 0.09 | 0.17 | 1.68 | 1.66 (I) |
| 1h | 3.4 | 4PE | 0.30 | 0.223 | 1.92 | 0.75 | 6.66 | 13.48 | 0.14 | 0.28 | 1.91 | 1.81 (I) |
| 1i | 4.8 | QPTMS | 0.06 | 0.089 | 1.89 | 0.78 | 33.3 | 12.97 | 0.10 | 0.23 | 1.56 | 1.54 (I) |
| 1j | 3.4 | QPTMS | 0.30 | 0.427 | 1.92 | 0.75 | 6.66 | 13.17 | 0.13 | 0.31 | 1.81 | 1.74 (I) |
| 1k | 3.4 | CPTMS | 1.20 | 0.658 | 1.92 | 3.76 | 1.66 | 12.66 | 0.58 | 0.74 | 1.66 | 1.49 (II) |
| 1l | 3.4 | CPTMS | 10.6 | 5.840 | 1.92 | 3.76 | 0.19 | 10.15 | 1.45 | 1.99 | 0.95 | 0.45 (II) |

Example 2

Materials from Example 1 were modified with trimethylchlorosilane (TMCS, Gelest Inc., Morrisville, Pa.) using imidazole (Aldrich, Milwaukee, Wis.) in refluxing toluene (100 mL) for 4 hours. The reaction was then cooled and the product was filtered and washed successively with water, toluene, 1:1 v/v acetone/water and acetone (all solvents from J. T. Baker) and then dried at 80° C. under reduced pressure for 16 hours. Reaction data are listed in Table 2.

TABLE 2

| Product | Precursor | Particles (g) | TMCS (g) | Imidazole (g) | % C |
|---|---|---|---|---|---|
| 2a | 1a | 7.2 | 1.49 | 1.12 | 13.96 |
| 2b | 1b | 15.9 | 3.27 | 2.48 | 14.22 |
| 2c | 1c | 15.0 | 3.00 | 2.25 | 14.33 |
| 2d | 1d | 15.0 | 3.11 | 2.34 | 13.97 |
| 2e | 1e | 15.6 | 3.30 | 2.44 | 12.93 |
| 2f | 1f | 15.0 | 3.00 | 2.25 | 14.57 |
| 2g | 1g | 15.0 | 3.11 | 2.34 | 14.19 |
| 2h | 1h | 15.0 | 3.00 | 2.25 | 14.19 |
| 2i | 1i | 15.0 | 3.11 | 2.34 | 13.80 |
| 2j | 1j | 15.0 | 3.00 | 2.25 | 13.83 |
| 2k | 1k | 15.0 | 2.99 | 2.25 | 13.12 |
| 2l | 1l | 15.0 | 2.99 | 2.25 | 11.00 |

Example 3

BEH porous hybrid particles (Waters Corporation, Milford, Mass.; 6.5% C; SSA=182-185 $m^2$/g; SPV=0.72-0.76 $cm^3$/g; APD=142-151 Å) of the formula $(O_{1.5}SiCH_2CH_2SiO_{1.5})(SiO_2)_4$ (prepared following the method described in U.S. Pat. No. 6,686,035) were refluxed in toluene (5 mL/g, Fisher Scientific, Fairlawn, N.J.) using a Dean-Stark trap for 1 hour. Upon cooling the Component A silane additive was added, which included aminopropyltriethoxysilane (APTES, Gelest Inc., Morrisville, Pa.) 2-(4-pyridylethyl) triethoxysilane (4PE, Gelest Inc., Morrisville, Pa.), or diethylphosphatoethyltriethoxysilane (DEPS, Gelest Inc. Morrisville, Pa.) or 2-(4-chlorosulfonylphenyl)ethyltrichlorosilane (SPETCS, 50% in toluene, Gelest Inc., Morrisville Pa.). The reaction was heated to reflux for 1 hour. Upon cooling, imidazole (Aldrich, Milwaukee, Wis.) and octadecyltrichlorosilane (Component B, ODTCS, Aldrich, Milwaukee, Wis.) were added. The reaction was then heated to reflux for 16 hours. Product 3c was reacted for 3 hours. Products 3af-3aj did not add a component B.

The reaction was then cooled and the product was filtered and was washed successively with toluene, 1:1 v/v acetone/water, and acetone (all solvents from J. T. Baker). The material was then refluxed in a acetone/aqueous 0.12 M ammonium acetate solution (Sigma Chemical Co., St. Louis, Mo.) for 2 hours (hydrolysis-type A), acetone/aqueous 0.1 M ammonium bicarbonate (pH 8) solution for 20 hours at 50° C. (hydrolysis-type B), or acetone/aqueous 0.1 M ammonium bicarbonate (pH 10) solution for 20 hours at 50° C. (hydrolysis-type C). The reaction was then cooled and the product was filtered and washed successively with toluene, 1:1 v/v acetone/water, and acetone (all solvents from J. T. Baker). The product was then dried at 80° C. under reduced pressure for 16 hours. Reaction data is listed in Table 3. The silane additive (Component A) charges ranged from 0.03-3.70 µmol/$m^2$ and the molar ratio of charge molar ratio of Component B to A ranged from 4.3-133.4.

The surface coverage of $C_{18}$-groups was determined by the difference in particle % C before and after the surface modification as measured by elemental analysis. Correction for coverage of $C_{18}$-groups, obtained by factoring out carbon content due to silane additive by assuming complete condensation of the silane additive, were small for this dataset (less than 0.15 µmol/$m^2$) and were not included in Table 3. Product 3aj had an ion-exchange capacity of 0.22 mequiv/g by titration.

TABLE 3

| | | | Component A | | Component B | | | Charge | | | |
|---|---|---|---|---|---|---|---|---|---|---|---|
| | | | Silane | | | | | | | | |
| Product | dp (µm) | Particles (g) | Silane Additive | Additive Charge (µmol/$m^2$) | Silane Additive (g) | ODTCS Charge (µmol/$m^2$) | ODTCS Silane (g) | Imidazole (g) | Molar Ratio B/A | Hydrolysis Type | % C | $C_{18}$ Coverage (µmol/$m^2$) |
| 3a | 2.9 | 15 | APTES | 0.03 | 0.018 | 3.99 | 4.30 | 1.51 | 133.4 | A | 16.53 | 3.19 |
| 3b | 2.9 | 15 | APTES | 0.06 | 0.037 | 2.00 | 2.15 | 0.76 | 33.2 | A | 12.80 | 1.84 |
| 3c | 2.9 | 50 | APTES | 0.06 | 0.124 | 4.00 | 14.43 | 5.06 | 66.7 | A | 16.33 | 3.13 |
| 3d | 1.8 | 20 | APTES | 0.06 | 0.050 | 4.06 | 5.74 | 2.02 | 65.3 | A | 16.24 | 3.26 |
| 3e | 2.9 | 30 | APTES | 0.12 | 0.147 | 4.00 | 8.61 | 3.03 | 33.3 | A | 15.92 | 2.96 |
| 3f | 2.9 | 30 | APTES | 0.20 | 0.246 | 4.00 | 8.61 | 3.03 | 20.0 | A | 16.10 | 3.03 |
| 3g | 2.9 | 15 | 4PE | 0.06 | 0.045 | 1.99 | 2.14 | 0.76 | 33.0 | A | 13.13 | 2.05 |
| 3h | 2.9 | 15 | 4PE | 0.06 | 0.045 | 3.99 | 4.30 | 1.51 | 66.4 | A | 16.70 | 3.36 |
| 3i | 2.9 | 15 | 4PE | 0.30 | 0.224 | 1.99 | 2.14 | 0.76 | 6.6 | A | 13.33 | 2.12 |
| 3j | 3.9 | 20 | 4PE | 0.30 | 0.294 | 2.00 | 2.82 | 0.99 | 6.7 | A | 13.22 | 2.05 |
| 3k | 2.9 | 15 | 4PE | 0.30 | 0.224 | 3.99 | 4.30 | 1.51 | 13.3 | A | 16.64 | 3.33 |
| 3l | 3.9 | 15 | 4PE | 0.31 | 0.230 | 2.00 | 2.12 | 0.74 | 6.4 | A | 13.44 | 2.13 |
| 3m | 3.9 | 15 | 4PE | 0.31 | 0.230 | 2.00 | 2.12 | 0.74 | 6.4 | B | 13.12 | 2.02 |
| 3n | 3.9 | 20 | 4PE | 0.20 | 0.196 | 1.72 | 2.43 | 0.85 | 8.6 | B | 12.06 | 1.65 |
| 3o | 3.9 | 20 | 4PE | 0.40 | 0.392 | 2.28 | 3.22 | 1.13 | 5.7 | B | 13.84 | 2.27 |
| 3p | 3.9 | 20 | 4PE | 0.40 | 0.392 | 1.72 | 2.43 | 0.85 | 4.3 | C | 12.40 | 1.77 |
| 3q | 3.9 | 20 | 4PE | 0.20 | 0.196 | 2.28 | 3.22 | 1.13 | 11.4 | C | 13.68 | 2.21 |
| 3r | 3.5 | 20 | 4PE | 0.40 | 0.394 | 2.30 | 3.27 | 1.15 | 5.8 | B | 14.04 | 2.4 |
| 3s | 3.5 | 20 | 4PE | 0.40 | 0.394 | 2.30 | 3.27 | 1.15 | 5.8 | C | 14.16 | 2.44 |
| 3t | 1.8 | 20 | 4PE | 0.30 | 0.297 | 2.00 | 2.86 | 1.00 | 5.0 | B | 13.28 | 2.01 |
| 3u | 3.5 | 20 | 4PE | 0.35 | 0.346 | 2.53 | 3.59 | 1.26 | 7.2 | C | 14.41 | 2.46 |
| 3v | 3.5 | 20 | 4PE | 0.35 | 0.346 | 2.07 | 2.94 | 1.03 | 5.9 | C | 13.40 | 2.10 |
| 3w | 3.5 | 20 | 4PE | 0.25 | 0.246 | 2.53 | 3.59 | 1.26 | 10.1 | C | 14.59 | 2.52 |
| 3x | 3.5 | 20 | 4PE | 0.25 | 0.246 | 2.07 | 2.94 | 1.03 | 8.3 | C | 13.28 | 2.06 |
| 3y | 3.5 | 20 | 4PE | 0.20 | 0.197 | 2.70 | 3.83 | 1.35 | 13.5 | B | 14.88 | 2.71 |
| 3z | 3.5 | 20 | 4PE | 0.40 | 0.394 | 2.70 | 3.83 | 1.35 | 6.8 | B | 14.81 | 2.68 |

TABLE 3-continued

| | | | Component A | | Component B | | | Charge | | | |
| | | | Silane | | | | | | | | |
| Product | dp (μm) | Particles (g) | Silane Additive | Additive Charge (μmol/m²) | Silane Additive (g) | ODTCS Charge (μmol/m²) | ODTCS Silane (g) | Imidazole (g) | Molar Ratio B/A | Hydrolysis Type | % C | $C_{18}$ Coverage (μmol/m²) |
|---|---|---|---|---|---|---|---|---|---|---|---|---|
| 3aa | 3.5 | 20 | 4PE | 0.20 | 0.197 | 2.70 | 3.83 | 1.35 | 13.5 | C | 14.71 | 2.65 |
| 3ab | 3.5 | 20 | 4PE | 0.40 | 0.394 | 2.70 | 3.83 | 1.35 | 6.8 | C | 14.90 | 2.71 |
| 3ac | 1.8 | 40 | 4PE | 0.30 | 0.595 | 2.30 | 6.57 | 2.30 | 7.7 | C | 14.01 | 2.27 |
| 3ad | 3.5 | 40 | 4PE | 0.30 | 0.592 | 2.30 | 6.53 | 2.29 | 7.7 | C | 13.97 | 2.38 |
| 3ae | 4.9 | 22 | 4PE | 0.30 | 0.316 | 2.30 | 3.49 | 1.23 | 7.7 | C | 13.90 | 2.28 |
| 3af | 3.9 | 15 | 4PE | 0.03 | 0.022 | — | — | — | — | C | 6.46 | — |
| 3ag | 3.9 | 15 | 4PE | 0.06 | 0.044 | — | — | — | — | C | 6.38 | — |
| 3ah | 3.9 | 15 | 4PE | 3.70 | 2.700 | — | — | — | — | C | 7.80 | — |
| 3ai | 4.0 | 30 | DEPS | 3.00 | 5.400 | — | — | — | — | C | 7.62 | — |
| 3aj | 4.0 | 40 | SPETCS | 1.00 | 4.90 | — | — | 5.00 | — | C | 7.94 | — |

Example 4

Materials from Example 3 were modified with triethylchlorosilane (TECS, Gelest Inc., Morrisville, Pa.) or tert-butyldimethylchlorosilane (TBDMCS, Gelest Inc., Morrisville, Pa.) using imidazole (Aldrich, Milwaukee, Wis.) in refluxing toluene (5 mL/g) for 4-20 hours. The reaction was cooled and the product was filtered and washed successively with water, toluene, 1:1 v/v acetone/water and acetone (all solvents from J. T. Baker) and then dried at 80° C. under reduced pressure for 16 hours. Reactions 4a-4-g and 4m-4ab were reacted for 4 hours, reactions 4h-4l were reacted for 20 hours. Additional trimethylchlorosilane (TMCS, Gelest Inc., Morrisville, Pa.) and imidazole was added to reactions 4m-4ab and the reaction was heated for an additional 16 hours. Selected products were further reacted with TMCS (reaction 4k) or hexamethyldisilazane (reaction 4c, Gelest Inc., Morrisville, Pa.) in a similar process. Reaction data are listed in Table 4.

TABLE 4

| Product | Precursor | Particles (g) | Silane | Silane (g) | Imidazole (g) | % C |
|---|---|---|---|---|---|---|
| 4a | 3a | 15 | TECS | 4.18 | 2.27 | 17.32 |
| 4b | 3b | 15 | TECS | 4.18 | 2.27 | 14.53 |
| 4c | 3c | 50 | TECS | 13.95 | 7.75 | 17.58 |
| 4d | 3d | 10 | TECS | 2.79 | 1.51 | 17.27 |
| 4e | 3d | 10 | TBDMCS | 2.79 | 1.51 | 16.99 |
| 4f | 3e | 32 | TECS | 9.00 | 4.85 | 16.96 |
| 4g | 3f | 32 | TECS | 8.4.0 | 4.55 | 17.10 |
| 4h | 3g | 15 | TBDMCS | 4.18 | 2.27 | 14.54 |
| 4i | 3h | 15 | TBDMCS | 4.18 | 2.27 | 17.44 |
| 4j | 3i | 15 | TBDMCS | 4.18 | 2.27 | 14.62 |
| 4k | 3j | 20 | TBDMCS | 5.48 | 2.97 | 14.61 |
| 4l | 3k | 15 | TBDMCS | 4.18 | 2.27 | 17.30 |
| 4m | 3l | 15 | TECS | 2.06 | 1.12 | 15.14 |
| 4n | 3m | 15 | TECS | 2.06 | 1.12 | 14.82 |
| 4o | 3n | 20 | TECS | 2.74 | 1.49 | 14.28 |
| 4p | 3o | 20 | TECS | 2.74 | 1.49 | 15.43 |
| 4q | 3p | 20 | TECS | 2.74 | 1.49 | 15.26 |
| 4r | 3q | 20 | TECS | 2.74 | 1.49 | 15.36 |
| 4s | 3r | 20 | TECS | 2.74 | 1.49 | 15.61 |
| 4t | 3s | 20 | TECS | 2.74 | 1.49 | 15.67 |
| 4u | 3t | 20 | TECS | 2.74 | 1.49 | 14.96 |
| 4v | 3u | 20 | TECS | 2.38 | 1.29 | 15.92 |
| 4w | 3v | 20 | TECS | 2.24 | 1.22 | 14.99 |
| 4x | 3w | 20 | TECS | 2.21 | 1.20 | 15.97 |
| 4y | 3x | 20 | TECS | 2.25 | 1.22 | 14.97 |
| 4z | 3ac | 20 | TECS | 2.78 | 1.50 | 15.71 |
| 4aa | 3ad | 10 | TECS | 2.76 | 1.50 | 15.52 |
| 4ab | 3ae | 22 | TECS | 2.70 | 1.47 | 15.51 |
| 4ac | 3ad | 10 | TBDMCS | 3.40 | 3.00 | 15.36 |

Example 5

BEH porous hybrid particles (Waters Corporation, Milford, Mass.; 3.9 μm, 6.68% C; SSA=182 m²/g; SPV=0.75 cm³/g; APD=148 Å) of the formula $(O_{1.5}SiCH_2CH_2SiO_{1.5})(SiO_2)_4$ (prepared following the method described in U.S. Pat. No. 6,686,035) were refluxed in toluene (5 mL/g, Fisher Scientific, Fairlawn, N.J.) using a Dean-Stark trap for 1 hour. Upon cooling the Component A silane additive was added, which included aminopropyltriethoxysilane (APTES, Gelest Inc., Morrisville, Pa.), 2-(4-pyridylethyl)triethoxysilane (4PE, Gelest Inc., Morrisville, Pa.), or 2-(carbomethoxy) ethyltrichlorosilane (CMETCS, Gelest Inc., Morrisville, Pa.). The reaction was heated to reflux for 1 hour. For reactions 5f and 5g a mixture of APTES and CMETCS were used. Upon cooling, imidazole (Aldrich, Milwaukee, Wis.) or diisopropyl ethylamine (DIPEA, Aldrich, Milwaukee, Wis.) and the Component B silane was added, which included phenylhexyltrichlorosilane (PTCS), octyltrichlorosilane (OTCS, Aldrich, Milwaukee, Wis.), pentafluorophenylpropyltrichlorosilane (PFPPTCS), or octadecyldimethylchlorosilane (ODMCS, Aldrich, Milwaukee, Wis.). Products 5a-5h used imidazole. Products 5i-5t used DIPEA. The reaction was then heated to reflux for 16 hours.

The reaction was cooled and the product was filtered and was washed successively with toluene, 1:1 v/v acetone/water, and acetone (all solvents from J. T. Baker). The material was then hydrolyzed as detailed in Example 3. Products 5a-5h used hydrolysis type A. Products 5i-5u used hydrolysis type C. The reaction was then cooled and the product was filtered and washed successively with toluene, 1:1 v/v acetone/water, and acetone (all solvents from J. T. Baker). The product was then dried at 70° C. under reduced pressure for 16 hours. Reaction data is listed in Table 5. The Component A silane additive charges ranged from 0.03-0.35 μmol/m² and the charge molar ratio of Component B to A ranged from 6.5-133.3. The surface coverage was determined by the difference in particle % C before and after the surface modification as measured by elemental analysis.

TABLE 5

| Product | dp (μm) | Particles (g) | Component A Silane Additive | Component A Silane Additive Charge (μmol/m²) | Component A Silane Additive (g) | Component B Primary Silane | Component B Primary Silane Charge (μmol/m²) | Component B Primary Silane (g) | Base (g) | Charge Molar Ratio B/A | % C | Surface Coverage (μmol/m²) |
|---|---|---|---|---|---|---|---|---|---|---|---|---|
| 5a | 3.9 | 15 | APTES | 0.03 | 0.018 | PTCS | 2 | 1.16 | 0.74 | 66.7 | 9.75 | 1.22 |
| 5b | 3.9 | 15 | APTES | 0.03 | 0.018 | PTCS | 4 | 2.33 | 1.49 | 133.3 | 12.27 | 2.32 |
| 5c | 3.9 | 15 | APTES | 0.06 | 0.036 | PTCS | 2 | 1.16 | 0.74 | 33.3 | 10.09 | 1.37 |
| 5d | 3.9 | 15 | APTES | 0.06 | 0.036 | PTCS | 4 | 2.33 | 1.49 | 66.7 | 12.19 | 2.28 |
| 5e | 3.9 | 15 | 4PE | 0.31 | 0.22 | OTCS | 2 | 1.35 | 0.74 | 6.5 | 9.435 | 1.88 |
| 5f | 3.9 | 15 | APTES; CMETCS | 0.06, 0.06 | 0.036, 0.036 | ODTCS | 4 | 4.24 | 1.49 | 66.7 | 15.94 | 2.72 |
| 5g | 3.9 | 15 | APTES; CMETCS | 0.03, 0.03 | 0.018, 0.018 | ODTCS | 4 | 4.24 | 1.49 | 133.3 | 16.02 | 2.74 |
| 5h | 3.9 | 15 | CMETCS | 0.06 | 0.036 | ODTCS | 4 | 4.24 | 1.49 | 66.7 | 15.86 | 2.69 |
| 5i | 1.8 | 41 | 4PE | 0.30 | 0.60 | PFPPTCS | 2.30 | 5.90 | 4.40 | 7.7 | 10.30 | 2.34 |
| 5j | 1.8 | 40 | 4PE | 0.35 | 0.68 | PFPPTCS | 2.29 | 5.60 | 4.20 | 6.5 | 9.93 | 2.39 |
| 5k | 3.5 | 40 | 4PE | 0.30 | 0.59 | PFPPTCS | 3.00 | 7.55 | 5.68 | 10.0 | 10.61 | 2.65 |
| 5l | 3.5 | 40 | 4PE | 0.30 | 0.59 | PFPPTCS | 2.30 | 5.78 | 4.35 | 7.7 | 10.06 | 2.24 |
| 5m | 4.9 | 70 | 4PE | 0.30 | 1.04 | PFPPTCS | 2.29 | 10.10 | 7.60 | 7.7 | 10.46 | 2.61 |
| 5n | 3.5 | 40 | 4PE | 0.30 | 0.59 | PTCS | 2.30 | 4.98 | 4.35 | 7.7 | 11.43 | 2.15 |
| 5o | 1.8 | 40 | 4PE | 0.30 | 0.57 | PTCS | 2.31 | 4.80 | 4.20 | 7.7 | 11.18 | 2.16 |
| 5p | 3.0 | 16 | 4PE | 0.30 | 0.24 | PTCS | 2.01 | 1.79 | 1.79 | 6.7 | 12.26 | 2.66 |
| 5q | 4.5 | 70 | 4PE | 0.30 | 1.04 | PTCS | 2.30 | 8.70 | 7.60 | 7.7 | 11.11 | 2.05 |
| 5r | 4.5 | 70 | 4PE | 0.30 | 1.04 | PTCS | 2.30 | 8.70 | 7.60 | 7.7 | 11.41 | 2.19 |
| 5s | 3.5 | 350 | 4PE | 0.30 | 5.40 | PTCS | 2.30 | 45.50 | 39.70 | 7.7 | 12.16 | 2.43 |
| 5t | 3.5 | 80 | 4PE | 0.30 | 1.25 | PTCS | 2.31 | 10.60 | 9.20 | 7.7 | 11.81 | 2.30 |
| 5u | 3.5 | 40 | 4PE | 0.30 | 0.592 | PTCS | 2.31 | 5.00 | 2.3 | 7.7 | 11.89 | 2.39 |

Example 6

Material from Example 5 was modified with triethylchlorosilane (TECS, Gelest Inc., Morrisville, Pa.) or tert-butyldimethylchlorosilane (TBDMCS, Gelest Inc., Morrisville, Pa.) using imidazole (Aldrich, Milwaukee, Wis.) in refluxing toluene (5 mL/g) for 17-20 hours. Additional TMCS and imidazole was added to reactions 6e, 6i-6o, and 6q after 4 hours and the reaction was heated for an additional 16 hours. For reactions 6i and 6j diisopropyl ethylamine (DIPEA, Aldrich, Milwaukee, Wis.) was used in place of imidazole. The reaction was then cooled and the product was filtered and washed successively with water, toluene, 1:1 v/v acetone/water and acetone (all solvents from J. T. Baker) and then dried at 70° C. under reduced pressure for 16 hours. Samples of product 6p were further hydrolyzed in an aqueous acetonitrile solution or hydrolysis C in Example 3. No noticeable change in carbon content was observed. Reaction data are listed in Table 6.

TABLE 6

| Product | Precursor | Particles (g) | Silane | Silane (g) | Base (g) | % C |
|---|---|---|---|---|---|---|
| 6a | 5a | 15 | TBDMCS | 4.11 | 2.23 | 11.36 |
| 6b | 5b | 15 | TBDMCS | 4.11 | 2.23 | 13.44 |
| 6c | 5c | 15 | TBDMCS | 4.11 | 2.23 | 11.71 |
| 6d | 5d | 15 | TBDMCS | 4.11 | 2.23 | 13.33 |
| 6e | 5e | 15 | TECS | 2.06 | 1.12 | 11.56 |
| 6f | 5f | 15 | TBDMCS | 4.11 | 2.23 | 16.66 |
| 6g | 5g | 15 | TBDMCS | 4.11 | 2.23 | 16.76 |
| 6h | 5h | 15 | TBDMCS | 4.11 | 2.23 | 16.89 |
| 6i | 5l | 20 | TECS | 2.57 | 2.64 | 11.55 |
| 6j | 5n | 19 | TECS | 2.59 | 2.66 | 12.90 |
| 6k | 5o | 40 | TECS | 5.31 | 2.88 | 13.60 |
| 6l | 5p | 10 | TECS | 1.45 | 0.79 | 13.91 |
| 6m | 5q | 67 | TECS | 9.20 | 5.00 | 13.75 |
| 6n | 5r | 70 | TECS | 9.20 | 5.00 | 13.06 |
| 6o | 5s | 20 | TECS | 2.92 | 1.58 | 13.80 |
| 6p | 5s | 40 | TBDMCS | 9.21 | 4.99 | 13.32 |
| 6q | 5u | 36 | TECS | 5.00 | 2.70 | 13.43 |

Example 7

BEH porous hybrid particles (15 g, 1.7 μm, Waters Corporation, Milford, Mass.; 6.5% C; SSA=92 m²/g; SPV=0.73 cm³/g; APD=311 Å) of the formula $(O_{1.5}SiCH_2CH_2SiO_{1.5})(SiO_2)_4$ (prepared following the method described in U.S. Pat. No. 6,686,035) were refluxed in toluene (100 mL, Fisher Scientific, Fairlawn, N.J.) using a Dean-Stark trap for 2 hours. Upon cooling the Component A silane additive aminopropyltriethoxysilane (0.018 g, 0.06 μmol/m² charge, Gelest Inc., Morrisville, Pa.) was added and the reaction was heated to reflux for 1 hour. Upon cooling, imidazole (5.06 g, Aldrich, Milwaukee, Wis.) and the Component B silane tert-butyldimethylchlorosilane (2.08 g, Gelest Inc., Morrisville, Pa.) were added. The reaction was then heated to reflux for 20 hours. The reaction was then cooled and the product was filtered and washed successively with water, toluene, 1:1 v/v acetone/water and acetone (all solvents from J. T. Baker) and then dried at 80° C. under reduced pressure for 16 hours. The surface coverage of product 7a, determined by the difference in particle % C before and after the surface modification (7.88% C) as measured by elemental analysis, was determined to be 2.50 μmol/m².

Example 8

Porous silica particles (Waters Corporation, Milford, Mass.; 3.5 μm; SSA=251 m²/g; SPV=0.80 cm³/g; APD=119

Å) were refluxed in toluene (5 mL per gram of silica, Fisher Scientific, Fairlawn, N.J.) using a Dean-Stark trap for 1 hour. Upon cooling the Component A silane additive was added, which included aminopropyltriethoxysilane (APTES, Gelest Inc., Morrisville, Pa.) or 2-(4-pyridylethyl)triethoxysilane (4PE, Gelest Inc., Morrisville, Pa.). Product 8a used APTES. Products 8b-d used 4PE. The reaction was heated to reflux for 1 hour. Upon cooling, imidazole (Aldrich, Milwaukee, Wis.) or diisopropyl ethylamine (DIPEA, Aldrich, Milwaukee, Wis.) and the Component B silane was added, which included phenylhexyltrichlorosilane (PTCS), pentafluorophenylpropyltrichlorosilane (PFPPTCS), or octadecyldimethylchlorosilane (ODMCS, Aldrich, Milwaukee, Wis.). Products 8a and 8b used Imidazole. Products 8c and 8d used DIPEA. The reaction was then heated to reflux for 20 hours. The reaction was then cooled and the product was filtered and was washed successively with toluene, 1:1 v/v acetone/water, and acetone (all solvents from J. T. Baker). The material was then refluxed in an acetone/aqueous 0.1M ammonium acetate solution (Sigma Chemical Co., St. Louis, Mo.) for 3.5 hours. Products 8b, 8c and 8d were heated at 50° C. for 20 hours. The reaction was then cooled and the product was filtered and washed successively with toluene, 1:1 v/v acetone/water, and acetone (all solvents from J. T. Baker). The product was then dried at 80° C. under reduced pressure for 16 hours. The surface coverage of the product, determined by the difference in particle % C before and after the surface modification as measured by elemental analysis. Products 8a, was further reacted in a similar manner as described for product 4c, to yield products 8e. Products 8b and 8d were further reacted in a similar manner as described for product 4m, to yield products 8f and 8g. Reaction data are listed in Table 7.

Example 9

Samples of porous particles from Example 2, 4, 6, and 8 were used for the separation of a mixture of neutral, polar and basic compounds listed in Table 8. The 2.1×100 mm chromatographic columns were packed using a slurry packing technique. The chromatographic system consisted of an ACQUITY UPLC® System and an ACQUITY UPLC® Tunable UV detector. Empower 2 Chromatography Data Software (Build 2154) was used for data collection and analysis. Mobile phase conditions were: 20 mM $K_2HPO_4$/$KH_2PO_4$, pH 7.00±0.02/methanol (40/60 v/v); flow rate: 0.25 mL/min; temperature: 30° C.; detection: 254 nm; analytes: uracil, propranolol, butylparaben, naphthalene, dipropylphthalate, acenaphthene, and amitriptyline. Columns 4g and 8a were tested at 23° C.

It can be seen that columns packed with particles from Examples 2, 4, 6, 7 and 8 provide sufficient retention and resolution in the separation of neutral, polar, and basic compounds under these conditions. Relative retention is the retention time of the analyte divided by the retention time of acenaphthene. Therefore values less than one, indicate less retention than acenaphthene, and values greater than one, indicate more retention than acenaphthene. (Relative retention is a well known parameter in the field of HPLC.)

TABLE 7

| Product | Particles (g) | Component A | | Component B | | | | | Surface Coverage ($\mu mol/m^2$) | Endcap | |
| | | Silane Additive Charge ($\mu mol/m^2$) | Silane Additive (g) | Primary Silane | Primary Silane Charge ($\mu mol/m^2$) | Primary Silane (g) | Base (g) | Charge Molar Ratio B/A | % C | | Endcap Product | Final % C |
| --- | --- | --- | --- | --- | --- | --- | --- | --- | --- | --- | --- | --- |
| 8a | 40 | 0.060 | 0.13 | ODTCS | 4.0 | 15.58 | 5.47 | 66.7 | 14.77 | 3.45 | 8e | 16.00 |
| 8b | 25 | 0.30 | 0.507 | ODTCS | 2.3 | 5.60 | 2.00 | 7.6 | 11.48 | 2.53 | 8f | 13.39 |
| 8c | 25 | 0.30 | 0.507 | PFPPTCS | 2.3 | 5.00 | 3.7 | 7.6 | 6.25 | 2.71 | — | — |
| 8d | 25 | 0.30 | 0.507 | PTCS | 2.3 | 4.30 | 3.7 | 7.6 | 7.94 | 2.49 | 8g | 10.31 |

TABLE 8

| Product | Retention Factor: Acenaphthene | Relative Retention: | | | | |
| | | Propranolol/Acenaphthene | Butylparaben/Acenaphthene | Naphthalene/Acenaphthene | Dipropyl phthalate/Acenaphthene | Amitriptyline/Acenaphthene |
| --- | --- | --- | --- | --- | --- | --- |
| 2a | 8.45 | 0.218 | 0.300 | 0.458 | 0.540 | 1.768 |
| 2b | 8.79 | 0.218 | 0.291 | 0.455 | 0.520 | 1.860 |
| 4f | 13.49 | 0.145 | 0.210 | 0.422 | 0.382 | 1.578 |
| 4g | 13.80 | 0.140 | 0.219 | 0.431 | 0.382 | 1.508 |
| 4j | 8.87 | 0.232 | 0.287 | 0.458 | 0.505 | 2.254 |
| 4k | 8.14 | 0.215 | 0.292 | 0.459 | 0.482 | 1.624 |
| 4m | 8.09 | 0.210 | 0.285 | 0.452 | 0.457 | 1.574 |
| 4n | 8.24 | 0.215 | 0.284 | 0.450 | 0.458 | 1.557 |
| 4o | 7.58 | 0.232 | 0.296 | 0.456 | 0.502 | 1.690 |
| 4p | 8.86 | 0.204 | 0.265 | 0.444 | 0.440 | 1.554 |
| 4q | 7.28 | 0.229 | 0.300 | 0.459 | 0.460 | 1.537 |
| 4r | 9.39 | 0.192 | 0.248 | 0.439 | 0.435 | 1.564 |
| 4s | 9.38 | 0.189 | 0.270 | 0.270 | 0.441 | 1.478 |
| 4t | 9.59 | 0.183 | 0.264 | 0.321 | 0.426 | 1.432 |
| 4u | 8.91 | 0.208 | 0.275 | 0.444 | 0.455 | 1.557 |
| 4z | 10.52 | 0.169 | 0.247 | 0.432 | 0.421 | 1.425 |
| 4aa | 9.92 | 0.183 | 0.255 | 0.439 | 0.429 | 1.488 |
| 4ac | 9.56 | 0.182 | 0.248 | 0.444 | 0.432 | 1.651 |
| 6e | 3.23 | 0.298 | 0.412 | 0.543 | 0.650 | 1.648 |
| 6f | 10.51 | 0.195 | 0.214 | 0.443 | 0.418 | 2.199 |

TABLE 8-continued

| Product | Retention Factor: Acenaphthene | Relative Retention: Propranolol/ Acenaphthene | Butylparaben/ Acenaphthene | Naphthalene/ Acenaphthene | Dipropyl phthalate/ Acenaphthene | Amitriptyline/ Acenaphthene |
|---|---|---|---|---|---|---|
| 6g | 10.61 | 0.191 | 0.212 | 0.443 | 0.418 | 2.182 |
| 6h | 10.52 | 0.193 | 0.213 | 0.443 | 0.421 | 2.229 |
| 8a | 18.32 | 0.130 | 0.196 | 0.419 | 0.364 | 1.302 |
| Commercial <2 μm Hybrid $C_{18}$ Column | 10.49 | 0.168 | 0.228 | 0.436 | 0.425 | 1.438 |
| Commercial <2 μm Silica $C_{18}$ Column | 13.39 | 0.213 | 0.252 | 0.426 | 0.530 | 2.078 |
| Commercial <2 μm Silica $C_{18}$ Column | 17.85 | 0.153 | 0.194 | 0.417 | 0.378 | 1.404 |
| Commercial <2 μm Silica $C_{18}$ Column | 6.70 | 2.663 | 0.284 | 0.480 | 0.495 | 17.912 |

Example 10

Samples of porous particles from Example 2, 4, 6, and 8 were evaluated for USP peak tailing factors using the mobile phase and test conditions of Example 9. The results are shown in Table 9. Peak tailing factors is a well known parameter in the field of HPLC (a lower value corresponds to reduced tailing). It is evident that columns packed with particles from Examples 2, 4, 6, 7 and 8 have comparable tailing factors to commercially available $C_{18}$-columns.

Example 11

Samples of porous particles from Example 2-8 were used for the separation of a mixture of neutral, polar and basic compounds listed in Table 10. The 2.1×100 mm chromatographic columns were packed using a slurry packing technique. Columns packed with products 5i-5m, 6i-6o, and 8c-8g used 2.1×50 mm chromatographic columns. The chromatographic system consisted of an ACQUITY UPLC®

TABLE 9

| Product | Tailing Factor for: Propranolol | Butylparaben | Naphthalene | Dipropyl- phthalate | Acenaphthene | Amitriptyline |
|---|---|---|---|---|---|---|
| 2a | 1.00 | 1.42 | 1.54 | 1.26 | 1.25 | 1.37 |
| 2b | 1.86 | 1.30 | 1.24 | 1.26 | 1.15 | 1.98 |
| 4f | 1.03 | 1.37 | 1.28 | 1.33 | 1.26 | 1.88 |
| 4g | 0.95 | 1.31 | 1.25 | 1.28 | 1.22 | 1.91 |
| 4j | 1.51 | 1.19 | 1.17 | 1.16 | 1.17 | 3.44 |
| 4k | 1.32 | 1.16 | 1.16 | 1.14 | 1.20 | 1.45 |
| 4m | 1.25 | 1.28 | 1.29 | 1.28 | 1.26 | 1.55 |
| 4n | 1.67 | 1.12 | 1.11 | 1.09 | 1.06 | 1.41 |
| 4o | 1.18 | 1.16 | 1.16 | 1.13 | 1.11 | 1.31 |
| 4p | 1.79 | 1.18 | 1.18 | 1.15 | 1.13 | 1.91 |
| 4q | 1.57 | 1.15 | 1.17 | 1.14 | 1.16 | 1.60 |
| 4r | 1.52 | 1.17 | 1.17 | 1.15 | 1.15 | 2.39 |
| 4s | 1.09 | 1.41 | 1.27 | 1.29 | 1.14 | 1.14 |
| 4t | 1.27 | 1.41 | 1.23 | 1.32 | 1.13 | 1.31 |
| 4u | 1.37 | 1.16 | 1.18 | 1.16 | 1.17 | 2.19 |
| 4z | 1.22 | 1.39 | 1.45 | 1.42 | 1.31 | 2.44 |
| 4aa | 1.61 | 1.25 | 1.30 | 1.24 | 1.22 | 2.42 |
| 4ac | 1.50 | 1.31 | 1.51 | 1.40 | 1.50 | 2.58 |
| 6e | 1.34 | 1.24 | 1.25 | 1.23 | 1.29 | 1.47 |
| 6f | 1.96 | 1.23 | 1.29 | 1.26 | 1.31 | 2.66 |
| 6g | 1.92 | 1.24 | 1.28 | 1.25 | 1.29 | 2.69 |
| 6h | 1.92 | 1.22 | 1.27 | 1.25 | 1.29 | 2.81 |
| 8a | 1.06 | 1.11 | 1.08 | 1.11 | 1.08 | 2.76 |
| Commercial <2 μm Hybrid $C_{18}$ Column | 0.88 | 1.34 | 1.24 | 1.29 | 1.14 | 1.15 |
| Commercial <2 μm Silica $C_{18}$ Column | 0.96 | 1.17 | 1.10 | 1.33 | 1.10 | 6.95 |
| Commercial <2 μm Silica $C_{18}$ Column | 0.95 | 1.35 | 1.22 | 1.32 | 1.10 | 1.77 |
| Commercial <2 μm Silica $C_{18}$ Column | 4.19 | 1.34 | 1.29 | 1.28 | 1.12 | 1.34 |

System and an ACQUITY UPLC® Tunable UV detector. Empower 2 Chromatography Data Software (Build 2154) was used for data collection and analysis. Mobile phase conditions were: 15.4 mM ammonium formate, pH 3.00±0.02/acetonitrile (65/35 v/v); flow rate: 0.25 mL/min; temperature: 30° C.; detection: 254 nm; analytes: uracil, pyrenesulfonic acid, desipramine, amitriptyline, butylparaben, and toluene. Columns 4g and 8a were tested at 23° C.

It can be seen that columns packed with particles from Examples 2-8 provide sufficient retention and resolution in the separation of neutral, polar, and basic compounds under these conditions. Relative retention is the retention time of the analyte divided by the retention time of toluene. Therefore values less than one, indicate less retention than toluene, and values greater than one, indicate more retention than toluene (relative retention is a well known parameter in the field of HPLC).

TABLE 10

| Product | Retention Factor: Toluene | Relative Retention: Pyrenesulfonic acid/ Toluene | Desipramine/ Toluene | Amitriptyline/ Toluene | Butylparaben/ Toluene |
|---|---|---|---|---|---|
| 2a | 10.95 | 0.148 | 0.275 | 0.373 | 0.965 |
| 2b | 11.73 | 0.669 | 0.180 | 0.244 | 0.975 |
| 3ac | 10.31 | 1.913 | 0.151 | 0.215 | 1.073 |
| 3ad | 9.70 | 2.137 | 0.138 | 0.197 | 1.076 |
| 4j | 11.37 | 0.491 | 0.184 | 0.250 | 1.081 |
| 4k | 10.82 | 0.216 | 0.231 | 0.311 | 1.101 |
| 4m | 10.75 | 0.227 | 0.219 | 0.297 | 1.115 |
| 4n | 10.76 | 0.245 | 0.216 | 0.291 | 1.125 |
| 4o | 10.31 | 0.219 | 0.234 | 0.316 | 1.098 |
| 4p | 11.07 | 0.177 | 0.242 | 0.328 | 1.074 |
| 4q | 9.69 | 0.354 | 0.188 | 0.250 | 1.211 |
| 4r | 11.31 | 0.154 | 0.243 | 0.329 | 1.001 |
| 4s | 11.73 | 0.180 | 0.251 | 0.339 | 1.087 |
| 4t | 11.76 | 0.199 | 0.237 | 0.319 | 1.099 |
| 4u | 11.34 | 0.229 | 0.240 | 0.326 | 1.140 |
| 4z | 12.78 | 0.208 | 0.233 | 0.316 | 1.044 |
| 4aa | 12.14 | 0.213 | 0.229 | 0.312 | 1.051 |
| 4ac | 11.46 | 0.405 | 0.177 | 0.241 | 1.026 |
| 5i | 3.64 | 5.053 | 0.244 | 0.326 | 1.151 |
| 5j | 3.28 | 5.353 | 0.223 | 0.302 | 1.179 |
| 5k | 3.86 | 3.910 | 0.331 | 0.437 | 1.114 |
| 5l | 3.18 | 5.334 | 0.228 | 0.306 | 1.171 |
| 5m | 3.34 | 5.170 | 0.228 | 0.307 | 1.163 |
| 6e | 6.26 | 0.651 | 0.190 | 0.243 | 1.218 |
| 6f | 11.91 | 1.614 | 0.194 | 0.267 | 0.865 |
| 6g | 12.09 | 0.771 | 0.244 | 0.334 | 0.854 |
| 6h | 12.18 | 0.109 | 0.305 | 0.420 | 0.849 |
| 6i | 5.75 | 0.467 | 0.339 | 0.433 | 1.119 |
| 6j | 6.78 | 0.643 | 0.246 | 0.329 | 1.156 |
| 6k | 6.48 | 0.484 | 0.258 | 0.340 | 1.111 |
| 6l | 6.48 | 0.403 | 0.293 | 0.387 | 1.081 |
| 6m | 6.51 | 0.503 | 0.248 | 0.326 | 1.147 |
| 6n | 6.44 | 0.467 | 0.260 | 0.342 | 1.138 |
| 6o | 6.38 | 0.435 | 0.280 | 0.368 | 1.105 |
| 7a | 1.41 | 1.261 | 0.290 | 0.364 | 1.258 |
| 8a | 20.48 | 0.444 | 0.169 | 0.231 | 0.808 |
| 8c | 5.09 | 4.280 | 0.386 | 0.526 | 1.129 |
| 8f | 18.35 | 0.181 | 0.152 | 0.206 | 0.997 |
| 8g | 9.73 | 0.457 | 0.210 | 0.277 | 1.112 |
| Commercial <2 μm Hybrid $C_{18}$ Column | 12.38 | 0.103 | 0.299 | 0.408 | 0.894 |
| Commercial <2 μm Silica $C_{18}$ Column | 17.24 | 0.099 | 0.289 | 0.393 | 0.924 |
| Commercial <2 μm Silica $C_{18}$ Column | 1.57 | 1.030 | 2.882 | 3.934 | 10.172 |
| Commercial <2 μm Silica $C_{18}$ Column | 9.61 | 0.170 | 0.595 | 0.888 | 1.076 |

Example 12

Samples of porous particles from Example 2-8 were evaluated for USP peak tailing factors using the mobile phase and test conditions of Example 11. The results are shown in Table 11. Peak tailing factor is a well known parameter in the field of HPLC (a lower value corresponds to reduced tailing). It is evident that columns packed with particles from Examples 2-8 provide have comparable tailing factors to commercially available $C_{18}$-columns.

TABLE 11

| | Tailing Factor for: | | | | |
|---|---|---|---|---|---|
| Product | Pyrenesulfonic acid | Desipramine | Amitriptyline | Butyl-paraben | Toluene |
| 2a | 24.51 | 1.81 | 2.21 | 1.06 | 1.03 |
| 2b | 4.60 | 1.63 | 1.81 | 1.00 | 1.01 |
| 3ac | 1.89 | 2.16 | 2.32 | 1.06 | 1.02 |
| 3ad | 1.17 | 1.69 | 1.66 | 1.03 | 1.01 |
| 4j | 1.86 | 1.65 | 2.06 | 1.04 | 1.03 |
| 4k | 1.68 | 1.63 | 1.95 | 1.06 | 1.01 |
| 4m | 1.60 | 1.45 | 1.54 | 1.14 | 1.05 |
| 4n | 1.58 | 1.36 | 1.51 | 1.00 | 0.98 |
| 4o | 1.43 | 1.46 | 1.70 | 1.04 | 1.01 |
| 4p | 1.76 | 1.54 | 1.81 | 1.05 | 1.01 |
| 4q | 1.25 | 1.40 | 1.61 | 1.03 | 0.99 |
| 4r | 1.72 | 1.69 | 2.04 | 1.05 | 1.04 |
| 4s | 1.67 | 1.90 | 2.51 | 1.03 | 1.02 |
| 4t | 1.75 | 1.82 | 2.38 | 1.02 | 1.00 |
| 4u | 1.78 | 2.05 | 2.56 | 1.05 | 1.00 |
| 4z | 2.18 | 2.84 | 3.26 | 1.08 | 1.05 |
| 4aa | 1.90 | 1.80 | 2.03 | 1.05 | 1.05 |
| 4ac | 2.24 | 1.90 | 2.04 | 1.09 | 1.07 |
| 5i | 1.46 | 1.54 | 1.49 | 1.08 | 0.97 |
| 5j | 1.27 | 1.68 | 1.61 | 1.09 | 1.12 |
| 5k | 1.50 | 1.38 | 1.36 | 1.12 | 1.05 |
| 5l | 1.65 | 1.48 | 1.47 | 1.36 | 1.23 |
| 5m | 1.19 | 1.21 | 1.17 | 1.01 | 1.01 |
| 6e | 1.37 | 1.30 | 1.35 | 1.09 | 1.05 |
| 6f | 2.30 | 1.50 | 1.66 | 1.12 | 1.07 |
| 6g | 2.83 | 1.61 | 1.79 | 1.11 | 1.06 |
| 6h | 2.35 | 1.77 | 2.05 | 1.10 | 1.07 |
| 6i | 2.60 | 1.36 | 1.38 | 1.08 | 1.12 |
| 6j | 1.51 | 1.40 | 1.39 | 1.08 | 1.10 |
| 6k | 1.88 | 1.64 | 1.64 | 1.08 | 0.85 |
| 6l | 1.49 | 1.24 | 1.29 | 0.99 | 0.83 |
| 6m | 1.39 | 1.26 | 1.29 | 1.08 | 1.09 |
| 6n | 1.46 | 1.30 | 1.32 | 1.08 | 1.04 |
| 6o | 1.53 | 1.44 | 1.43 | 1.08 | 1.07 |
| 7a | 1.67 | 1.54 | 1.57 | 1.18 | 1.15 |
| 8a | 3.40 | 1.49 | 1.62 | 1.04 | 1.05 |
| 8c | 1.30 | 1.17 | 1.16 | 1.00 | 0.92 |
| 8f | 1.55 | 1.44 | 1.57 | 1.06 | 1.05 |
| 8g | 1.61 | 1.42 | 1.45 | 1.10 | 1.08 |
| Commercial <2 μm Hybrid $C_{18}$ Column | 1.71 | 2.76 | 3.32 | 1.03 | 1.03 |
| Commercial <2 μm Silica $C_{18}$ Column | 1.40 | 2.81 | 3.58 | 1.01 | 1.02 |
| Commercial <2 μm Silica $C_{18}$ Column | 1.75 | 3.20 | 3.82 | 1.04 | — |
| Commercial <2 μm Silica $C_{18}$ Column | 1.65 | 2.20 | 2.65 | 1.06 | 1.01 |

Example 13

Samples of porous particles from Example 2, 4-8 were used for the separation of a mixture of neutral and basic compounds listed in Table 12. The 2.1×50 mm chromatographic columns were packed using a slurry packing technique. The chromatographic system consisted of an ACQUITY UPLC® System and an ACQUITY UPLC® Tunable UV detector. Empower Chromatography Data Software (Build 1154) was used for data collection and analysis. Gradient conditions: 15-65% acetonitrile (solvent B) over 4.6 minutes in 0.1% formic acid (Solvent A) followed by a 1.4 minute hold; flow rate: 0.4 mL/min; temperature: 30° C.; detection: 260 nm; basic test mix prepared in 16.7% methanol: uracil, metoprolol tartrate, papaverine, amitriptyline; neutral test mix prepared in 16.7% methanol: uracil, prednisone, caffeine. Columns packed with products 5l, 5n, 6l, 6j, 8c and 8f used 15-95% acetonitrile. Comparison Column A and B were commercially available and contained 2.7 μm $C_{18}$-bonded superficially porous silica packing material. Comparison Column C was commercially available and contained 1.7 μm porous hybrid particles of the formula $(O_{1.5}SiCH_2CH_2SiO_{1.5})(SiO_2)_4$, that was surface modified with ODTCS followed by endcapping.

Peak capacities were calculated using the average of the peak widths (4 □) over three injections. The determination of peak capacity and the problems caused by poor peak shape and resulting poor peak capacities for basic analytes in low pH gradient separations is well known in the field of HPLC and UPLC. By comparing the ratio of peak capacities for a basic analyte (amitriptyline) to a neutral analyte (prednisone) under these test conditions, a better comparison of basic analyte chromatographic performance can be made. A peak capacity ratio near one indicates similar performance of the basic and neutral analytes. A peak capacity ratio less than 0.8 indicates a substantial decrease in chromatographic performance. A peak capacity greater than one indicates an improvement in chromatographic performance for the basic analytes over the neutral analyte.

Differences due to changes in particle size can be observed by comparing the peak capacity ratios for columns packed with products 4u, 4j, and 4n. While these products are of similar Component A and B type and charges, they range in particle size from 1.8 μm (product 4u), 2.9 μm (product 4j) and 3.9 μm (product 4n). The peak capacity ratios were determined to be 0.86, 1.09 and 1.02, respectively. We can conclude that the particle size impacts performance under these conditions, especially for <2 μm packing materials. Product 4u still has significant improvements in peak capacity ratios over Comparison Columns A-D.

The impact of Component A silane additive can be observed by comparing the peak capacity ratios for columns packed with product 2a and 2d. These products are of similar size, Component B silane type and Component B silane charge. Product 2a does not contain a Component A silane additive. Product 2d was prepared with APTES charged at 0.3 μmol/m². The peak capacity ratios were determined to be 0.72 and 1.18, respectively. We can conclude that Component A silane additive type improves performance under these conditions.

Differences in Component A silane additive type can be observed by comparing the peak capacity ratios for columns packed with products 4c and 4i. These products are of similar size and Component B silane charge. While they were prepared using the same Component A silane additive charge, the Component A silane additive type was APTES for product 4c and 4PE for product 4i. The peak capacity ratios were determined to be 0.74 and 0.38, respectively. We conclude that Component A silane additive type impacts performance under these conditions.

Differences in Component A silane additive charge can be observed by comparing the peak capacity ratios for columns packed with products 4h and 4j. These products are of similar size, Component B silane type and Component B silane charge. While these products were prepared with the same Component A silane additive type, the Component A charge varied from 0.06 μmol/m² (product 4h) to 0.3 μmol/m² (product 4j). The peak capacity ratios were determined to be 0.67 and 1.09, respectively. We conclude that Component A silane additive charge impacts performance under these conditions.

Differences in Component B silane type can be observed by comparing the peak capacity ratios for columns packed with product 4k and 6e. These products are of similar size, Component A silane additive type and Component A silane additive charge. While these products were prepared with the same Component B silane charge, the Component B silane type was ODTCS for product 4k and OTCS for product 6e. The peak capacity ratios were determined to be 1.02 and 0.34, respectively. We conclude the Component B silane type impacts performance under these conditions.

Differences in Component B silane charge can be observed by comparing the peak capacity ratios for columns packed with products 4l and 4j. These products are of similar size, Component A silane additive type and charge. While these products were prepared with the same Component B silane, the Component B silane charge was 4 $\mu mol/m^2$ (product 4l) and 2 $\mu mol/m^2$ (product 4j). The peak capacity ratios were determined to be 0.45 and 1.09, respectively. We conclude the Component B silane charge impacts performance under these conditions.

TABLE 12

| Product | A<br>Amitriptyline<br>Pc | B<br>Prednisone<br>Pc | Ratio<br>A/B |
|---|---|---|---|
| 2a | 95 | 132 | 0.72 |
| 2d | 99 | 84 | 1.18 |
| 4c | 88 | 119 | 0.74 |
| 4h | 66 | 98 | 0.67 |
| 4i | 33 | 88 | 0.38 |
| 4j | 109 | 100 | 1.09 |
| 4k | 88 | 86 | 1.02 |
| 4l | 49 | 109 | 0.45 |
| 4m | 97 | 96 | 1.01 |
| 4n | 86 | 84 | 1.02 |
| 4o | 169 | 155 | 1.09 |
| 4p | 150 | 148 | 1.01 |
| 4q | 144 | 149 | 0.96 |
| 4r | 147 | 157 | 0.94 |
| 4s | 176 | 181 | 0.97 |
| 4t | 181 | 177 | 1.02 |
| 4u | 202 | 235 | 0.86 |
| 4z | 169 | 209 | 0.81 |
| 4aa | 162 | 163 | 0.99 |
| 4ac | 179 | 154 | 1.16 |
| 5i | 237 | 219 | 1.08 |
| 5j | 231 | 218 | 1.06 |
| 5k | 160 | 147 | 1.09 |
| 5l | 165 | 144 | 1.15 |
| 5m | 126 | 116 | 1.09 |
| 5n | 171 | 137 | 1.25 |
| 6a | 113 | 86 | 1.32 |
| 6b | 105 | 92 | 1.14 |
| 6c | 123 | 89 | 1.39 |
| 6d | 39 | 92 | 0.43 |
| 6e | 33 | 98 | 0.34 |
| 6f | 86 | 104 | 0.82 |
| 6g | 79 | 105 | 0.75 |
| 6h | 26 | 100 | 0.26 |
| 6i | 169 | 160 | 1.06 |
| 6j | 184 | 156 | 1.18 |
| 6o | 177 | 154 | 1.15 |
| 6p | 185 | 152 | 1.22 |
| 7a | 174 | 217 | 0.80 |
| 8c | 157 | 143 | 1.10 |
| 8f | 174 | 153 | 1.14 |
| 8g | 188 | 150 | 1.25 |
| Comparison Column A | 65 | 245 | 0.27 |
| Comparison Column B | 41 | 248 | 0.16 |
| Comparison Column C | 76 | 267 | 0.28 |

Example 14

Samples of porous particles from Example 2 and 4 were evaluated for efficiency difference upon increased loading of basic analytes. The 4.6×150 mm chromatographic columns were packed using a slurry packing technique. The chromatographic system consisted of an Alliance HPLC® System and a Waters 996 PDA detector. Empower 2 Chromatography Data Software (Build 2154) was used for data collection and analysis; injection volume 20 µL; flow rate: 1.0 mL/min; temperature: 30° C.; detection: 230 nm; analytes: amitriptyline or propranolol (prepared 60 µg/mL in mobile phase). Loading range on Table 13: 0.1 µg-2.5 µg analyte on column. In order to have comparable retention factors (0.9-2.0), mobile phase conditions were modified for separations using amitriptyline [0.05% TFA in acetonitrile/water (60/40 v/v)] and propranolol [0.05% TFA in acetonitrile/water (70/30 v/v)]. Comparison column A was commercially and contained 5 µm $C_{18}$-bonded porous silica packing material. Comparison column B was commercially available and contained 5 µm porous hybrid packing of the formula $(O_{1.5}SiCH_2CH_2SiO_{1.5})(SiO_2)_4$, that was surface modified with ODTCS followed by endcapping. Comparison columns C and D were commercially available and contained 5 µm porous silica packing that was surface modified with an organofunctional silane followed by $C_{18}$ surface modification.

The observation of decreased efficiency and worsening of peak shape for basic analytes at increased loadings when used under low pH isocratic conditions is well known in the field of HPLC and UPLC. Not limited to theory, this worsening of separation performance for basic analytes has been attributed with analyte overloading. As tabulated in Table 12, the decreased performance at increased loadings is determined as the percent loss in column efficiency between 0.1-1.2 µg or 0.1-2.5 µg loading of amitriptyline or propranolol.

Similar results were obtained for amitriptyline and propranolol at the 1.2 µg and 2.5 µg loadings. Columns that performed well on this test, including columns containing products 2c, 2g, and 4g, had a low loss in efficiency (<20%) at the 1.2 µg analyte loading. These columns had comparable performance to Comparison Columns A and C and improved performance over Comparison Columns B and D. These well-performing columns had a further decrease in efficiency between 1.2 µg and 2.5 µg loadings of approximately 100%. Other columns tested had a greater loss in efficiency (>20%) at 1.2 µg analyte loading, as well as a further decrease in efficiency between 1.2 µg and 2.5 µg loadings of approximately 25-50%.

The impact of Component A silane additive type can be observed by comparing the loss in amitriptyline efficiency (1.2 µg on column) for columns packed with product 2c and 2g. These products have the same Component B silane type and Component B silane charge. While they were prepared using the same Component A silane additive charge, the Component A silane additive was APTES for product 2c and 4PE for product 2g. The losses in amitriptyline efficiency were determined to be 4% and 13%, respectively.

The impact of Component A silane charge can be observed by comparing the loss in amitriptyline efficiency (1.2 μg on column) for columns packed with product 4c, 4f, and 4g. These products have the same Component B silane type and Component B silane charge. While they were prepared using the same Component A silane additive type, the Component A silane charge was 0.06 μmol/m$^2$ for product 4c, 0.12 μmol/m$^2$ for product 4f and 0.20 μmol/m$^2$ for product 4g. The losses in amitriptyline efficiency were determined to be 40%, 34% and 10%, respectively.

The impact of Component B silane type can be observed by comparing the loss in amitriptyline efficiency (1.2 μg on column) for columns packed with product 2c and 4b. These products have the same Component A silane additive type and Component A silane additive charge. While they were prepared using the same Component B silane charge, the Component B silane type was ODMCS for product 2c and ODTCS for product 4b. The losses in amitriptyline efficiency were determined to be 4% and 43%, respectively.

TABLE 13

| | % Loss in efficiency for | | | |
|---|---|---|---|---|
| Product | Amitriptyline (1.2 μg on Column) | Amitriptyline (2.5 μg on Column) | Propranolol (1.2 μg on Column) | Propranolol (2.5 μg on Column) |
| 2c | 4% | 8% | 5% | 10% |
| 2g | 13% | 30% | 15% | 30% |
| 4a | 61% | 77% | 57% | 75% |
| 4b | 43% | 63% | 37% | 60% |
| 4c | 40% | 59% | 41% | 59% |
| 4f | 34% | 52% | 34% | 52% |
| 4g | 10% | 18% | 8% | 11% |
| Comparison Column A | −4% | −3% | 2% | 4% |
| Comparison Column B | 51% | 72% | 47% | 71% |
| Comparison Column C | 6% | 14% | 8% | 18% |
| Comparison Column D | 20% | 44% | 26% | 49% |

Example 15

The general procedure for modifying surface silanol groups to result in the display of hydrophobic surface group and ionizable modifier that is detailed in Examples 1, 3, 5, 7 and 8 is applied to modify the surface silanol groups of different porous materials. Included in this are monolithic, spherical, granular, superficially porous and irregular materials that are silica, hybrid inorganic/organic materials, hybrid inorganic/organic surface layers on hybrid inorganic/organic, silica, titania, alumina, zirconia, polymeric or carbon materials, and silica surface layers on hybrid inorganic/organic, silica, titania, alumina, zirconia or polymeric or carbon materials. The particles size for spherical, granular or irregular materials vary from 5-500 μm; more preferably 15-100 μm; more preferably 20-80 μm; more preferably 40-60 μm. The APD for these materials vary from 30 to 2,000 Å; more preferably 40 to 200 Å; more preferably 50 to 150 Å. The SSA for these materials vary from 20 to 1000 m$^2$/g; more preferably 90 to 800 m$^2$/g; more preferably 150 to 600 m$^2$/g; more preferably 300 to 550 m$^2$/g. The TPV for these materials vary from 0.3 to 1.5 cm$^3$/g; more preferably 0.5 to 1.2 cm$^3$/g; more preferably 0.7 to 1.1 cm$^3$/g. The macropore diameter for monolithic materials vary from 0.1 to 30 μm, more preferably 0.5 to 25 μm, more preferably 1 to 20 μm.

The ionizable modifier, component A, is selected from groups used in Examples 1, 3, 5, 7 and 8 or is selected from a group having formula (I), formula (II) or formula (III) including an acidic ionizable modifier including, but not limited to, protected and unprotected versions of alkyl, aryl, and arylalkyl groups containing phosphoric, carboxylic, sulfonic, and boronic acids Preferred silane ionizable modifying reagents of formula I and II include 4-pyridyl alkyl trialkoxysilane, 3-pyridyl alkyl trialkoxysilane, 2-pyridyl alkyl trialkoxysilane, imidazole alkyl trialkoxysilane, aminoalkyl trialkoxysilane, and mono- and di-alkylaminoalkyl trialkoxysilane.

Preferred silane ionizable modifying reagents of formula III include the trisilanol, trialkoxysilane or trichlorosilane, the protected and deprotected acid forms, chloro forms, as well as salts of sulfonic acid alkyl silanes, sulfonic acid phenylalkyl silanes, sulfonic acid benzylalkyl silanes, sulfonic acid phenyl silanes, sulfonic acid benzyl silanes, carboxylic acid alkyl silanes, carboxylic acid phenylalkyl silanes, carboxylic acid benzylalkyl silanes, carboxylic acid phenyl silanes, carboxylic acid benzyl silanes, phosphoric acid alkyl silanes, phosphonic acid phenylalkyl silanes, phosphonic acid benzylalkyl silanes, phosphonic acid phenyl silanes, phosphonic acid benzyl silanes, boronic acid alkyl silanes, boronic acid phenylalkyl silanes, boronic acid benzylalkyl silanes, boronic acid phenyl silanes, boronic acid benzyl silanes.

Example 16

Residual silanol groups from select materials prepared in Example 15 are further reacted following protocols detailed in Examples 2, 4, and 6.

Example 17

In a general procedure propanol hybrid surrounded hybrid particles (product 17a) were prepared in a multistep procedure as follows;

Acetoxypropyltrimethoxysilane (700 g, Gelest Inc., Morrisville, Pa.) was mixed with ethanol (374 g, anhydrous, J. T. Baker, Phillipsburgh, N.J.) and an aqueous solution of 0.01M Acetic Acid (22 g, J. T. Baker, Phillipsburgh, N.J.) in a flask. The resulting solution was agitated and refluxed for 16 hours in an atmosphere of argon or nitrogen. Alcohol was removed from the flask by distillation at atmospheric pressure. Residual alcohol and volatile species were removed by heating at 110° C. for 17 hours in a sweeping stream of argon or nitrogen. The resulting polyorganoalkoxy siloxanes was a clear viscous liquid had a viscosity of 95 cP.

This polyorganoalkoxy siloxanes was added to a suspension of BEH porous hybrid particles (20 g, Waters Corporation, Milford, Mass.; 6.5% C; SSA=190 m$^2$/g; SPV=0.80 cm$^3$/g; APD=155 Å) of the formula $(O_{1.5}SiCH_2CH_2SiO_{1.5})(SiO_2)_4$ (prepared following the method described in U.S. Pat. No. 6,686,035) in dry toluene (Fisher Scientific, Fairlawn, N.J.; 5 mL/g) This reaction was heated at 80° C. for one hour and 110° C. for 20 hours using a Dean-Stark trap to remove residual water. The reaction was cooled to room temperature and particles were isolated on 0.5 μm filtration paper and washed repeatedly using ethanol (anhydrous, J. T. Baker, Phillipsburgh, N.J.). The material was then heated to 50° C. in a suspension with ethanol (3 mT anhydrous, J. T. Baker, Phillipsburgh, N.J.), deionized water (7 mL/g) and 30% ammonium hydroxide (20 g; J. T. Baker, Phillipsburgh, N.J.) for 4 hours. The reaction was then cooled and the product was filtered and washed successively with water and methanol (Fisher Scientific, Fairlawn, N.J.). The product was then dried at 80° C. under reduced pressure for 16 hours.

The particles were then mixed with an aqueous solution of 0.3 M tris(hydroxymethyl)aminomethane (TRIS, Aldrich Chemical, Milwaukee, Wis.) at a slurry concentration of 5 mL/g. The pH of the resultant slurry was adjusted to 9.8 using acetic acid (J. T. Baker, Phillipsburgh, N.J.). The slurry was then enclosed in a stainless steel autoclave and heated to 155° C. for 20 hours. After cooling the autoclave to room temperature, the product was were isolated on 0.5 μm filtration paper and washed with water and methanol (Fisher Scientific, Suwanee, Ga.). The particles were then dried at 80° C. under vacuum for 16 hours.

The particles were then dispersed in a 1 molar hydrochloric acid solution (Aldrich, Milwaukee, Wis.) for 20 h at 98° C. The particles were isolated on 0.5 μm filtration paper and washed with water to a neutral pH, followed by acetone (HPLC grade, Fisher Scientific, Fairlawn, N.J.). The particles were dried at 80° C. under vacuum for 16 h. Products obtained by this approach have 8.1-8.6% C; SSA=150-166 m$^2$/g; SPV=0.6-0.7 cm$^3$/g; APD=134-145 Å). Structural analysis was performed using NMR. spectroscopy. Surface coverage of propanol groups, determined by the difference in particle % C using elemental analysis, was 3.2-3.8 μmol/m$^2$.

Example 18

Propanol hybrid surrounded hybrid particles from Example 17 were modified with octadecyl isocyanate (ODIC, Aldrich Chemical), pentafluorophenyl isocyanate (PFPIC, Aldrich Chemical), 2,2-Diphenylethyl isocyanate (DPEIC, Aldrich Chemical), 4-cyanophenyl isocyanate (4CPIC, Aldrich Chemical), or 3-cyanophenyl isocyanate (3CPIC, Aldrich Chemical) in dry toluene (5 mL/g, J. T. Baker) under an argon blanket. The suspension was heated to reflux (110° C.) for 16 h and then cooled to <30° C. The particles were transferred to a filter apparatus and washed exhaustively with toluene and acetone. The material was then treated as detailed in the hydrolysis section of Example 3, or the material was heated for an hour at 50° C. in a 1:1 v/v mixture of acetone and 1% trifluoroacetic acid (Aldrich, Milwaukee, Wis.) solution (10 mL/g particles) (Hydrolysis D). The reaction was then cooled and the product was filtered and washed successively with acetone and toluene (heated at 70° C.). The product was then dried at 70° C. under reduced pressure for 16 hours. Reaction data is listed in Table 14. The surface coverage of carbamate groups was determined by the difference in particle % C before and after the surface modification as measured by elemental analysis.

TABLE 14

| | | | | Component B | | | | Carbamate |
|---|---|---|---|---|---|---|---|---|
| Product | dp (μm) | Particles (g) | Isocyanate | Isocyanate mass (g) | Isocyanate Charge (μmol/m$^2$) | Hydrolysis Type | % C | Surface Coverage (μmol/m$^2$) |
| 18a | 3.0 | 25 | ODIC | 11.9 | 10.0 | B | 15.93 | 2.55 |
| 18b | 3.0 | 60 | ODIC | 28.9 | 10.0 | B | 15.86 | 2.47 |
| 18c | 3.0 | 40 | ODIC | 19.3 | 10.0 | B | 15.28 | 2.26 |
| 18d | 3.0 | 40 | ODIC | 19.3 | 10.0 | B | 15.28 | 2.26 |
| 18e | 4.0 | 50 | ODIC | 27.3 | 11.8 | B | 15.49 | 2.47 |
| 18f | 3.5 | 25 | ODIC | 12.0 | 10.0 | B | 14.58 | 2.07 |
| 18g | 3.5 | 25 | ODIC | 6.0 | 5.0 | B | 13.04 | 1.52 |
| 18h | 3.5 | 15 | ODIC | 7.2 | 10.0 | B | 14.3 | 2.00 |
| 18i | 3.5 | 15 | ODIC | 7.2 | 10.0 | B | 14.55 | 2.09 |
| 18j | 3.5 | 15 | ODIC | 7.2 | 10.0 | B | 14.55 | 2.09 |
| 18k | 3.5 | 10 | ODIC | 4.8 | 10.0 | B | 13.64 | 1.76 |
| 18l | 3.5 | 10 | ODIC | 4.8 | 10.0 | B | 13.78 | 1.81 |
| 18m | 3.5 | 10 | ODIC | 4.8 | 10.0 | B | 13.87 | 1.85 |
| 18n | 4.9 | 10 | ODIC | 3.6 | 8.0 | B | 12.97 | 1.58 |
| 18o | 4.9 | 33 | ODIC | 12.4 | 8.0 | B | 14.45 | 2.12 |
| 18p | 3.5 | 50 | ODIC | 18.9 | 8.0 | B | 14.82 | 2.19 |
| 18q | 3.5 | 50 | ODIC | 18.9 | 8.0 | B | 14.78 | 2.18 |
| 18r | 3.5 | 50 | ODIC | 18.9 | 8.0 | B | 14.95 | 2.24 |
| 18s | 3.5 | 60 | ODIC | 23.6 | 8.0 | B | 15.10 | 2.20 |
| 18t | 4.9 | 60 | ODIC | 22.6 | 8.0 | B | 15.24 | 2.35 |
| 18u | 4.9 | 20 | PFPIC | 6.7 | 10.0 | D | 12.24 | 3.98 |
| 18v | 3.5 | 12 | DPEIC | 4.3 | 10.0 | C | 14.05 | 2.36 |
| 18w | 3.0 | 45 | 4CPIC | 10.4 | 10.0 | D | 13.01 | 3.63 |
| 18x | 4.9 | 40 | 4CPIC | 3.1 | 3.45 | C | 11.88 | 2.90 |
| 18y | 4.9 | 40 | 3CPIC | 3.1 | 3.45 | C | 11.96 | 2.97 |

Example 19

The materials of Example 18 were further modified aminopropyltriethoxysilane (APTES, Gelest Inc., Morrisville, Pa.), 2-(4-pyridylethyl)triethoxysilane (4PE, Gelest Inc., Morrisville, Pa.) or 2-(2-pyridylethyl)trimethoxysilane (2PE, Gelest Inc., Morrisville, Pa.). in refluxing toluene (5 mL/g) for 20 hours. Products 19a and 19b were reacted for 4 hours. The reaction was then cooled and the product was filtered and washed successively with water, toluene, 1:1 v/v acetone/water and acetone (all solvents from J. T. Baker). The material was then treated as detailed in the hydrolysis section of Example 3, or the material was heated for an hour at 50° C. in a 1:1 v/v mixture of acetone and 1% trifluoroacetic acid (Aldrich, Milwaukee, Wis.) solution (10 mL/g particles) (Hydrolysis D). The reaction was then cooled and the product was filtered and washed successively water, toluene, 1:1 v/v acetone/water and acetone and then dried at 70° C. under reduced pressure for 16 hours. Reaction data is listed in Table 15.

TABLE 15

| Product | Precursor | Particles (g) | Silane Additive | Silane mass (g) | Silane Additive Charge (µmol/m²) | Charge Molar Ratio B/A | Hydrolysis Type | % C |
|---|---|---|---|---|---|---|---|---|
| 19a | 18a | 10 | APTES | 0.01 | 0.03 | 333 | none | 16.82 |
| 19b | 18a | 10 | APTES | 0.02 | 0.05 | 200 | none | 16.82 |
| 19c | 18b | 30 | 4PE | 0.04 | 0.03 | 333 | none | 15.79 |
| 19d | 18b | 15 | 4PE | 0.04 | 0.06 | 167 | A | 15.81 |
| 19e | 18b | 20 | 4PE | 0.04 | 0.05 | 200 | B | 15.82 |
| 19f | 18b | 30 | 4PE | 0.08 | 0.06 | 167 | none | 15.79 |
| 19g | 18b | 17 | 4PE | 0.08 | 0.11 | 91 | A | 15.78 |
| 19h | 18b | 20 | 4PE | 0.08 | 0.09 | 111 | B | 15.79 |
| 19i | 18b | 30 | 4PE | 0.04 | 0.03 | 333 | B | 15.79 |
| 19j | 18b | 30 | 4PE | 0.08 | 0.06 | 167 | A | 15.79 |
| 19k | 18c | 30 | 4PE | 0.08 | 0.06 | 167 | B | 15.18 |
| 19l | 18d | 30 | 4PE | 0.08 | 0.06 | 167 | A | 15.22 |
| 19m | 18d | 30 | 4PE | 0.08 | 0.06 | 167 | D | 15.18 |
| 19n | 18d | 10 | 4PE | 0.01 | 0.03 | 439 | B | 15.17 |
| 19o | 18e | 10 | 4PE | 0.25 | 0.59 | 20 | B | 15.00 |
| 19p | 18e | 10 | APTES | 0.01 | 0.04 | 295 | B | 15.34 |
| 19q | 18e | 10 | APTES | 0.004 | 0.01 | 1180 | B | 15.32 |
| 19r | 18f | 25 | 2PE | 0.04 | 0.04 | 250 | B | 14.73 |
| 19s | 18g | 24 | 2PE | 0.04 | 0.04 | 125 | B | 13.32 |
| 19t | 18h | 10 | 4PE | 0.09 | 0.20 | 50 | C | 14.20 |
| 19u | 18i | 10 | 4PE | 0.13 | 0.30 | 33 | C | 14.36 |
| 19v | 18k | 9 | 4PE | 0.11 | 0.30 | 33 | C | 13.78 |
| 19w | 18l | 8 | 4PE | 0.04 | 0.10 | 100 | C | 13.63 |
| 19x | 18m | 9 | 4PE | 0.19 | 0.50 | 20 | C | 13.87 |
| 19y | 18n | 9 | 2PE | 0.10 | 0.30 | 27 | C | 13.27 |
| 19z | 18o | 30 | 4PE | 0.39 | 0.30 | 27 | C | 14.41 |
| 19aa | 18p | 30 | 4PE | 0.39 | 0.30 | 27 | C | 14.82 |
| 19ab | 18q | 30 | 4PE | 0.39 | 0.30 | 27 | C | 14.79 |
| 19ac | 18r | 30 | 4PE | 0.39 | 0.30 | 27 | C | 14.81 |
| 19ad | 18s | 55 | 4PE | 0.74 | 0.30 | 27 | C | 14.87 |
| 19ae | 18t | 30 | 4PE | 0.39 | 0.30 | 27 | C | 14.62 |
| 19af | 18u | 6 | 4PE | 0.01 | 0.03 | 333 | none | 11.69 |
| 19ag | 18v | 9 | 4PE | 0.12 | 0.31 | 32 | C | 14.07 |
| 19ah | 18w | 8 | 4PE | 0.01 | 0.03 | 347 | none | 12.77 |
| 19ai | 18x | 10 | 4PE | 0.21 | 0.51 | 7 | C | 11.83 |
| 19aj | 18x | 10 | 4PE | 0.12 | 0.29 | 12 | C | 11.80 |
| 19ak | 18y | 10 | 4PE | 0.21 | 0.51 | 7 | C | 11.93 |
| 19al | 18y | 10 | 4PE | 0.12 | 0.29 | 12 | C | 11.87 |

Example 20

Selected materials of Example 19 were further modified by endcapping as detailed in Example 4. Data is listed in Table 16.

TABLE 16

| Product | Precursor | % C |
|---|---|---|
| 20a | 19i | 16.73 |
| 20b | 19i | 16.72 |
| 20c | 19j | 16.40 |
| 20d | 19j | 16.67 |
| 20e | 19k | 16.11 |
| 20f | 19l | 15.84 |
| 20g | 19m | 16.06 |
| 20h | 19n | 15.46 |
| 20i | 19o | 15.67 |
| 20j | 19p | 16.00 |
| 20k | 19q | 16.18 |
| 20l | 19r | 15.50 |
| 20m | 19s | 13.91 |

Example 21

Propanol hybrid surrounded hybrid particles from Example 17 were modified with 2-(4-pyridylethyl)triethoxysilane (4PE, Gelest Inc., Morrisville, Pa.) in refluxing toluene (5 mL/g) for 20 hours. The reaction was then cooled and the product was filtered and washed successively with water, toluene, 1:1 v/v acetone/water and acetone (all solvents from J. T. Baker). The material was then treated as hydrolysis C of Example 3. The reaction was then cooled and the product was filtered and washed successively water, toluene, 1:1 v/v acetone/water and acetone. Selected products were then dried at 70° C. under reduced pressure for 16 hours. Reaction data is listed in Table 17.

TABLE 17

| Product | dp (µm) | Particles (g) | Silane mass (g) | Silane Additive Charge (µmol/m²) | Hydrolysis Time (hr) | Vacuum Dried (Y/N) |
|---|---|---|---|---|---|---|
| 21a | 3.6 | 35 | 0.15 | 0.10 | 2 | Y |
| 21b | 3.6 | 35 | 0.30 | 0.20 | 2 | Y |
| 21c | 4.8 | 31 | 0.13 | 0.10 | 2 | Y |
| 21d | 4.8 | 31 | 0.26 | 0.20 | 2 | Y |
| 21e | 3.4 | 35 | 0.31 | 0.20 | 2 | Y |
| 21f | 4.8 | 35 | 0.30 | 0.20 | 2 | Y |
| 21g | 4.8 | 35 | 0.30 | 0.20 | 2 | Y |
| 21h | 3.4 | 35 | 0.31 | 0.20 | 2 | Y |
| 21i | 3.6 | 35 | 0.30 | 0.20 | 2 | Y |
| 21j | 4.8 | 25 | 0.31 | 0.30 | 20 | N |

TABLE 17-continued

| Product | dp (μm) | Particles (g) | Component A Silane mass (g) | Silane Additive Charge (μmol/m²) | Hydrolysis Time (hr) | Vacuum Dried (Y/N) |
|---|---|---|---|---|---|---|
| 21k | 4.8 | 35 | 0.16 | 0.15 | 20 | N |
| 21l | 4.8 | 30 | 0.19 | 0.15 | 20 | N |
| 21m | 3.6 | 35 | 0.23 | 0.15 | 20 | N |

Example 22

Products from Example 21 were modified with isocyanate as detailed in Example 18 using hydrolysis C. Reaction data is listed in Table 18.

TABLE 18

| Product | Precursor | Particles (g) | Component B Isocyanate | Isocyanate mass (g) | Isocyanate Charge (μmol/m²) | Charge Molar Ratio B/A | % C | Carbamate Surface Coverage (μmol/m²) |
|---|---|---|---|---|---|---|---|---|
| 22a | 21a | 20 | ODIC | 7.60 | 8.00 | 80 | 14.86 | 2.21 |
| 22b | 21b | 20 | ODIC | 7.60 | 8.00 | 40 | 14.92 | 2.23 |
| 22c | 21c | 20 | ODIC | 7.30 | 8.00 | 80 | 14.62 | 2.20 |
| 22d | 21d | 20 | ODIC | 7.30 | 8.00 | 40 | 14.73 | 2.24 |
| 22e | 21e | 20 | ODIC | 7.85 | 8.00 | 40 | 14.83 | 2.10 |
| 22f | 21f | 20 | ODIC | 7.52 | 8.00 | 40 | 14.55 | 2.09 |
| 22g | 21h | 20 | ODIC | 7.85 | 8.00 | 40 | 14.69 | 2.05 |
| 22h | 21i | 20 | ODIC | 7.56 | 8.00 | 40 | 14.33 | 2.01 |
| 22i | 21j | 20 | ODIC | 7.28 | 8.00 | 27 | 14.00 | 1.96 |
| 22j | 21k | 20 | ODIC | 7.28 | 8.00 | 53 | 14.04 | 1.98 |
| 22k | 21l | 30 | ODIC | 10.92 | 8.00 | 53 | 13.99 | 1.96 |
| 22l | 21m | 35 | ODIC | 13.24 | 8.00 | 53 | 14.18 | 1.96 |
| 22m | 21a | 10 | 3CPIC | 0.80 | 3.47 | 35 | 10.08 | 1.32 |
| 22n | 21b | 10 | 3CPIC | 0.80 | 3.47 | 17 | 10.22 | 1.43 |

Example 23

The concentration of surface pyridyl groups (ionizable modifier) were quantified for select materials prepared in Examples 3, 4, 21 and 22 using the following procedure. 2-(4-pyridylethyl)triethoxysilane (1.12 μmol, Gelest Inc., Morrisville, Pa.) in methanol (0.4 mL, HPLC grade) was added to a sample (0.2000 g) from Example 3, 21 or 22. The sample was then digested using sodium hydroxide solution (4.0 mL, 2.5 M) at 64° C. for 60 minutes. The sample was filtered through a Millex-LCR filter (0.45 μm, 25 mm, Millipore) and was extracted with hexane (HPLC grade). The aqueous layer was then analyzed using a UV/Visible spectrophotometer (300-240 nM, 0.1 nM interval, scan speed=120 nM/min, slit width=2 nM). The concentration of pyridyl groups were calculated using the absorbance at two wavelengths with corrections made for base particle contribution to absorbance. The results are listed in Table 19. These results indicate a reduced concentration of pyridylethyl groups (component A) on the surface than was charged. Using the determined coverage of component B we can determine the determined surface coverage ratio of B/A. The result of this is a larger range of surface coverage ratio of B/A (8-190) than molar charge ratio (6-80).

TABLE 19

| Product | Component A Ionizable Modifier Charge (μmol/m²) | Component B Hydrophobic Group Charge (μmol/m²) | Charge Molar Ratio B/A | Component A Ionizable Modifier Coverage (μmol/m²) | Component B Hydrophobic Group Coverage (μmol/m²) | Surface Coverage Ratio B/A |
|---|---|---|---|---|---|---|
| 3ah | 3.70 | — | — | 0.890 | — | — |
| 4v | 0.35 | 2.53 | 7 | 0.160 | 2.45 | 15 |
| 4w | 0.35 | 2.07 | 6 | 0.250 | 2.09 | 8 |
| 4x | 0.25 | 2.53 | 10 | 0.140 | 2.51 | 18 |
| 4y | 0.25 | 2.07 | 8 | 0.210 | 2.05 | 8 |
| 8b | 0.30 | 2.3 | 8 | 0.28 | 2.53 | 9 |
| 8f | 0.30 | 2.3 | 8 | 0.27 | 2.53 | 9 |
| 21a | 0.10 | — | — | 0.020 | — | — |
| 21b | 0.20 | — | — | 0.029 | — | — |
| 21c | 0.10 | — | — | 0.020 | — | — |
| 21d | 0.20 | — | — | 0.025 | — | — |
| 21e | 0.20 | — | — | 0.017 | — | — |
| 21f | 0.20 | — | — | 0.013 | — | — |
| 21g | 0.20 | — | — | 0.011 | — | — |
| 21h | 0.20 | — | — | 0.019 | — | — |
| 21i | 0.20 | — | — | 0.031 | — | — |
| 22a | 0.10 | 8.00 | 80 | 0.019 | 2.21 | 116 |
| 22b | 0.20 | 8.00 | 40 | 0.028 | 2.23 | 80 |

TABLE 19-continued

| Product | Component A Ionizable Modifier Charge (μmol/m²) | Component B Hydrophobic Group Charge (μmol/m²) | Charge Molar Ratio B/A | Component A Ionizable Modifier Coverage (μmol/m²) | Component B Hydrophobic Group Coverage (μmol/m²) | Surface Coverage Ratio B/A |
|---|---|---|---|---|---|---|
| 22c | 0.10 | 8.00 | 80 | 0.018 | 2.20 | 122 |
| 22d | 0.20 | 8.00 | 40 | 0.022 | 2.24 | 102 |
| 22e | 0.20 | 8.00 | 40 | 0.015 | 2.10 | 140 |
| 22f | 0.20 | 8.00 | 40 | 0.011 | 2.09 | 190 |
| 22g | 0.20 | 8.00 | 40 | 0.017 | 2.05 | 121 |
| 22h | 0.20 | 8.00 | 40 | 0.029 | 2.01 | 69 |
| 22i | 0.30 | 8.00 | 27 | 0.038 | 1.96 | 52 |
| 22j | 0.15 | 8.00 | 53 | 0.028 | 1.98 | 71 |
| 22k | 0.15 | 8.00 | 53 | 0.030 | 1.96 | 65 |
| 22l | 0.15 | 8.00 | 53 | 0.025 | 1.96 | 78 |

Example 24

To a suspension of 5 μm BEH porous hybrid particles (25 g, Waters Corporation, Milford, Mass.; 6.5% C; SSA=190 m²/g; SPV=0.80 cm³/g; APD=155 Å) of the formula $(O_{1.5}SiCH_2CH_2SiO_{1.5})(SiO_2)_4$ (prepared following the method described in U.S. Pat. No. 6,686,035) in dry toluene (250 mL, Fisher Scientific) was added Component A, 2-(4-pyridylethyl)triethoxysilane (0.2182 g, 0.2 μmol/m², Gelest Inc., Morrisville, Pa.), before following the general procedure for preparing propanol hybrid surrounded hybrid particles detailed in Example 17. Product 24a of this reaction incorporated a low level of ionizable modifier during the formation of the propanol hybrid surrounded hybrid particles having 8.3% C and 3.70 μmol/m² propanol groups.

Example 25

A portion product 24a (16.2 g) from Example 24 was reacted with Component B, octadecyl isocyanate (7.51 g, 10 μmol/m²), in a similar process detailed in Example 18, using hydrolysis C. The product of this reaction had 14.27% C and 2.00 μmol/m² carbamate groups. This resulting product 25a had a molar charge ratio of B/A of 50.

Example 26

The general procedure to prepare a propanol hybrid surrounded core material, detailed in Examples 17 are applied to different porous materials. Included in this are core materials detailed in Example 15.

Example 27

Modification of the surface of these propanol hybrid surrounded core materials prepared in Example 26 with a component B hydrophobic group is accomplished using silane approaches detailed in Examples 1, 3 or 5 or with isocyanate approaches detailed in Examples 18.

Further modification of the surface of these materials with a component A ionizable modifier is accomplished using silane approached detailed in Examples 19. Alternatively the surface propanol groups is reacted with ionizable modifying reagents of formula type I, or II where Z is isocyanate or 1-carbamoyl imidazole, following the approach detailed in Example 18. Preferred ionizable modifiers include 4-pyridyl alkylisocyanates, 3-pyridyl alkylisocyanates, 2-pyridyl alkylisocyanates, imidazole alkylisocyanates, 1-(N-(4-pyridyl alkyl)carbamoyl)imidazole, 1-(N-(3-pyridyl alkyl)carbamoyl)imidazole, 1-(N-(2-pyridyl alkyl)carbamoyl)imidazole, and 1-(N-(imidazol-1-yl-alkyl)carbamoyl) imidazole.

Alternatively the surface propanol groups is reacted with ionizable modifying reagents of formula III where Z is isocyanate or 1-carbamoyl imidazole, following the approach detailed in Example 18. Preferred ionizable modifiers include acid-protected and acid-non-protected versions of isocyanato-alkyl sulfonic acid, isocyanato-alkyl carboxylic acid, isocyanato-alkyl phosphoric acid, isocyanato-alkyl boronic acid, [(imidazole-1-carbonyl)-amino]-alkyl sulfonic acid, [(imidazole-1-carbonyl)-amino]-alkyl carboxylic acid, [(imidazole-1-carbonyl)-amino]alkyl phosphoric acid, [(imidazole-1-carbonyl)-amino]-alkyl boronic acid, isocyanato-aryl sulfonic acid, isocyanato-aryl carboxylic acid, isocyanato-aryl phosphoric acid, isocyanato-aryl boronic acid, [(imidazole-1-carbonyl)-amino]aryl sulfonic acid, [(imidazole-1-carbonyl)-amino]-aryl carboxylic acid, [(imidazole-1-carbonyl)-amino]-aryl phosphoric acid, [(imidazole-1-carbonyl)-amino]-aryl boronic acid, isocyanato-aryl alkyl sulfonic acid, isocyanato-aryl alkyl carboxylic acid, isocyanato-aryl alkyl phosphoric acid, isocyanato-aryl alkyl boronic acid, [(imidazole-1-carbonyl)-amino]-aryl alkyl sulfonic acid, [(imidazole-1-carbonyl)-amino]-aryl alkyl carboxylic acid, [(imidazole-1-carbonyl)-amino]-aryl alkyl phosphoric acid, [(imidazole-1-carbonyl)-amino]-aryl alkyl boronic acid, isocyanato-alkyl aryl alkyl sulfonic acid, isocyanato-alkyl aryl alkyl carboxylic acid, isocyanato-alkyl aryl alkyl phosphoric acid, isocyanato-alkyl aryl alkyl boronic acid, [(imidazole-1-carbonyl)-amino]-alkyl aryl alkyl sulfonic acid, [(imidazole-1-carbonyl)-amino]-alkyl aryl alkyl carboxylic acid, [(imidazole-1-carbonyl)-amino]-alkyl aryl alkyl phosphoric acid, and [(imidazole-1-carbonyl)-amino]-alkyl aryl alkyl boronic acid.

Example 28

Modification of the surface of these propanol hybrid surrounded core materials as detailed in Example 27, but the ionizable group is reacted before the hydrophobic group.

Example 29

The general procedure to prepare a propanol hybrid surrounded core material having an ionizable group, detailed in Examples 24 is applied to different core materials. Included in this are core materials detailed in Example 15. Modification of the surface of these propanol hybrid surrounded core materials with a hydrophobic group is accomplished using silane approaches detailed in Examples 1, 3 or 5 or is accomplished using isocyanate approaches detailed in Examples 18.

Example 30

Further modification of the surface of materials prepared in Examples 27-29 is accomplished using approaches detailed in Examples 2, 4, 6, and 20 or surface propanol groups are future reacted with alkyl isocyanate or aryl isocyanates as detailed in Example 18.

Example 31

The general approach to prepare a hybrid surrounded hybrid particle is used to prepare new hybrid surrounded materials that have reactive surface groups other than silanols and propanol groups, following a general approach detailed in Example 17 and 24, using core materials detailed in Example 15. When hybrid surfaces are prepared that have vinyl, haloalkyl, aminoalkyl, epoxy or phenyl groups, different reactions are performed to attach the hydrophobic or ionizable modifier. Vinyl groups are modified using radical addition, metathesis, epoxidation and hydrosilylation. Haloalkyl groups are modified by nucleophillic displacement and Grinard reactions Aminoalkyl groups are reacted with acids, isocyanates or nucleophillic displacement. Epoxy groups are hydrolyzed to present surface alcohol groups, or reactions with amines. Phenyl groups are substituted with chloromethyl, sulfonic or nitro groups. Ionizable modifying reagents of formula type I, II or III result where Z represents a chemically reactive group, including (but not limited to) a silane, silanol, ether, amine, alkylamine, dialkylamine, isocyanate, acyl chloride, triflate, isocyanate, thiocyanate, imidazole carbonate, 1-carbamoyl imidazole, NHS-ester, carboxylic acid, ester, epoxide, alkyne, alkene, azide, —Br, —Cl, or —I.

Further modifications of these materials is accomplished as detailed in Examples 27-30.

Example 32

In a general procedure propanol surrounded particles containing an ionizable modifier are prepared in a multistep procedure. Products 3af-3ah from Example 3 are reacted with acetoxypropyltrichlorosilane in dry toluene using imidazole. The reaction is heated to reflux for 20 hours before cooling, filtering, and washing with toluene, 1:1 v/v acetone/water, and acetone. The material is refluxed acetone/aqueous 0.1M ammonium bicarbonate (pH 10) solution for 20 hours at 50° C. The reaction is cooled and the product is filtered and is washed successively with toluene, 1:1 v/v acetone/water, and acetone. The product is then hydrolyzed in 1 N HCl for 20 hours at an elevated temperature. The reaction is cooled and the product is filter and is washed with water and acetone. The product is dried at 80° C. under reduced pressure for 16 hours. Products prepared by this approach have surface pyridylethyl and propanol groups.

Example 33

The general procedure to prepare a propanol hybrid surrounded core material using acetoxypropyltrichlorosilane or a polyorganoalkoxy siloxane, having an initial modification with ionizable modifier is applied to different core materials. Included in this are core materials detailed in Example 15. The modification of these core materials with an ionizable modifier is accomplished using silane approaches detailed in Examples 1, 3 or 5, or is accomplished using ionizable modifying reagents of formula I, II or III detailed in Example 15. The general approach to modify core materials with acetoxypropyltrichlorosilane is detailed in Example 33. The general approach to modify core materials with acetoxypropyltrichlorosilane is detailed in Example 17.

Example 34

Acetoxypropyltrimethoxysilane (323 g, Gelest Inc., Morrisville, Pa.) was mixed with 2-(4-pyridylethyl)triethoxysilane (13.04 g, Gelest Inc., Morrisville, Pa.), ethanol (218 g, anhydrous, J. T. Baker, Phillipsburgh, N.J.) and an aqueous solution of 2.2 M Acetic Acid (26 g, J. T. Baker, Phillipsburgh, N.J.) in a flask. The resulting solution was agitated and refluxed for 16 hours in an atmosphere of argon or nitrogen. Alcohol was removed from the flask by distillation at atmospheric pressure. Residual alcohol and volatile species were removed by heating at 110° C. for 5 hours in a sweeping stream of argon or nitrogen. The resulting polyorganoalkoxy siloxane, Product 34a, was a clear viscous liquid had a viscosity of 27 cP.

Example 35

In a general procedure, propanol hybrid surrounded core materials containing an ionizable modifier are prepared by a multistep procedure where Product 34a from Example 34 is used in place of the polyorganoalkoxy siloxane in Example 17.

Alternatively this general procedure to prepare add the ionizable modifier before the preparation of the propanol hybrid surrounded core material is applied to different core materials. Included in this are core materials detailed in Example 15.

Example 36

Modification of the surface of materials prepared in Examples 31-33 and 35 with a hydrophobic group is accomplished using silane approaches detailed in Examples 1, 3 or 5 or with isocyanate approaches detailed in Examples 18.

Example 37

Secondary surface modification of materials prepared in Examples 36 is accomplished using approaches detailed in Examples 2, 4, 6, and 20 or with isocyanate approaches detailed in Examples 18

Example 38

Products prepared in Examples 15, 16, 19-22, 24-25, 27-33, and 35-37 are chromatographically evaluated as detailed in Examples 9-14. Concentration of ionizable modifier are determined as detailed in Example 23.

Example 39

Samples of porous particles from Product 4aa and a 3 µm commercially available $C_{18}$ column were evaluated for changes in retention of ionized analytes when exposed to mobile phases of different pH. The 2.1×50 mm chromatographic columns were packed using a slurry packing technique. The chromatographic system consisted of an ACQUITY UPLC® System and an ACQUITY UPLC® Tunable UV detector. Empower Chromatography Data Software (Build 1154) was used for data collection and analysis; injection volume 2 µL; flow rate: 0.8 mL/min; temperature: 30° C.; detection: 260 nm; analytes: metoprolol and amitriptyline. Data were compared before (initial) and after (final) 7 cycles; each cycle included alternately 7 injections in a 0.1% formic acid/acetonitrile gradient followed by 17 injections in a 10 mM ammonium bicarbonate (pH 10)/acetonitrile gradient. Both acidic and pH 10 gradients ran from 5 to 95% acetonitrile in 2.5 minutes.

As shown in FIG. 1, changes in retention of ionized analytes when exposed to mobile phases of different pH is a problem that is known in the art. The commercially available $C_{18}$ column experienced a 7% change in retention for amitriptyline, while Product 4aa experienced a 0.4% change in retention for amitriptyline under these conditions. While not limited to theory, it has been proposed that slow surface equilibration is to blame. Because conventional high-purity reversed-phase columns have much reduced surface charge at low pH, very small changes in surface charge may cause a large change in retention for ionized analytes. This effect is exacerbated by the use of low-ionic-strength mobile phases. The change in selectivity is not due to loss of bonded phase because the change is reversible, and no loss of retention is observed for neutral analytes. Storage and/or equilibration of columns in the low-pH mobile phase (allowing time for diffusion) will eventually return them to their original selectivity. This slow equilibration does not occur at elevated pH because of the relatively high concentration of deprotonated silanols.

These data indicate that, unlike the commercially available $C_{18}$ column, Product 4aa can be used in method development screens of high and low pH gradient conditions with the assurance that the method will work on an unused column.

Example 40

Similar to Example 13, samples of porous particles from Example 4j and a commercially available $C_{18}$ column were used for the separation of a mixture of neutral and basic compounds. The basic test mix prepared included uracil, metoprolol tartate, labetalol, amitriptyline and the neutral test mix included uracil, prednisone, caffeine. The comparison $C_{18}$ column was commercially available and contained 3.5 µm porous hybrid particles of the formula $(O_{1.5}SiCH_2CH_2SiO_{1.5})(SiO_2)_4$ that was surface modified with ODTCS followed by endcapping.

Figure 2:
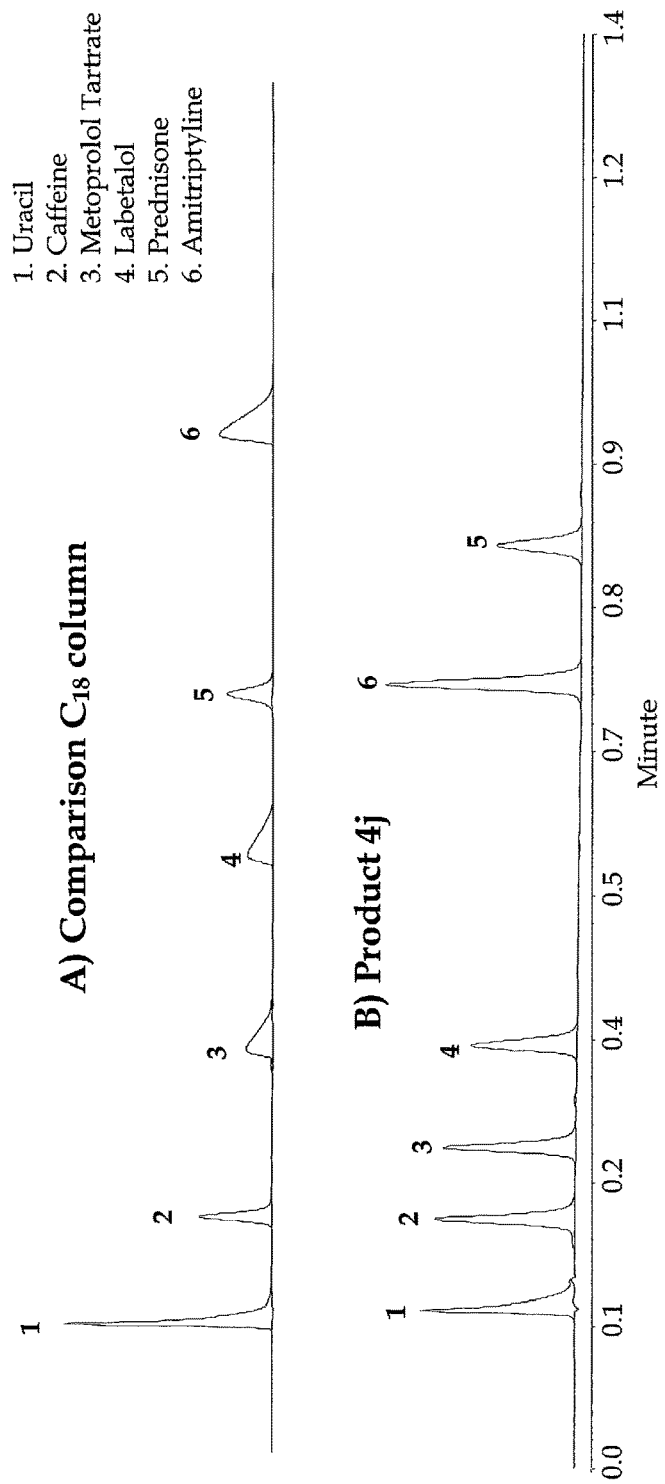
FIG. 2 depicts the peak shape of various analytes using (a) a traditional, commercial C18 bonded material and (b) the material of the instant invention.

As shown in FIG. 2, the results for Product 4j has drastic improvements in peak shape for basic analytes under these conditions, compared to the comparison $C_{18}$ column that did not have any ionizable modifier added. This great improvement can also be demonstrated in improved peak capacities, as detailed in Example 13.

Example 41

Samples of porous particles from Example 2 were evaluated for isocratic loading behavior for amitriptyline. The 4.6×150 mm chromatographic columns were packed using a slurry packing technique. The chromatographic system consisted of an Alliance HPLC® System and a Waters 996 PDA detector. Empower 2 Chromatography Data Software (Build 2154) was used for data collection and analysis; injection volume 20 µL; flow rate: 1.0 mL/min; temperature: 30° C.; detection: 230 nm; analyte: amitriptyline (prepared 60 µg/mL in mobile phase) loading range: 0.3 µg-1.2 µg analyte on column; mobile phase: 0.05% TFA in 40% acetonitrile.

Figure 3:
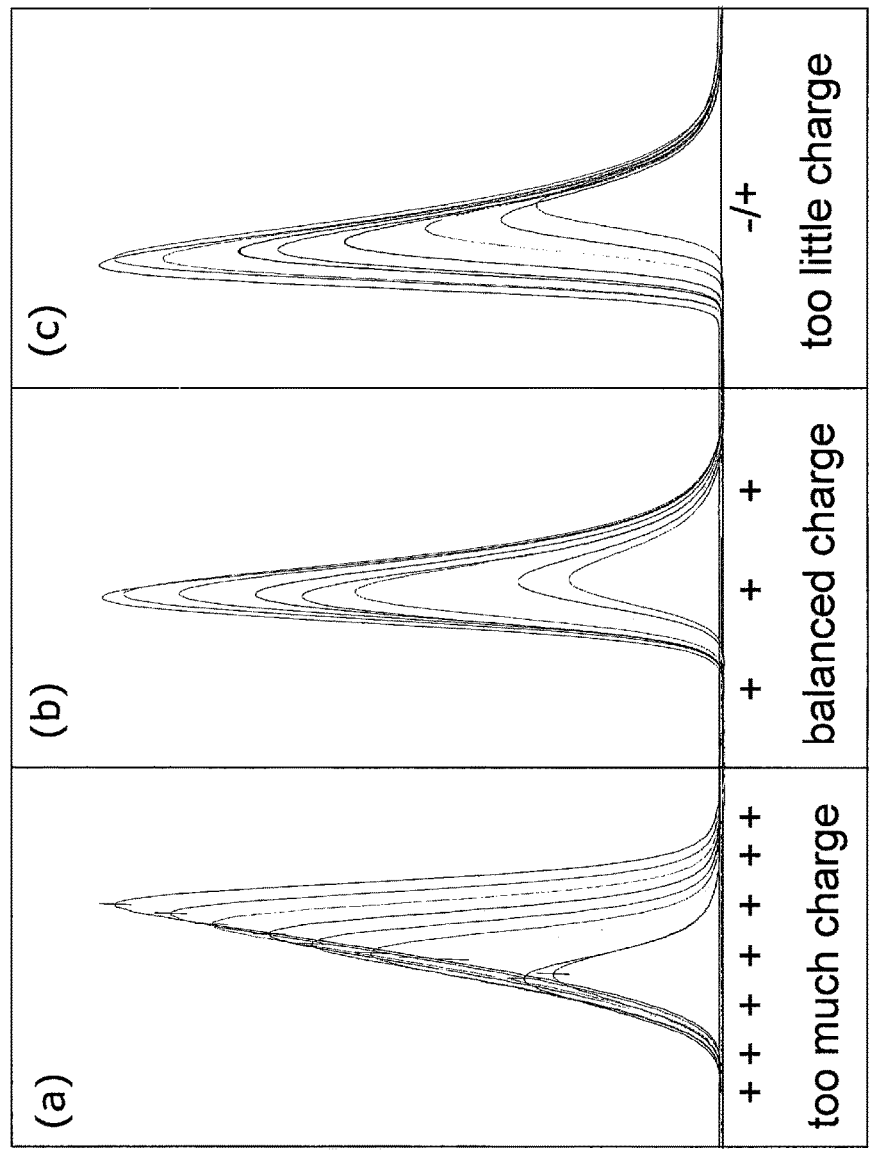
FIG. 3 depicts a comparison of isocratic loading behavior for amitriptyline on 4.6×150 mm columns containing three different HPCM C18 materials: (a) Product 2e which has a high level of ionizable modifier shows fronting/Anti-Langmuirian peak shape suggesting a concave Langmuirian isotherm; (b) Product 2d which has a balanced level of ionizable modifier shows nearly symmetrical Gaussian/linear peak shape suggesting a linear Langmuirian isotherm; and (c) Product 2b which has a very low level of ionizable modifier shows tailing/Bi-Langmuirian peak shape suggesting a convex Langmuirian isotherm.

Deterioration of peak shape of basic analytes with increasing loading concentration is a well known problem for separations performed on HPCM at low pH. The effect of surface charge on peak profiles can be observed, as shown in FIG. 3, by comparing the change in peak profiles with increasing analyte concentration for Products 2b, 2d, and 2e. Product 2e has a high level of ionizable modifier shows fronting/Anti-Langmuirian peak shape suggesting a concave Langmuirian isotherm; (b) Product 2d has an optimal level of ionizable modifier shows nearly symmetrical Gaussian/linear peak shape suggesting a linear Langmuirian isotherm; (c) Product 2b has a very low level of ionizable modifier shows tailing/Bi-Langmuirian peak shape suggesting a convex Langmuirian isotherm. The importance of maintaining good peak shape with increased analyte loading is well known in the art. Product 2d has an optimized surface charge to give high efficiencies for loads that far exceed those attainable on ordinary reversed-phase columns.

Example 42

Figure 4:
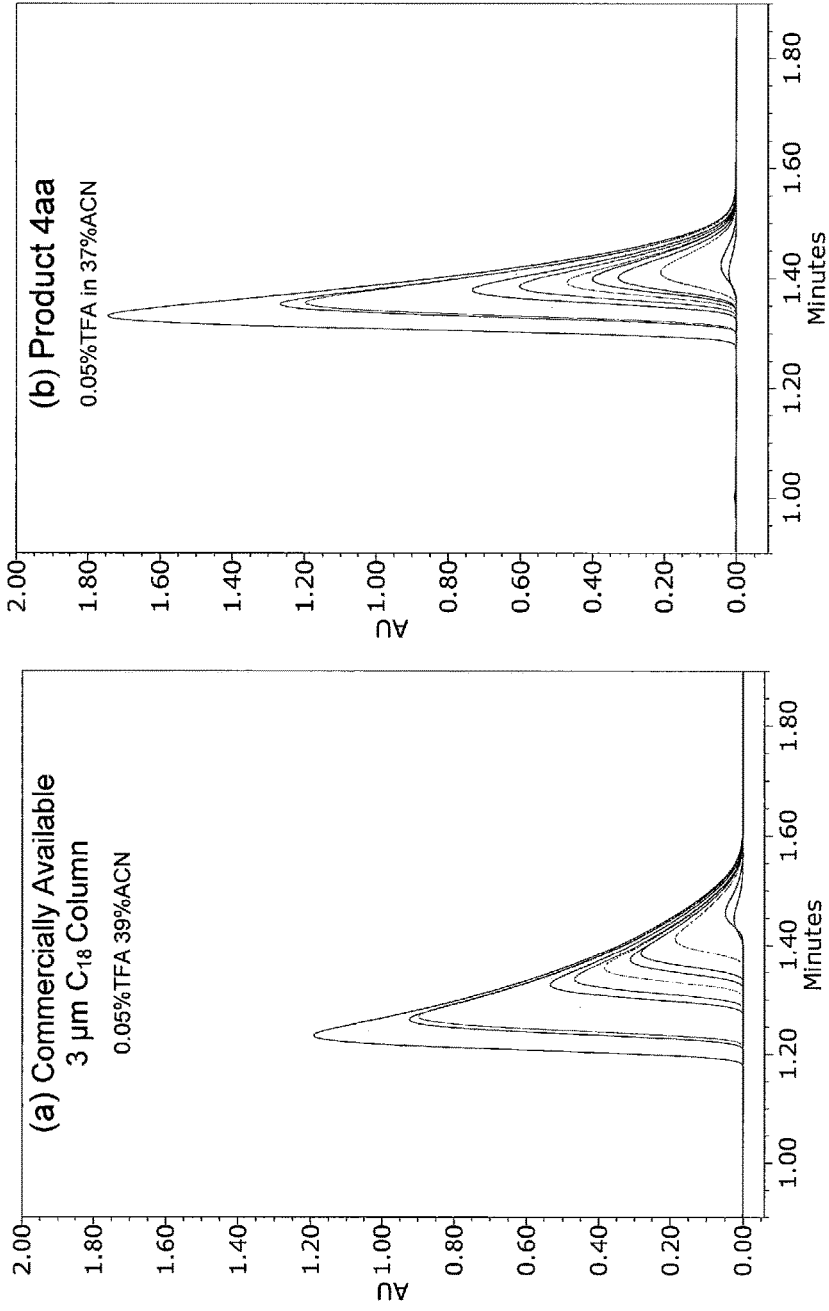
FIG. 4 depicts a comparison of isocratic loading behavior for amitriptyline on C18 columns (both 2.1×50 mm).

Samples of porous particles from Product 4aa and a 3 µm commercially available $C_{18}$ column were evaluated for isocratic loading behavior for amitriptyline. The 2.1×50 mm chromatographic columns were packed using a slurry packing technique. The chromatographic system consisted of an ACQUITY UPLC® System and an ACQUITY UPLC® Tunable UV detector. Empower Chromatography Data Software (Build 1154) was used for data collection and analysis; injection volume 1.5 µL; flow rate: 0.2 mL/min; temperature: 30° C.; detection: 260 nm; analyte: amitriptyline loading range: 0.05 µg-6.0 µg analyte on column; mobile phase: 0.05% TFA in 39% (for Commercially Available 3 µm $C_{18}$ Column) or 37% (Product 4aa) acetonitrile. It is clear, as shown in FIG. 4, that Product 4aa maintains nearly linear-isotherm behavior for amitriptyline at mass loads that approach those used in purification applications.

Example 43

BEH porous hybrid particles (20 g, Waters Corporation, Milford, Mass.; 4.0 µm, 6.78% C; SSA=183 m²/g; SPV=0.70 cm³/g; APD=139 Å) of the formula $(O_{1.5}SiCH_2CH_2SiO_{1.5})(SiO_2)_4$ (prepared following the method described in U.S. Pat. No. 6,686,035) was slurried in water (60 mL) for addition of 3-(trihydroxysilyl)propyl sulfuric acid (6 g, 50% solution). The solution was heated at 90° C. for 20 hours. The reaction was cooled and the product was filtered and washed with water and acetone. The product was then dried at 70° C. under a reduced pressure for 16 hours. The product had 7.29% C and an ion-exchange capacity of 0.160 mequiv/g by titration after subtracting the silanol contribution of a unbonded BEH particle. The surface coverage was determined by the difference in particle % C before and after the surface modification as measured by elemental analysis to be 1.01 µmol/m².

Example 44

Superficially porous silica particles (20 g, 1.3 µm, SSA=90-205 m²/g; SPV=0.1-0.3 cm³/g; APD=80-130 Å) are reacted in a similar manner as detailed in Example 3 to yield a $C_{18}$ bonded material that has an optimal concentration of an ionizable modifier, such as 4PE or APTES. This material (product 43a) is endcapped as detailed in Example 4, and evaluated as detailed in Examples 9-14, 41 and 42. The materials are evaluated as detailed in Examples 9-14, 41 and 42 and are compared to similar materials that do have the addition of the Component A ionizable modifier.

Example 45

The process of Example 44 is performed using Superficially porous silica particles having a particle size of 0.3-2.0 μm. The materials are evaluated as detailed in Examples 9-14, 41 and 42.

Example 46

The process of Example 44 is performed using Superficially porous silica particles having a particle size of 2-3 μm. The materials are evaluated as detailed in Examples 9-14, 41 and 42.

Example 47

The process of Example 44 is performed using Superficially porous silica particles having a particle size greater than 3 μm. The materials are evaluated as detailed in Examples 9-14, 41 and 42.

Example 48

The process of Examples 44-47 are performed using a $C_4$-$C_{12}$, $C_{30}$, embedded polar, chiral, phenylalkyl, or pentafluorophenyl bonding and coatings in place of $C_{18}$ bonding. The materials are evaluated as detailed in Examples 9-14, 41 and 42.

Example 49

The process of Examples 44-48 are performed without the endcapping step prior to characterization. The materials are evaluated as detailed in Examples 9-14, 41 and 42.

Example 50

BEH porous hybrid particles (2.9 μm, Waters Corporation, Milford, Mass.; 6.38% C; SSA=86 m$^2$/g; SPV=0.68 cm$^3$/g; APD=297 Å) of the formula $(O_{1.5}SiCH_2CH_2SiO_{1.5})(SiO_2)_4$ (prepared following the method described in U.S. Pat. No. 6,686,035) were refluxed in toluene (9 mL/g, Fisher Scientific, Fairlawn, N.J.) using a Dean-Stark trap for 2 hours. Upon cooling the Component A silane additive 2-(4-pyridylethyl)triethoxysilane was added and the reaction was heated to reflux for 1 hour. Upon cooling, imidazole (Aldrich, Milwaukee, Wis.) and the Component B silane tert-butyldimethylchlorosilane (TBDMCS, Gelest Inc., Morrisville, Pa.) or octadecyltrichlorosilane (ODTCS, Gelest Inc., Morrisville, Pa.) was added. The reaction was then heated to reflux for 20 hours. The reaction was then cooled and the product was filtered and washed successively with water, toluene, 1:1 v/v acetone/water and acetone (all solvents from J. T. Baker) and then was hydrolyzed as detailed in Example 3, hydrolysis type C. The product was filtered and washed successively with toluene, 1:1 v/v/acetone/water, and acetone. The product was dried at 70° C. under reduced pressure for 16 hours. Reaction data are listed in Table 20. The surface coverage of these products was determined by the difference in particle % C before and after the surface modification as measured by elemental analysis. Product 50b was further endcapped as detailed in Example 4 to yield a final carbon content of 10.52% C.

TABLE 20

| | | | Component B | | | |
|---|---|---|---|---|---|---|
| Product | Particles (g) | Component A Silane Additive (g) | Primary Silane | Primary Silane (g) | Base (g) | % C | Surface Coverage (μmol/m$^2$) |
| 50a | 20 | 0.139 | TBDMCS | 2.6 | 1.4 | 7.74 | 2.50 |
| 50b | 15 | 0.104 | ODTCS | 0.9 | 0.3 | 9.50 | 1.95 |

Example 51

Superficially porous silica particles (1.35 um, SSA=55 m$^2$/g; SPV=0.15 cm$^3$/g; APD=107 Å, 1.2 μm non-porous core, 0.1 μm thick porous shell) were refluxed in toluene (9 mL/g, Fisher Scientific, Fairlawn, N.J.) using a Dean-Stark trap for 2 hours. Upon cooling a Component A ionizable modifier 2-(4-pyridylethyl)triethoxysilane (4PE, Gelest Inc., Morrisville, Pa.) was added for product 51a and reaction was heated to reflux for 1 hour before cooling. No Component A ionizable modifier was added for product 51b. Imidazole (Aldrich, Milwaukee, Wis.) and octadecyltrichlorosilane (ODTCS, Gelest Inc., Morrisville, Pa.) were added. The reaction was then heated to reflux for 20 hours. The reaction was then cooled and the product was filtered and washed successively with water, toluene, 1:1 v/v acetone/water and acetone (all solvents from J. T. Baker) and then was hydrolyzed as detailed in Example 3, hydrolysis type C. The product was filtered and washed successively with toluene, 1:1 v/v/acetone/water, and acetone. The product was dried at 70° C. under reduced pressure for 16 hours. Reaction data are listed in Table 21. The surface coverage of these products was determined by the difference in particle % C before and after the surface modification as measured by elemental analysis. These products were further endcapped as detailed in Example 4.

TABLE 21

| Product | Particles (g) | 4PE (g) | ODTCS (g) | Base (g) | % C | Surface Coverage (μmol/m$^2$) | Final % C |
|---|---|---|---|---|---|---|---|
| 51a | 15 | 0.067 | 0.74 | 0.26 | 2.84 | 2.42 | 3.37 |
| 51b | 15 | — | 0.74 | 0.26 | 3.31 | 2.86 | 3.73 |

Example 52

Following the protocol detailed in Example 13, peak capacity comparisons were made for Products 51a and 51b, as detailed in Table 22. The determination of peak capacity and the problems caused by poor peak shape and resulting poor peak capacities for basic analytes in low pH gradient separations is well known in the field of HPLC and UPLC. Increased peak capacity ratios correlate with improved performance for basic analytes under these test conditions. Products 51a and 51b have the same feed material and were both similarly bonded, the only difference between these materials is the inclusion of the Component A ionizable modifier for product 51a. Improvements in peak capacity ratios were obtained for Product 51a over 51b, which is due to the introduction of the Component A ionizable modifier.

TABLE 22

| Product | A<br>Amitriptyline<br>Pc | B<br>Prednisone<br>Pc | Ratio<br>A/B |
|---|---|---|---|
| 51a | 126 | 204 | 0.62 |
| 51b | 45 | 184 | 0.24 |

Example 53

Porous silica particles are hybrid coated, $C_{18}$-bonded and are endcapped in a process similar to the one detailed in U.S. Pat. No. 7,563,367B to yield product 53a. Alternatively, an ionizable modifier reagent, Component A (as detailed in Example 15) is added at different points in this process. Product 53b introduced the Component A additive before hybrid coating. Product 53c introduces the Component A additive before $C_{18}$-bonding. Product 53d introduces the Component A additive before endcapping. Product 53e introduces the Component A additive after endcapping. The materials are evaluated as detailed in Examples 9-14, 41 and 42.

Example 54

Superficially porous silica particles are hybrid coated, $C_{18}$-bonded and are endcapped in a process similar to the one detailed in U.S. Pat. No. 7,563,367B to yield product 54a. Alternatively, an ionizable modifier, Component A (as detailed in Example 15) is added at different points in this process. Product 54b introduced the Component A additive before hybrid coating. Product 54c introduces the Component A additive before $C_{18}$-bonding. Product 54d introduces the Component A additive before endcapping. Product 54e introduces the Component A additive after endcapping. The materials are evaluated as detailed in Examples 9-14, 41 and 42.

Example 55

BEH porous hybrid particles (4.0 μm, 25 g, Waters Corporation, Milford, Mass.; 6.78% C; SSA=183 m$^2$/g; SPV=0.70 cm$^3$/g; APD=139 Å) of the formula $(O_{1.5}SiCH_2CH_2SiO_{1.5})(SiO_2)_4$ (prepared following the method described in U.S. Pat. No. 6,686,035) were refluxed in toluene (375 mL, Fisher Scientific, Fairlawn, N.J.) using a Dean-Stark trap. Upon cooling the zirconium n-propoxide (70% in n-propanol, 4.28 g, Gelest Inc., Morrisville, Pa.) was added and the reaction was stirred at ambient temperature for an hour and then heated to reflux overnight. The reaction was then cooled and the product was filtered and washed successively with toluene and 1% formic acid, and then was hydrolyzed in 1% formic acid for 1.5 hours at ambient temperature. Product 55a was filtered and washed with copious amounts of water and acetone. The product was dried at 80° C. under reduced pressure for 16 hours.

Example 56

Product 55a is further modified as detailed in Examples 1-8 and 15. The materials are evaluated as detailed in Examples 9-14, 41 and 42.

Example 57

The process of Examples 1, 3, 5, 7, 8, 15, 19, 21, 24, 27-29, 31-33, 35, 43-51, 53-55 are performed by using one or more ionizable modifiers selected from the group (not limited to) alkoxides, halides, salts and complexes of zirconium, aluminum, cerium, iron, titanium, and other ionizable or amphoteric groups. These products are endcapped as detailed in Example 4. The materials are evaluated as detailed in Examples 9-14, 41 and 42.

Example 58

A chromatographic column containing a packed bed of 1-5 μm chromatographic material that is $C_{18}$-bonded is evaluated as detailed in Examples 9-14, 41 and 42. This column is then flushed through with a dilute solution of a Component A, ionizable modifier in a suitable solvent for an extended time period to allow for incorporation of the ionizable modifier on the chromatographic bed. Examples of ionizable modifiers are included in Example 15 and 57. The column is further washed with a suitable solvent and is evaluated as detailed in Examples 9-14, 41 and 42.

Example 59

$C_{18}$-bonded and endcapped 1-5 μm chromatographic materials are modified with a Component A, ionizable modifier. Examples of chromatographic materials are included in Example 15. Examples of ionizable modifiers are included in Example 15 and 57. The materials are evaluated as detailed in Examples 9-14, 41 and 42 and are compared to the $C_{18}$-bonded and endcapped material that does not contain an ionizable modifier.

Example 60

The process of Example 58 and 59 are performed on superficially porous materials. Evaluations are performed as detailed in Examples 9-14, 41 and 42.

Example 61

The process of Example 58-60 are preformed on chromatographic materials that are $C_4$-$C_{12}$, $C_{30}$, embedded polar, chiral, phenylalkyl, or pentafluorophenyl bonding and coatings in place of $C_{18}$ bonding. Evaluations are performed as detailed in Examples 9-14, 41 and 42.

Materials and Methods for Examples 62, 63, 64, and 65

The test mixes used in these examples are available from Waters Corporation, Milford Mass. The tryptic digest of cytochrome c is available from Waters Corporation, Milford Mass. as P/N 186006371. Digest sample used 3.8 μg per injection in all of the evaluations. The other test mix used is available from Waters Corporation, Milford Mass. as the MassPREP Peptide Standard P/N 186002337 and contains the following peptides/small protein listed in elution order in a TFA gradient: V0 (allantoin), [1] RASG-1, [2] angiotensin Fragment 1-7, [3] bradykinin, [4] angiotensin II, [5] angiotensin I, [6] renin substrate, [7] enolase T35, [8] enolase T37, and [9] melittin. The standard was diluted to contain each peptide at a concentration of 15 ng/μL, for 1× samples or 30 ng/μL for 2× samples. The amount of each peptide per injection was varied by varying injection volume of the 1× or 2× sample. This standard test mix was selected because it includes a diverse set of peptides and includes tryptic digest peptides (enolase T35 and enolase T37), peptides/small protein from MW (g/mol) of 897.47 for angiotensin fragment 1-7 to 2,845.74 for melittin, the small protein that is the principal toxic component of bee venom, and pI's from 3.97 (enolase T37) to 12.06 (melittin). The mix was selected to emulate a broad range of peptide applications, such as several peptides that are targets of regulation for ACE inhibitors, and encompass peptides that elute over the gradient span.

The columns used in these comparisons are 1.7 μm particle packed 2.1×50 mm stainless steel columns containing ACQUITY UPLC® CSH C18 130 Å (CSH130 C18) which comprises the materials of the invention, available from Waters Corporation, Milford Mass.; ACQUITY UPLC® PST C18 130 Å (BEH130 C18) available from Waters Corporation, Milford Mass.; ACQUITY UPLC® PST C18 300 Å (BEH300 C18) available from Waters Corporation, Milford Mass.; ACQUITY UPLC® BEH C8 (BEH130 C8) available from Waters Corporation, Milford Mass.; Phenomenex 1.7 μm core-shell KINETIX C18, available from Phenomenex, Torrance, Calif.; and AERIS PEPTIDE XB C18, available from Phenomenex, Torrance, Calif. This list includes the column of the technology of this invention, the ACQUITY UPLC® CSH C18 130 Å. The CSH130 C18 packing is bonded on the BEH particle used in the BEH130 C18 packing, the difference being the CSH packing makes use of the charged surface hybrid technology as described herein.

Example 62

Benefits in Sensitivity of Using Formic Acid Over TFA as a Mobile Phase Additive for MS Analyses For isocratic methods a measure of performance for a column is the number of plates or efficiency. However, peptides are almost never eluted using isocratic conditions due to the extremely broad peaks these conditions usually generate. This is why gradient conditions are the most frequently used for peptides. For gradient methods, performance is measured in terms of peak capacity. One of the simplest formulas for peak capacity (Pc) is shown below:

$$P_c = 1 + \frac{t_G}{w_{ave}}$$

Where $t_G$ is the gradient time in minutes and $w_{ave}$ is the average of all the peptide peak widths taken 13.4% of the peak height.

Figure 5:
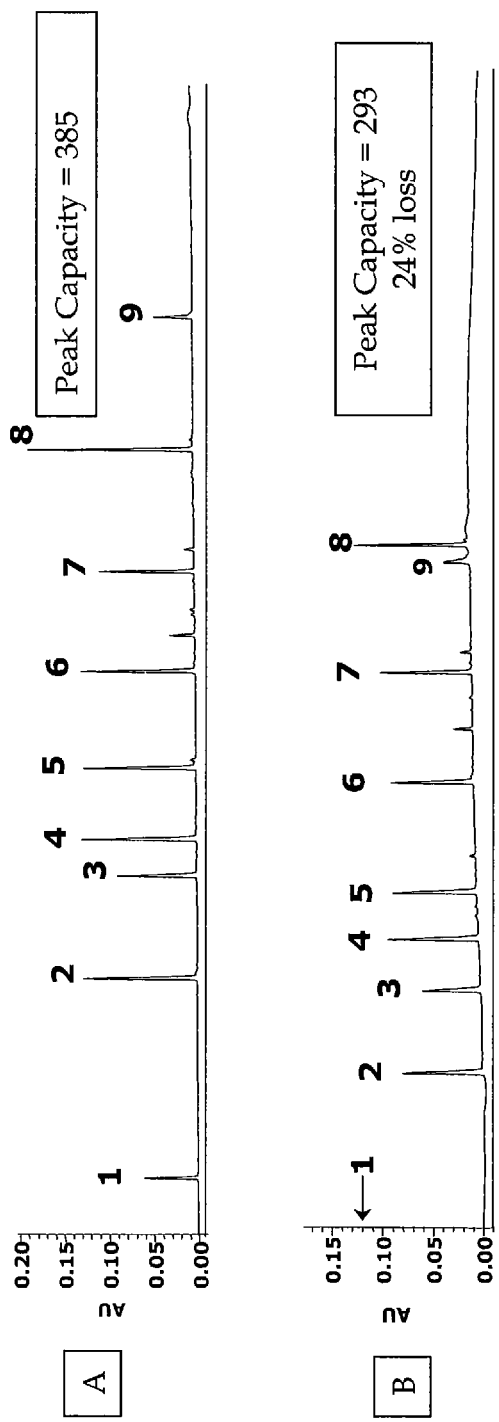
FIG. 5 depicts the peak loading of a 1.7 μm BEH130 C18 2.1×50 mm column.
Figure 6:
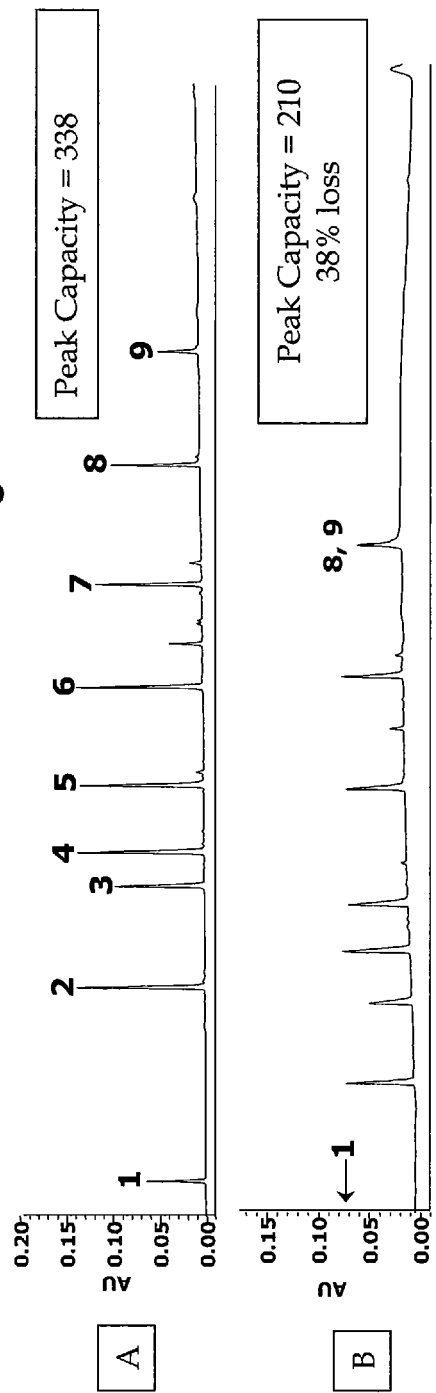
FIG. 6 depicts the peak loading of a 1.7 μm Kinetex C18 2.1×50 mm column.

The loss of sensitivity due to the use of TFA during the analysis of peptides by MS is often underappreciated due to the lack of side by side comparisons. In the past, the problem with making direct comparisons was that the peak shape for peptides in formic acid mobile phases on older C18 phases was so poor that comparisons were difficult. On state of the art C18 phases comparisons can be made at low on-column mass loads (37.5 ng for each peptide). Peak capacities are compared in FIGS. 5 and 6 on state of the art C18 columns under low mass load conditions using a ACQUITY Tunable UV Detector set to 214 nm. In FIGS. 5 and 6, the chromatographic conditions are as follows: Chromatographic conditions: 0-70% linear gradient of B in 30 minutes using a linear gradient at 0.2 mL/min where mobile phase A is 0.1% FA or 0.05% TFA in 100% Milli-Q water and mobile phase B is 0.075% FA or 0.05% TFA in 71.4% ACN; Column temp: 80° C. Peak ID: [1] RASG-1, [2] angiotensin fragment 1-7, [3] bradykinin, [4] angiotensin II, [5] angiotensin I, [6] renin substrate, [7] enolase T35, [8] enolase T37, [9] melittin. The sample load was 37.5 ng for each peptide on each column. Even under these low mass loads the BEH130 C18 and the core-shell Kinetex C18 lose 24% and 38% of their Pc's, respectively, when going from TFA to formic acid as a mobile phase modifier.

Figure 7:
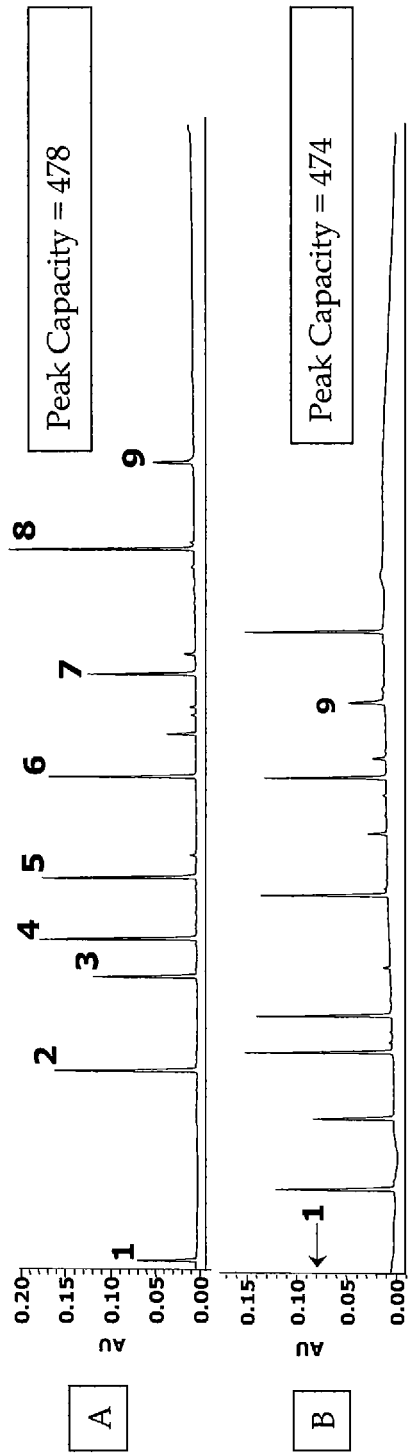
FIG. 7 depicts the peak loading of a 1.7 μm CSH130 C18 2.1×50 mm column of the invention.

FIG. 7 shows the same TFA versus formic acid gradient comparison on a CSH130 C18 column, which shows at this mass load, essentially no loss of peak capacity in addition to having 24% higher Pc than the highest peak capacity column (BEH130 C18) in the TFA gradients and 62% higher Pc than the highest of the other two columns (BEH130 C18) in the formic acid gradients. This example highlights the superior performance achieved with the column of this technology and the clear ability to perform side by side comparisons of TFA and formic acid performance on the MS.

Figure 8:
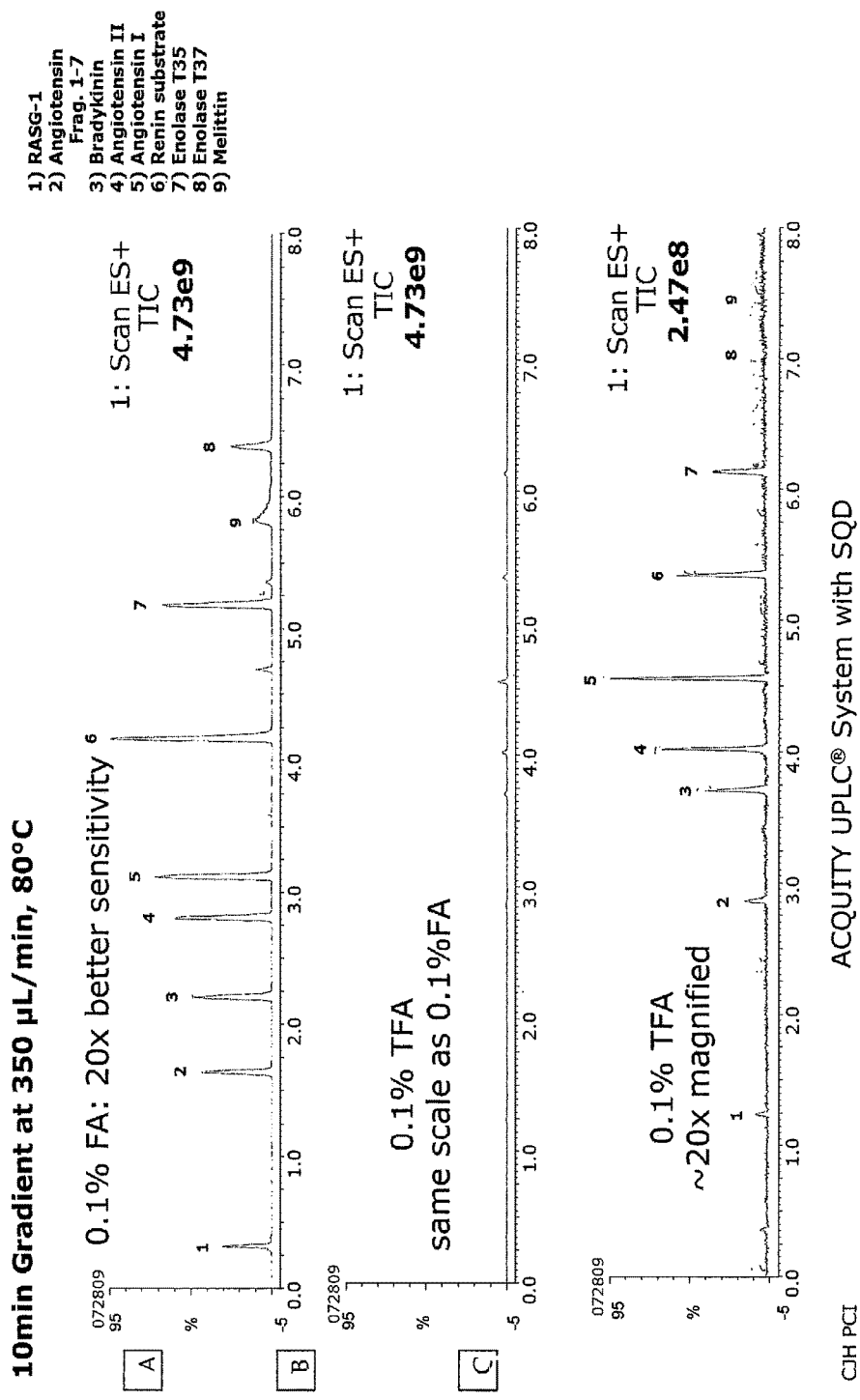
FIG. 8 depicts a peptide separation using a 10 min Gradient running from 1.8% to 50% ACN with 0.1% FA or 0.1% TFA, with a column of the invention. A shows the Total Ion Current for the column running the same 10 min gradient using formic acid; B shows the Total Ion Current using TFA as the mobile phase modifier; C shows the loss of sensitivity by the clear increase in the background noise.

FIG. 8 shows a peptide separation using a 10 min Gradient gradient at 350 μL/min running from 1.8% to 50% ACN with 0.1% FA or 0.1% TFA, with on a 2.1×50 mm column of prototype 4p (Table 4) of this technology maintained at 80° C. The Waters SQD capillary voltage was 3.3 kV, cone voltage was 30V, extractor was 3V, and RF lens was 0.1V. The source and desolvation temperatures were 150, and 350° C., respectively. Gas flow rates for the desolvation gas and cone gas were 800 L/hr and 50 L/hr, respectively. The analyzer LM and HM resolutions were set to 15. Ion energy was set to 0.5 and gain to 1. Full scans were collected for m/z 400-1500 using a scan rate of 0.2 sec in continuum mode. The sample was the MassPREP Peptide Standard Test Mix.

In FIG. 8 the Total Ion Current (TIC) chromatogram from the MS shows the sensitivity loss when changing from 0.1% formic acid (FA) to 0.1% TFA as a mobile phase modifier in a peptide gradient on a column of prototype 4p. As shown in FIG. 7 the CSH130 C18 column of this technology did not show a loss of sensitivity due to changes in peak height as the other C18 phases did. The loss in sensitivity in the MS with TFA is due to suppression of the ionization efficiency of the peptides by the presences of TFA in the source. The TFA chromatogram in FIG. C is shown at 20× magnified scale to demonstrate that the peptide peaks are indeed present. FIG. 8A shows the TIC chromatogram for column 4p of this technology running the same 10 min gradient using formic acid and in FIG. 8B using TFA as the mobile phase modifier. Chromatograms in FIGS. 8A and 8B are shown on the same TIC scale (4.73e9) to illustrate the degree of signal suppression experienced with the use of TFA. The fact that peptide peaks are actually present in FIG. 8B is confirmed by its ~20×TIC magnification in the TIC scale (2.47e8) of FIG. 8C. FIG. 8C clearly shows the loss of sensitivity by the clear increase in the background noise relative to the peak height.

Experimental Methods for Examples 63, 64, and 65

In the Examples 63, 64, and 65, the following gradient conditions were used unless otherwise specified 99.1% mobile phase A to 66.7% mobile phase B in 30 min, unless otherwise indicated a 2 min hold in 66.7% B with a 4 mL re-equilibration in A. Mobile phase A was 0.1% formic acid (FA) in H2O (v/v) and mobile phase B was 0.085% formic acid in 75% acetonitrile (ACN) (v/v). The column temperature was maintained at 60° C. unless otherwise specified. The flow rate was ~0.2 mL/minute—minor adjustments were made to keep the same gradient slope on all columns for the case when porosity was significantly different. All evaluations were run on ACQUITY UPLC®, available from Waters Corporation, Milford, Mass., with 380 μL mixer, Stainless Steel sample Needle, 10 μL injection loop, Injection Type: Partial Loop; Injection volume was 5 μL unless otherwise specified, ACQUITY® Tunable Ultraviolet-Visible (TUV) Detector, detection wavelength: 220 nm unless otherwise specified, flow cell: 250 nL, sampling rate at 20 Hz, no filter. Data acquisition was with Empower 3 Software, build 2154 [Base Package], Feature Release 5 or 4, ICOP V1.30, System Suitability.

Example 63

Improvement in Peak Shape Under Overload Conditions to Observe Low Sensitivity Peptides The following example uses a well characterized tryptic digest sample of cytochrome c to illustrate the scenario of tradeoffs that can occur between UV and MS analysis of low sensitivity or low abundant peptides. The MS was showing low sensitivity for the early eluting peptides in the tryptic digest sample of cytochrome c in particular the T13-T14 peptide. The peak shape of a deliberately overloaded sample on a BEH130 C18 column, available from Waters Corporation, Milford, Mass., is compared to that of the technology of this invention, CSH130 C18, available from Waters Corporation, Milford, Mass., using the 0.1% formic acid gradient described below.

Gradient conditions for the tryptic digest of cytochrome c are as follows. The gradient ran from 1% B to 21% B in 5 min to 31.4% B at 7.5 min then 95% B at 11 min and remained there until 12.5 min; at 12.5 min it returned to 1% B to re-equilibrate until the next injection. Mobile phase A was 0.1% FA in water and mobile phase b was 0.085% FA in 70% acetonitrile. The run time was 15 min the injection volume was 5 μL. The detection wavelength was 214 nm. The column was maintained at 40° C. The mixer was a 50 μL mixer or a peptide 380 μL mixer. The column configuration was 2.1×50 mm stainless steel hardware. An ACQUITY TUV detector was used to obtain the UV trace at 214 nm. The detector was in series just before the MS. The MS was a Waters SQD running under Empower 3 Software, build 2154 [Base Package], Feature Release 5 or 4, ICOP V1.30, System Suitability.

Figure 9:
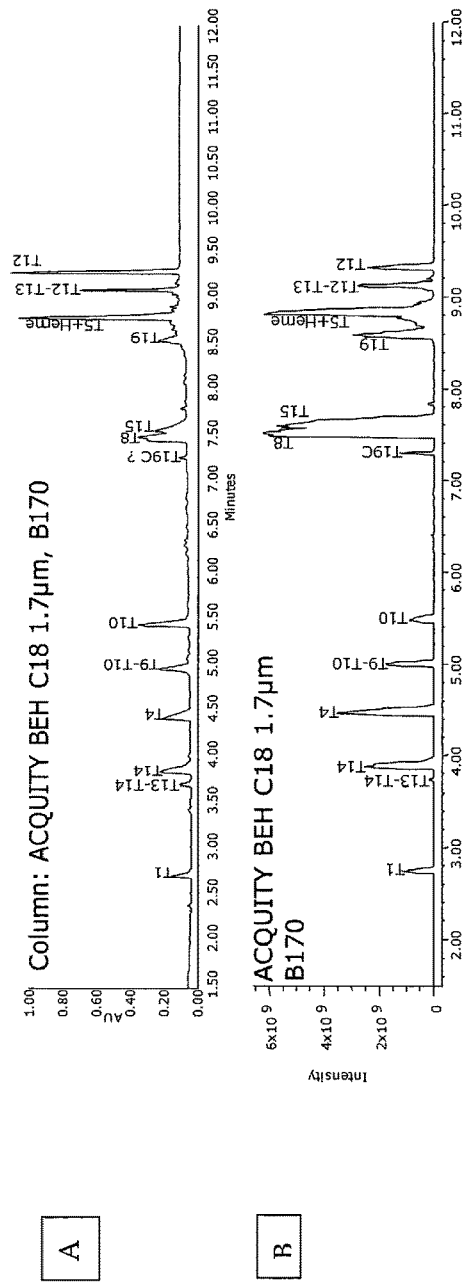
FIG. 9 depicts the UV trace (A) taken at 214 nm and MS trace (B) for the BEH130 C18 showing the overloaded peaks in a 0.1% FA mobile phase gradient for most cytochrome c peptides in order to get the T13-T14 peptide peak identification confirmed by MS. In the MS trace T13-T14 peptide peak was identified as having an m/z 807 with one missed cleavage.
Figure 10:
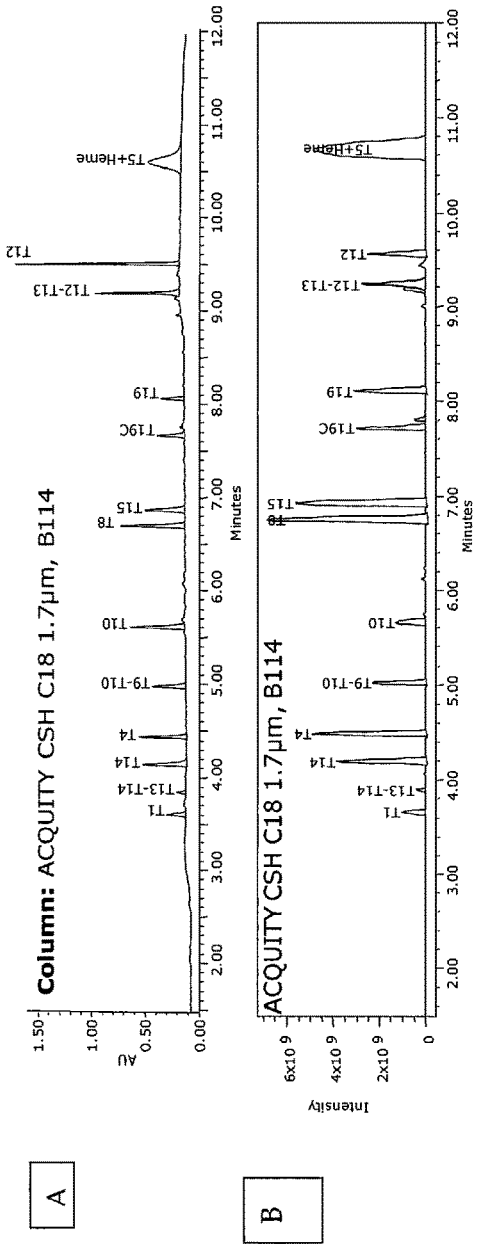
FIG. 10 depicts the UV trace (A) taken at 214 nm and MS trace (B) for the CSH130 C18 showing the same mass load and using the same chromatographic conditions as in FIG. 9 for cytochrome c peptides in order to get the T13-T14 peptide peak identification confirmed by MS. Significantly improved peak shape on CSH130 C18 allows for even higher mass loading for the possible confirmation of even less abundant peptides than T13-T14.

The same amount (3.8 μg per injection) of the tryptic digest of cytochrome c was injected on the BEH130 C18 shown in FIG. 9 and the CSH130 C18 shown in FIG. 10. The UV traces (top) for the BEH130 show right angle triangular peaks for many of the peptides. This peak shape is a clear indication of classic Langmuirian-like overloaded peaks. In contrast the CSH130 column shown in FIG. 10 shows symmetrical narrow peaks for the same peptides at the same load. Had the T13-T14 peak been closer to the T14 peak or the sample load been higher the resolution on the BEH column would have been lost and the T13-T14 peak would not have been identified. In comparison, the appearance of the traces in the FIG. 6 10 for the CSH130 C18 column would be readily recognized by those skilled in the art of peptide mapping as the better choice for a more comprehensive and complete list of peptides from the sample.

The last peptide in the chromatogram in FIG. 10 is very broad because it contains a heme group, which is a porphyrin ring at the center of which is an iron ion. Although the peak is board it does not appear to be overloaded but the CSH130 C18 does appear to show unusual affinity for the iron containing peptide and perhaps other metal containing peptides.

It is clear from the above figures that the T13-T14 peptide has the lowest sensitivity of the peptides and could easily be missed, and actually was, at more normal column loads on a Waters TQS. However, on the CSH130 column neither sensitivity, the ability to identify peptides by MS, nor peptide peak shape, which allows for accurate quantifications, needs to be sacrificed, which allows for accurate quantifications.

Example 64

Improved Peak Shape Compared to Core-Shell Packing in Formic Acid Mobile Phases

Figure 11:
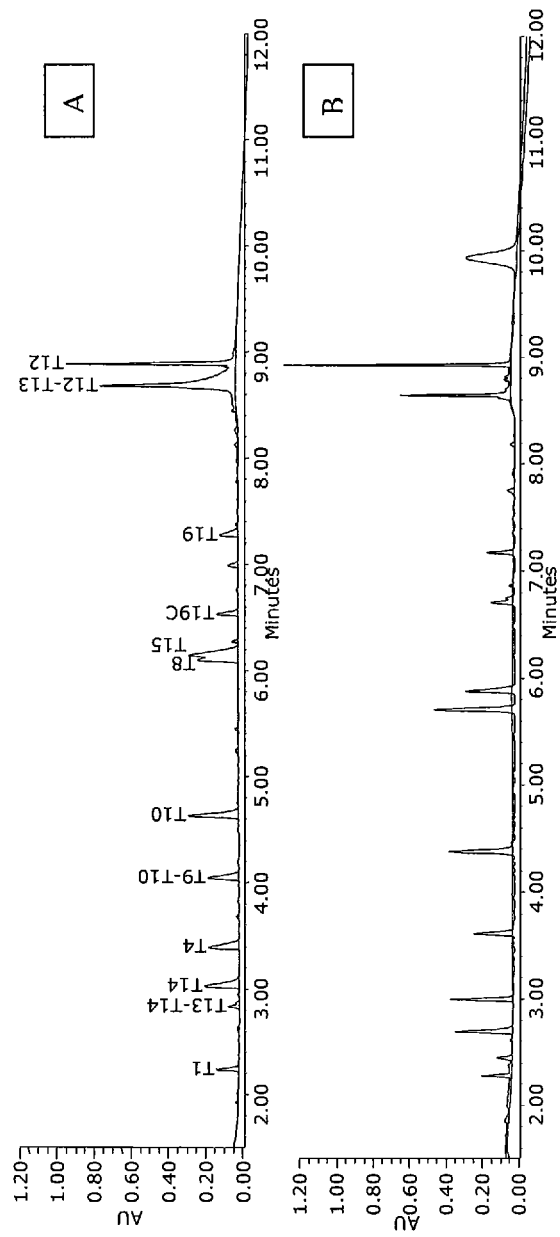
FIG. 11 depicts chromatograms of 3.8 µg per injection comparison of a tryptic digest of cytochrome c on A. Aeris PEPTIDE XB-C18 and B. CSH130 C18 columns.

Although core-shell columns may not be best choice for peptide separation, the Aeris PEPTIDE XB-C18 was designed for this application. FIG. 11 depicts UV chromatograms of 3.8 μg per injections comparison of a tryptic digest of cytochrome c on Aeris PEPTIDE XB-C18 1.7 μm (top-A) and CSH130 C18 1.7 μm (bottom-B) using the same gradient and conditions used in example 63. FIG. 11 shows that even when compared to columns specifically designed for peptide separations the CSH C18 provides superior peak shape.

In this case, the peak capacity on the two columns can only be compared for the first 6 peptides because of co-elution of peptides in the various other gradient segments. The first gradient segment is 5 minutes long and provides a sufficient number of peaks to average and assess performance. For the first 6 peptides, the peak capacity on the Aeris PEPTIDE XB-C18 column is Pc=76 and on the CSH130 C18 column is Pc=108, which is 43% higher than that on the Aeris column.

Example 65

Peptide Mass Loading Comparison

It is known in the art of preparative chromatography that the mass loading of a column is limited in part by the buffer capacity of the mobile phase. One aspect of this limitation that affects ionized compounds is the ionic strength of the mobile phase. It has been shown that low ionic strength mobile phases such as those containing 0.1% formic acid readily produce overloading for basic compounds unlike mobile phases containing 0.1% TFA.

Without being limited by theory, there is still debate as to the cause of the overloading at low pH for ionized species. One proposed cause is that there are a few highly active sites on the particle surface that overload quickly. These sites create the tail of the peak and once filled weaker sites take over retention. Another possible explanation is that once a few ionized bases (cations) adsorb on the surfaces of the narrowest pore regions they block further access to the rest of the pore surface by mutual repulsion of the other approaching cationic bases approaching in solution the cationic base on attempting to reach the surface from the mobile phase. TFA has been used in the past to mitigate both these possible scenarios. TFA at a 0.1% (v/v) concentration is nearly completely dissociated (98%), as a solution in water provides a pH of 1.9, and forms neutral ion pairs with cationic ions. In contrast, formic acid at 0.1% v/v is only about 8% dissociated, as a solution in water provides a pH of about 2.7, and is not a strong ion pair. For these reasons peptide peak shape generally suffers from overload of high energy sites believed to be strongly acidic silanols. TFA appears to be more effective in blocking these interactions by neutralizing cationic sites on peptides, of which most and all tryptic peptides contain and if highly acidic silanols were the cause the TFA reduces the pH of the mobile phase thereby reducing the number of deprotonated silanols.

In the table 2, 3 below, are peak capacities for BEH130 C8, BEH130 C18, and CSH130 C18 using various mass loads of the MassPREP Peptide Standard. The Columns were evaluated using a 30 minute gradient running from 0.1% formic acid in 0.7% acetonitrile to 0.085% formic acid in 50% acetonitrile. The column temperature was maintained at 60° C. and injection volumes of 3-7 µL were used with the 1× and 2× concentration of the standard.

Figure 12:
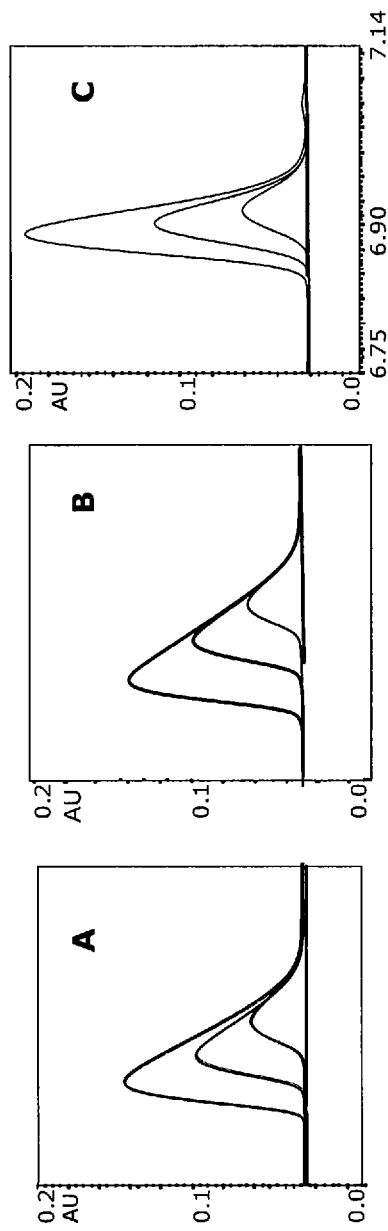
FIG. 12 depicts overlays of bradykinin at 45, 105, and 210 ng on the A. BEH130 C8, B. BEH130 C18, and C. CSH130 C18 columns.

The average Pc's of 8 peptides are reported in Table 23. The first eluting peptide in the standard mix was not included in the calculation because of a baseline disturbance interfering with its integration. As can be seen in Table 23 the BEH130 C18 and the BEH130 C18 lost over 30% of their peak capacity when the on-column mass load was increased from 45 ng per peptide to 210 ng per peptide. For this same increase in mass load the CSH130 C18 column lost only 11% and started at 45 ng load with 25% and 32% higher peak capacity than the BEH130 C8 and BEH130 C18, respectively. Examples of the overloaded peak shape for bradykinin at the 45, 105, and 210 ng mass loads are shown in FIG. 12. for the (A) BEH130 C8, (B) BEH130 C18, and (C) CSH130 C18 columns.

TABLE 23

Average peak capacities for 45-210 ng per peptide in the MassPREP Peptide Standard.

| Peptide Load | $P_c$ for MassPREP Peptide Standard | | |
|---|---|---|---|
| ng each | BEH130 C8 | BEH130 C18 | CSH130 C18 |
| 45 | 326 | 308 | 406 |
| 75 | 292 | 292 | 399 |
| 105 | 266 | 248 | 390 |
| 150 | 243 | 222 | — |
| 210 | 218 | 197 | 362 |
| % loss 45-210 ng | 33 | 36 | 11 |

Example 66

Experiment 62-65 are repeated using particles one ore materials that are included, but not limited to core-shell, monoliths, RAMS, membranes, frits, or fully porous metal oxides, organic-metal oxide composites, or organic spherical, irregular, various selected shapes such as but not limited to donuts, rods, or ovals, or materials from Examples 1-8, 15-38, 43-51, or 53-61. These materials contain surface charges with the goal to improve peak shape, selectively advance adsorption of some analytes over others or to prevent any unwanted interaction with the surface. The charged surface material modifier can be used on any material having pore sizes of 34 Å to 2000 Å, micropores (<34 Å), or it can be non-porous materials or combination thereof. For macro molecules of MW>1000 non-specific binding to surfaces has been a commonly reported problem in-particular with chromatographic packings and other chromatographic system component materials. This problem is commonly identified by the loss of analyte particularly at low concentrations. This loss occurs to surfaces and the charged group can be, without being limited by theory, designed for particular applications to prevent the macro molecule from reaching and interacting with undesirable the surfaces or materials required by design constraints. All macro molecules have within their structure charged groups that can be used for this purpose become problematic in this regard. The pka and or ionization state of the basic surface charged groups can be adjusted according to the strength and proximity of electron withdrawing groups to lower the pKa or electron donating groups to increase the pka. The opposite is true charge acidic groups for prevent contact with the surface for anions. These charged groups may also contain other functional groups to in addition to controlling the pKa can also assist in the ultimate goal of the desired application.

Example 67

Analysis of Large Peptides and Small Proteins

Figure 13:
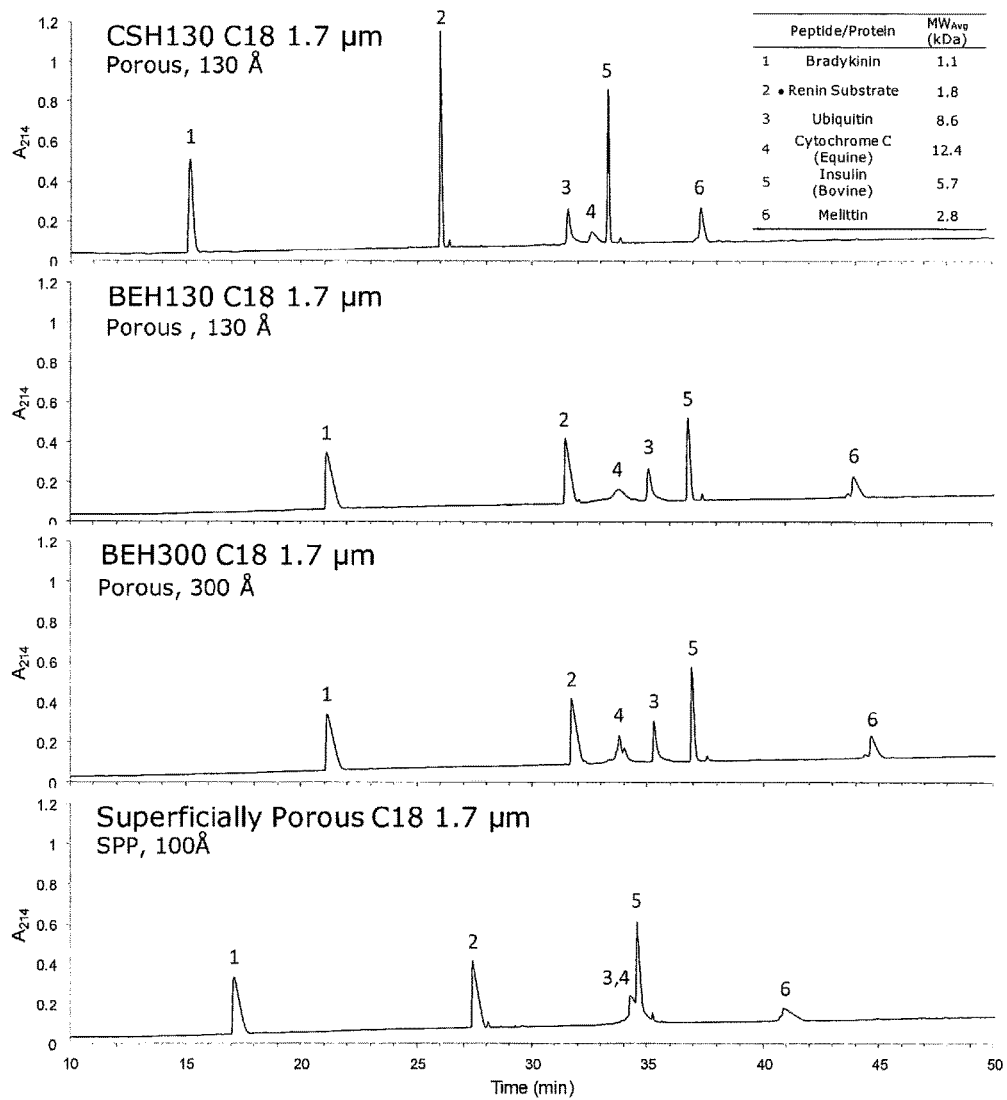
FIG. 13 depicts chromatograms of large peptides/small proteins obtained with 0.1% FA mobiles phases from four different columns.

It was of interest to evaluate the use of CSH130 C18, even with its 130 Å pores, for separations of a mixture of larger peptides and small proteins. Each component of in the mix was injected at a 1 µg on-column mass load. Six polypeptides ranging in mass from 1 to 12 kDa were separated on four columns containing stationary phases with pores varying from 100-300 Å in diameter (FIG. 13). Columns: 2.1×150 mm. Conditions: gradient from 2% to 50% ACN with 0.1% FA in 60 minutes; flow rate 300 µL/min; column temperature 40° C.; scan range m/z 50-1990. Peaks were identified by ESI-MS.

Through comparison of these chromatograms, it is clear that the CSH130 C18 column produced the best peak shapes and highest sensitivity for most of the peptide species, including insulin (5.8 kDa).

Analysis of the largest polypeptides, ubiquitin (8.6 kDa) and cytochrome c (12.4 kDa), better defined the effect of using 300 Å versus 130 Å pore size sorbents. Ubiquitin was found to exhibit only slightly better peak shape on the BEH300 C18 (300 Å) column versus both the CSH130 C18 (130 Å) and BEH130 C18 (130 Å) columns. In contrast, the largest polypeptide, cytochrome c, was separated with markedly better peak shape using BEH300 C18. The BEH300 C18 column was actually capable of resolving cytochrome c into multiple peaks, indicating protein heterogeneity. Most peptide separations, such as those derived from proteolytic digests, will contain few, if any, species this large. For this reason, the use of a 130 Å pore size particle, like CSH130 C18, might more positively impact the separation of a protein digest than the use of a larger pore size particle, since it will offer more surface area and likely greater retention of small, hydrophilic peptides. A larger pore size particle, like 300 Å pore size C18, might instead be preferred when near exclusively analyzing large peptides, for example those weighing more than 6 kDa. Such an analysis might involve the study of disulfide-linked peptides from a Lys-C digest of an IgG when it may not be crucial to retain or separate efficiently smaller non-linked peptides.

The 100 Å pore size superficially porous column was capable of separating the smallest peptides with peak widths and shapes comparable to the BEH C18 columns. However, peak shapes for the largest peptides (3-12 kDa) were noticeably worse. In addition, this column did not resolve the three largest polypeptides. Our data suggest that the superficially porous C18 column is limited to the analysis of smaller peptides, whereas the CSH130 and BEH130/300 C18 can separate a wider range of peptides and small proteins.

INCORPORATION BY REFERENCE

The entire contents of all patents published patent applications and other references cited herein are hereby expressly incorporated herein in their entireties by reference.

EQUIVALENTS

Those skilled in the art will recognize, or be able to ascertain using no more than routine experimentation, numerous equivalents to the specific procedures described herein. Such equivalents are considered to be within the scope of this invention and are covered by the following claims.

What is claimed is:

1. A method for selectively isolating, separating or purifying a peptide, protein, nucleic acid, or nucleotide from a sample, the method comprising the steps of:

a) loading a sample containing a macromolecule onto a chromatographic separations device comprising a high purity chromatographic material comprising a chromatographic surface wherein the chromatographic surface comprises a hydrophobic surface group and one or more ionizable modifiers, and the concentration of ionizable modifiers is more than 0.03μmol/m$^2$ and less than 0.5 μmol/m$^2$ of the specific surface area, and the ratio of the hydrophobic surface group : ionizable modifier is from about 4:1 to about 12:1, such that the macromolecule is selectively adsorbed onto the high purity chromatographic material, with the proviso that when the ionizable modifier does not contain a Zwitterion, the ionizable modifier does not contain a quaternary ammonium ion moiety;

wherein the ionizable modifier on the chromatographic surface is provided by reacting the chromatographic surface with an ionizable modifying reagent selected from groups having the formula (II):

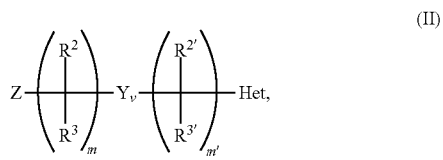

wherein
m is an integer from 1-8;
v is 0;
m' is 0;
Z represents a chemically reactive group, including (but not limited to)

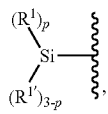

amine, alkylamine, dialkylamine, isocyanate, acyl chloride, thiocyanate, NHS-ester, carboxylic acid, ester, epoxide, alkyne, alkene, or azide;
Y is an embedded polar functionality;
each occurrence of R$^1$ independently represents a chemically reactive group on silicon, comprising: —H, —OH, —OR$^6$, dialkylamine, triflate, Br, Cl, I, vinyl, or alkene;
p is an integer from 1-3;
each occurrence of R$^{1'}$ independently represents F, C$_1$-C$_{18}$ alkyl, C$_2$-C$_{18}$ alkenyl, C$_2$-C$_{18}$ alkynyl, C$_3$-C$_{18}$ cycloalkyl, C$_1$-C$_{18}$ heterocycloalkyl, C$_5$-C$_{18}$ aryl, C$_5$-C$_{18}$ aryloxy, or C$_1$-C$_{18}$ heteroaryl, fluoroalkyl, or fluoroaryl;

each occurrence of R$^2$, R$^{2'}$, R$^3$ and R$^{3'}$ independently represents hydrogen;
each occurrence of R$^6$ independently represents C$_1$-C$_{18}$ alkyl, C$_2$-C$_{18}$ alkenyl, C$_2$-C$_{18}$ alkynyl, C$_3$-C$_{18}$ cycloalkyl, C$_1$-C$_{18}$ heterocycloalkyl, C$_5$-C$_{18}$ aryl, C$_5$-C$_{18}$ aryloxy, or C$_1$-C$_{18}$ heteroaryl; and
Het is pyridyl;
and b) eluting the adsorbed macromolecule from the high purity chromatographic material, thereby selectively isolating the macromolecule from the sample.

2. The method of claim 1, wherein the peptide, protein, nucleic acid, or nucleotide is selected from the group consisting of a peptide, a polypeptide, a phosphopeptide, a glycopeptide, a protein, a glycoprotein, an antibody, a phosphoprotein, a nucleic acid, an oligonucletoide, a polynucleotide, and mixtures thereof.

3. The method of claim 1, wherein the high purity chromatographic material further comprising a chromatographic core material.

4. The method of claim 1, wherein the ionizable modifying reagent is, 2-(2-(trichlorosilyl)ethyl)pyridine, 2-(2-(trimethoxy)ethyl)pyridine, 2-(2-(triethoxy)ethyl)pyridine, 2-(4-pyridylethyl)triethoxysilane, 2-(4-pyridylethyl) trimethoxysilane, 2-(4-pyridylethyl)trichlorosilane.

5. The method of claim 1, wherein the hydrophobic surface group is a C4 to C30 bonded phase, an aromatic, a phenylalkyl, a fluoro-aromatic, a phenylhexyl, a pentafluorophenylalkyl, or a chiral bonded phase.

6. The method of claim 1 wherein the chromatographic core is a silica material or a hybrid inorganic/organic material.

7. The method of claim 6, wherein the chromatographic core is a superficially porous material.

8. The method of claim 1, wherein the chromatographic separations device is a device is selected from the group consisting of a chromatographic column, a thin layer plate, a filtration membrane, a microfluidic separation device, a sample cleanup device, a solid support, a solid phase extraction device, a microchip separation device, and a microtiter plate.

9. The method of claim 1, further comprising the step of preparing the sample by treating a mother sample to a secondary chromatographic means to obtain the sample.

10. The method of claim 9, wherein the secondary chromatographic means is a second chromatographic separations device comprising a chromatographic material which is not comprising a chromatographic surface wherein the chromatographic surface comprises a hydrophobic surface group and one or more ionizable modifiers, or a second chromatographic material in the chromatopgraphic separations device which is not comprising a chromatographic surface wherein the chromatographic surface comprises a hydrophobic surface group and one or more ionizable modifiers.

11. The method of claim 10 wherein the secondary chromatographic separations device is a device is selected from the group consisting of a chromatographic column, a thin layer plate, a filtration membrane, a microfluidic separation device, a sample cleanup device, a solid support, a solid phase extraction device, a microchip separation device, and a microtiter plate.

12. The method of claim 1, further comprising the step of treating the macromolecules eluted in step b with a secondary chromatographic means to further isolate, purify, or separate the macromolecules.

13. A method for detecting a peptide, protein, nucleic acid, or nucleotide in a sample, the method comprising the steps of:
a) loading a sample containing a macromolecule onto chromatographic separations device comprising a high purity chromatographic material comprising a chromatographic surface wherein the chromatographic surface comprises a hydrophobic surface group and one or more ionizable modifiers, and the concentration of ionizable modifiers is more than $0.03 \mu mol/m^2$ and less than $0.5 \mu mol/m^2$ of the specific surface area, and the ratio of the hydrophobic surface group : ionizable modifier is from about 4:1 to about 12:1, such that the macromolecules are adsorbed onto the high purity chromatographic material, with the proviso that when the ionizable modifier does not contain a Zwitterion, the ionizable modifier does not contain a quaternary ammonium ion moiety;

wherein the ionizable modifier on the chromatographic surface is provided by reacting the chromatographic surface with an ionizable modifying reagent selected from groups having the formula (II):

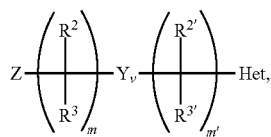

(II)

wherein
m is an integer from 1-8;
v is 0;
m' is 0;

Z represents a chemically reactive group, including (but not limited to)

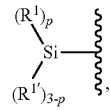

amine, alkylamine, dialkylamine, isocyanate, acyl chloride, thiocyanate, NHS-ester, carboxylic acid, ester, epoxide, alkyne, alkene, or azide;

Y is an embedded polar functionality;

each occurrence of $R^1$ independently represents a chemically reactive group on silicon, comprising: —H, —OH, —$OR^6$, dialkylamine, triflate, Br, Cl, I, vinyl, or alkene;

p is an integer from 1-3;

each occurrence of $R^{1'}$ independently represents F, $C_1$-$C_{18}$ alkyl, $C_2$-$C_{18}$ alkenyl, $C_2$-$C_{18}$ alkynyl, $C_3$-$C_{18}$ cycloalkyl, $C_1$-$C_{18}$ heterocycloalkyl, $C_5$-$C_{18}$ aryl, $C_5$-$C_{18}$ aryloxy, or $C_1$-$C_{18}$ heteroaryl, fluoroalkyl, or fluoroaryl;

each occurrence of $R^2$, $R^{2'}$, $R^3$ and $R^{3'}$ independently represents hydrogen;

each occurrence of $R^6$ independently represents $C_1$-$C_{18}$ alkyl, $C_2$-$C_{18}$ alkenyl, $C_2$-$C_{18}$ alkynyl, $C_3$-$C_{18}$ cycloalkyl, $C_1$-$C_{18}$ heterocycloalkyl, $C_5$-$C_{18}$ aryl, $C_s$-$C_{18}$ aryloxy, or $C_1$-$C_{18}$ heteroaryl; and Het is pyridyl; and b) eluting the adsorbed macromolecule from the high purity chromatographic material; and
c) detecting the macromolecule.

* * * * *